United States Patent
Carignan et al.

(10) Patent No.: US 12,318,638 B2
(45) Date of Patent: *Jun. 3, 2025

(54) DEVICES AND METHODS FOR REDUCING PARASYMPATHETIC NERVE ACTIVITY IN PATIENTS WITH A RESPIRATORY SYNDROME

(71) Applicant: Sonivie Ltd., Rosh HaAyin (IL)

(72) Inventors: Charles S. Carignan, Boston, MA (US); Or Shabtay, Kibbutz Farod (IL); Maya Rosenstein, Rishon le-Zion (IL); Dalit Shav, Glen Rock, NJ (US); Talia Cohen Keizman, Rishon LeZion (IL); Daniel Naor, Modi'in (IL); Ofek Admon, Ramat-Gan (IL)

(73) Assignee: Sonivie Ltd., Rosh HaAyin (IL)

( * ) Notice: Subject to any disclaimer, the term of this patent is extended or adjusted under 35 U.S.C. 154(b) by 2 days.

This patent is subject to a terminal disclaimer.

(21) Appl. No.: 17/960,893

(22) Filed: Oct. 6, 2022

(65) Prior Publication Data
US 2023/0037695 A1 Feb. 9, 2023

Related U.S. Application Data

(63) Continuation of application No. PCT/IL2021/050396, filed on Apr. 7, 2021, which is
(Continued)

(51) Int. Cl.
*A61N 7/02* (2006.01)
*A61B 1/018* (2006.01)
(Continued)

(52) U.S. Cl.
CPC .............. *A61N 7/022* (2013.01); *A61B 1/018* (2013.01); *A61B 1/2676* (2013.01); *A61M 25/10* (2013.01);
(Continued)

(58) Field of Classification Search
CPC .............. A61N 7/022; A61N 2007/003; A61N 2007/0078; A61B 1/018; A61B 1/2676;
(Continued)

(56) References Cited

U.S. PATENT DOCUMENTS

| 7,027,869 B2 | 4/2006 | Danek et al. |
| 7,198,635 B2 | 4/2007 | Danek et al. |

(Continued)

FOREIGN PATENT DOCUMENTS

| WO | WO 2009/137446 | 11/2009 |
| WO | WO 2021/205450 | 10/2021 |

OTHER PUBLICATIONS

Supplementary European Search Report and the European Search Opinion Dated Apr. 3, 2024 From the European Patent Office Re. Application No. 21784208.7. (9 Pages).
(Continued)

*Primary Examiner* — Alexei Bykhovski

(57) ABSTRACT

Some embodiments relate to a method of reducing excess mucosa production and/or secretion in the respiratory tract, comprising: introducing into a respiratory tract lumen a device configured for damaging nerve tissue or blocking neural conduction in the surroundings of said lumen, the device comprising a plurality of energy emitters; positioning the energy emitters of the device inside the lumen at a distance from walls of the lumen; and activating the energy emitters to emit energy suitable to damage the nerve tissue enough to suppress parasympathetic nerve activity which causes excess mucosa production and/or secretion.

20 Claims, 46 Drawing Sheets
(9 of 46 Drawing Sheet(s) Filed in Color)

Related U.S. Application Data a continuation-in-part of application No. 16/936,443, filed on Jul. 23, 2020, now Pat. No. 11,007,001.

(60) Provisional application No. 63/006,196, filed on Apr. 7, 2020.

(51) Int. Cl.
*A61B 1/267* (2006.01)
*A61M 25/10* (2013.01)
*A61N 7/00* (2006.01)

(52) U.S. Cl.
CPC ............... *A61N 2007/003* (2013.01); *A61N 2007/0078* (2013.01)

(58) Field of Classification Search
CPC .. A61M 25/10; A61M 25/02; A61M 25/0082; A61M 2025/0293; A61M 2210/1032
See application file for complete search history.

(56) References Cited

U.S. PATENT DOCUMENTS

| | | |
|---|---|---|
| 8,911,439 B2 | 12/2014 | Mayse et al. |
| 10,610,283 B2 | 4/2020 | Mayse et al. |
| 10,702,337 B2 | 7/2020 | Waldstreicher et al. |
| 2002/0002371 A1* | 1/2002 | Acker .................... A61N 7/022 607/113 |
| 2004/0010289 A1 | 1/2004 | Biggs et al. |
| 2009/0192505 A1 | 7/2009 | Askew et al. |
| 2009/0306644 A1 | 12/2009 | Mayse et al. |
| 2011/0301587 A1 | 12/2011 | Deem et al. |
| 2013/0012844 A1 | 1/2013 | Demarais et al. |
| 2013/0012867 A1 | 1/2013 | Demarais et al. |
| 2013/0324989 A1 | 12/2013 | Leung et al. |
| 2014/0005706 A1 | 1/2014 | Gelfand et al. |
| 2015/0112234 A1 | 4/2015 | McCaffrey et al. |
| 2015/0141985 A1 | 5/2015 | Mayse et al. |
| 2016/0113699 A1 | 4/2016 | Sverdlik et al. |
| 2016/0220851 A1* | 8/2016 | Mayse ............... A61B 18/1492 |
| 2016/0287912 A1* | 10/2016 | Warnking ............ A61B 8/5207 |
| 2016/0310210 A1 | 10/2016 | Harshman et al. |
| 2018/0345046 A1 | 12/2018 | Gallup |
| 2019/0201089 A1* | 7/2019 | Waldstreicher .... A61B 18/1206 |
| 2019/0201743 A1* | 7/2019 | Meyer ................. A61M 16/024 |

OTHER PUBLICATIONS

International Preliminary Report on Patentability Dated Oct. 20, 2022 From the International Bureau of WIPO Re. Application No. PCT/IL2021/050396. (15 Pages).

International Search Report and the Written Opinion Dated Sep. 1, 2021 From the International Searching Authority Re. Application No. PCT/IL2021/050396. (19 Pages).

Invitation to Pay Additional Fees Dated May 28, 2021 From the International Searching Authority Re. Application No. PCT/IL2021/050396. (2 Pages).

Notice of Allowance Dated Jan. 26, 2021 From the US Patent and Trademark Office Re. U.S. Appl. No. 16/936,443. (7 Pages).

Official Action Dated Nov. 24, 2020 from the US Patent and Trademark Office Re. U.S. Appl. No. 16/936,443. (12 pages).

Slebos et al. "Safety and Adverse Events After Targeted Lung Denervation for Symptomatic Moderate to Severe COPD (AIR-FLOW): A Multicenter Randomized Controlled Clinical Trial", American Journal of Respiratory and Critical Care Medicine, 200(12): 1477-1486, Published Online Aug. 12, 2019.

Slebos et al. "Targeted Lung Denervation for Moderate to Severe COPD: A Pilot Study", Thorax, 70(5): 411-419, Published Online Mar. 4, 2015.

Valipour et al. "Safety and Dose Study of Targeted Lung Denervation in Moderate/Severe COPD Patients", Respiration, 98(4): 329-339, Published Online Jun. 20, 2019.

* cited by examiner

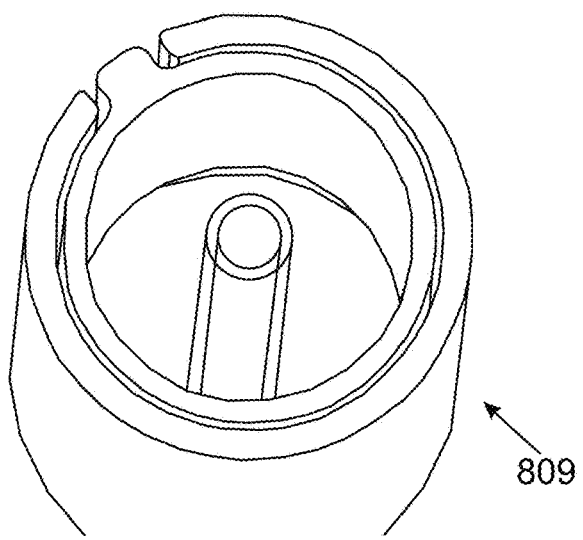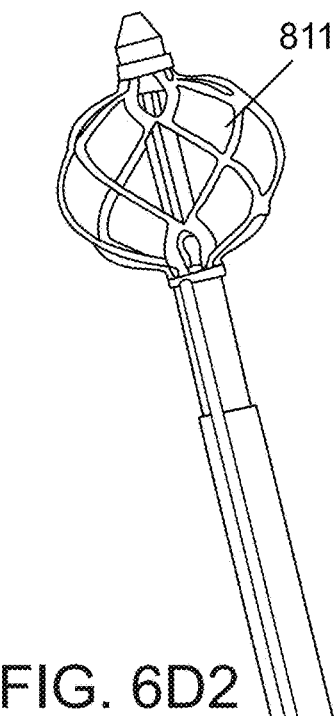
FIG. 6D1  FIG. 6D2
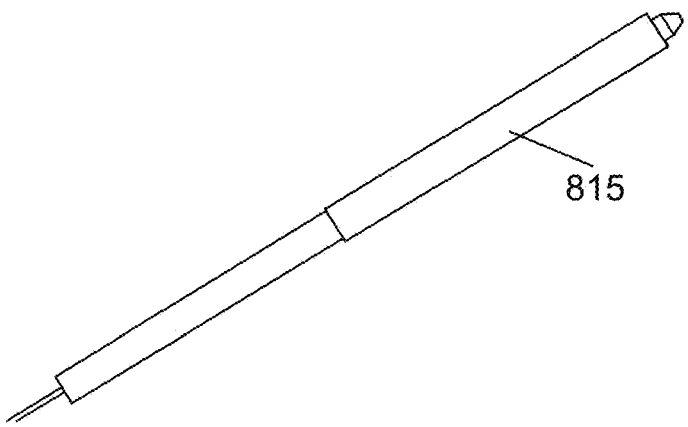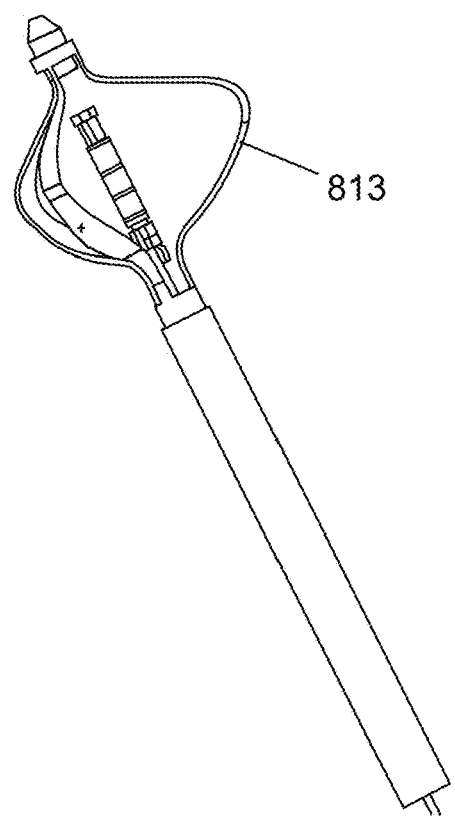
FIG. 6E2
FIG. 6E1

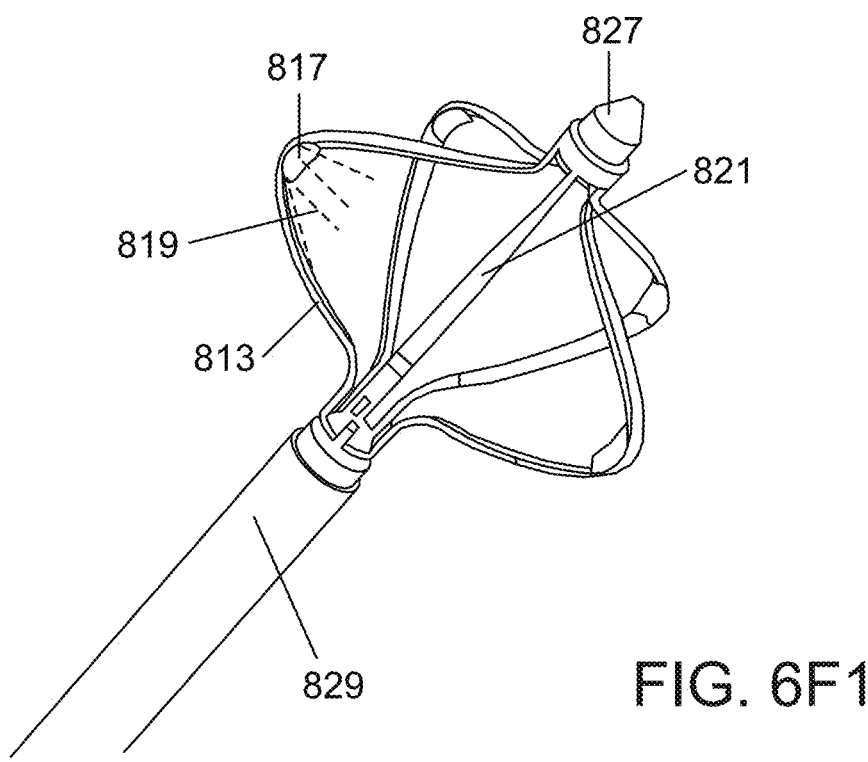
FIG. 6F1
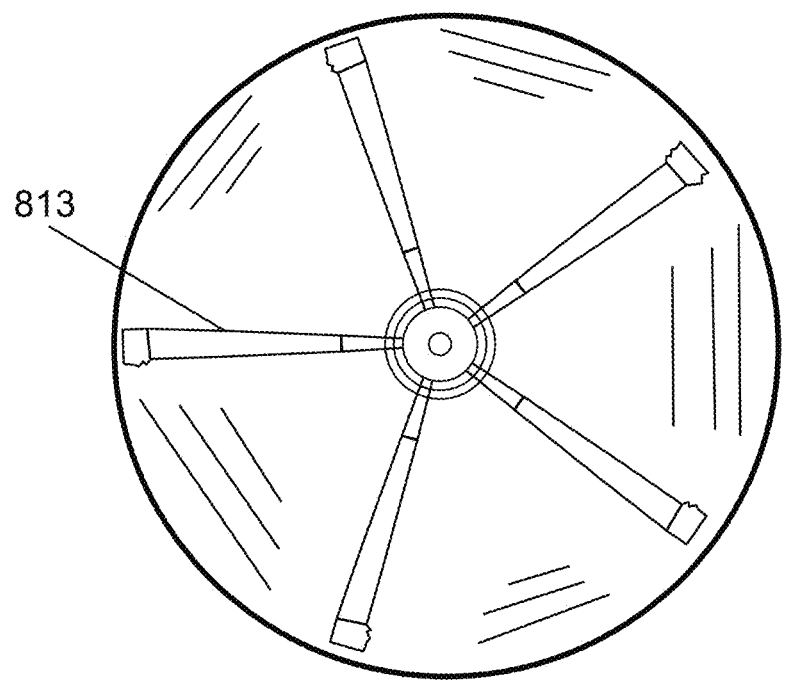
FIG. 6F2

2411

2409   2403   2405   2407

2401

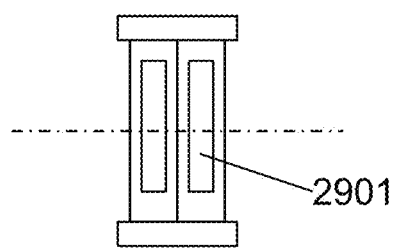
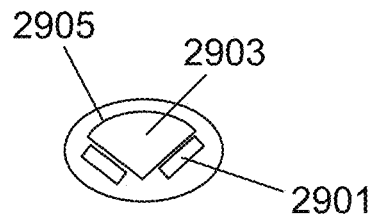
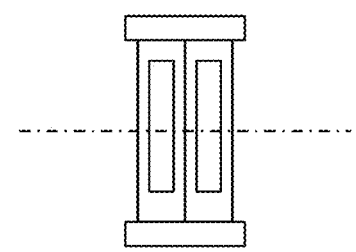
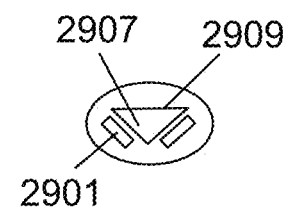
FIG. 29A         FIG. 29B

|  | Before procedure | | | Post procedure | | |
|---|---|---|---|---|---|---|
| Assessment location | Control location | Right bronchus | Left bronchus | Control location | Right bronchus | Left bronchus |
| HBR assessment | Not done | Reflex noticed | Reflex noticed | Not done | Reflex not noticed | Reflex not noticed |
| Distal pressure [mmHg] | NA | 40 | 20 | NA | 30 | 40 |
| Time | NA | 10:45 | 10:15 | NA | 13:27 | 13:23 |

|  | Before procedure | | | Post procedure | | |
|---|---|---|---|---|---|---|
| Assessment location | Control location | Right bronchus | Left bronchus | Control location | Right bronchus | Left bronchus |
| HBR assessment | Not done | Reflex noticed | Reflex noticed | Not done | Reflex not noticed | Reflex noticed |
| Distal pressure [mmHg] | NA | 40 | 40 | NA | 30 | 40 |
| Time | NA | 14:36 | 14:45 | NA | 16:11 | 16:15 |

FIG. 34

| Procedure phase | Peak pressure [cmH2O] | Threshold pressure [cmH2O] | VT [L] | T [sec] | Freq [BPM] | Flow [L/min] | ΔP | Airway resistance [cmH2O/(L/min)] |
|---|---|---|---|---|---|---|---|---|
| Before Atropine | 22.15 | 20.85 | 0.89 | 0.92 | 12 | 58.04347826 | 1.3 | 0.022397004 |
| Before Atropine | 22.42 | 20.86 | 0.89 | 0.9 | 12 | 59.33333333 | 1.56 | 0.026292135 |
| Before Atropine | 22.29 | 20.9 | 0.89 | 0.93 | 12 | 57.41935484 | 1.39 | 0.024207865 |
| After Atropine | 22.15 | 20.81 | 0.89 | 0.89 | 12 | 60 | 1.34 | |
| After Atropine | 22.09 | 20.74 | 0.89 | 0.9 | 12 | 59.33333333 | 1.35 | 0.022752809 |
| After Atropine (second dose +7ml) | 22.4 | 21.11 | 0.89 | 0.9 | 12 | 59.33333333 | 1.29 | 0.021741573 |
| After Atropine (second dose +7ml) | 22.27 | 20.97 | 0.89 | 0.89 | 12 | 60 | 1.3 | 0.02166667 |
| After Atropine (second dose +7ml) | 22.22 | 20.94 | 0.89 | 0.9 | 12 | 59.33333333 | 1.28 | 0.021573034 |
| After Atropine (second dose +7ml) | 21.7 | 20.56 | 0.89 | 0.92 | 12 | 58.04347826 | 1.14 | 0.019640449 |
| After Atropine (second dose +7ml) | 22.18 | 20.44 | 0.89 | 0.89 | 12 | 60 | 1.74 | 0.029 |
| After Atropine (second dose +7ml) | 22.27 | 20.88 | 0.89 | 0.9 | 12 | 59.33333333 | 1.39 | |
| After Atropine (second dose +7ml) | 22.31 | 20.76 | 0.89 | 0.89 | 12 | 60 | 1.55 | |
| After TLD | 23.22 | 22.58 | 0.87 | 1.03 | 12 | 50.67961165 | 0.64 | 0.012628352 |
| After TLD | 20.6 | 19.92 | 0.81 | 0.97 | 12 | 50.10309278 | 0.68 | 0.013572016 |
| After TLD | 20.79 | 20.2 | 0.81 | 0.994 | 12 | 48.89336016 | 0.59 | 0.012067078 |

FIG. 35A

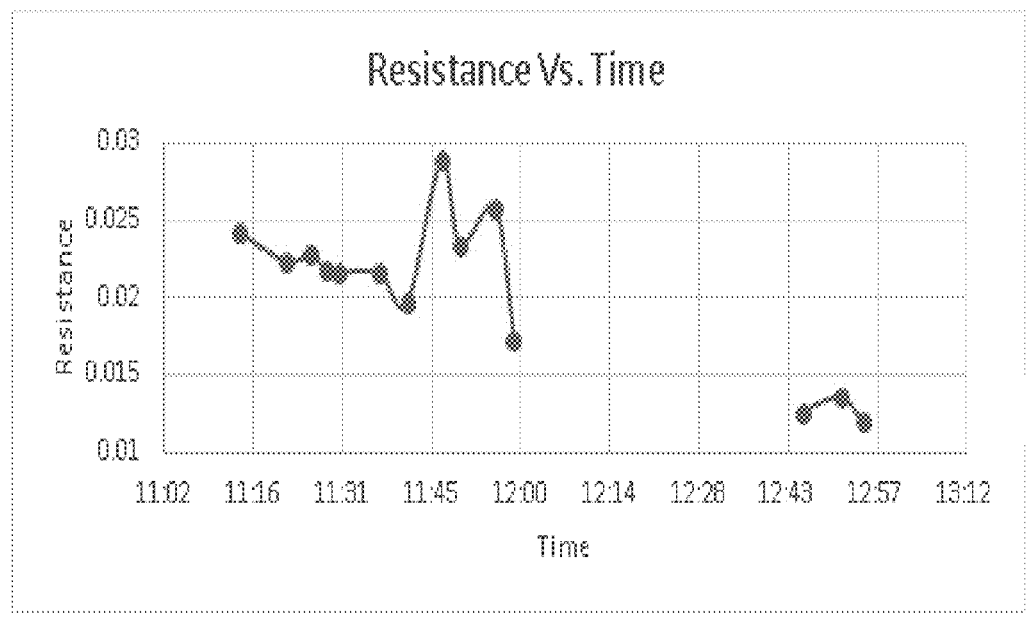
FIG. 35B
| Procedure phase | Airway resistance [mBar/L/min] | Airway resistance in % |
|---|---|---|
| Baseline | 0.0425 | 100% |
| After the first dose of Atropine | 0.0422 | 99% |
| After the second dose of Atropine | 0.0404 | 95% |
| Returning to baseline | 0.0414 | 97% |
| After TLD phase | 0.0252 | 59% |
FIG. 35C
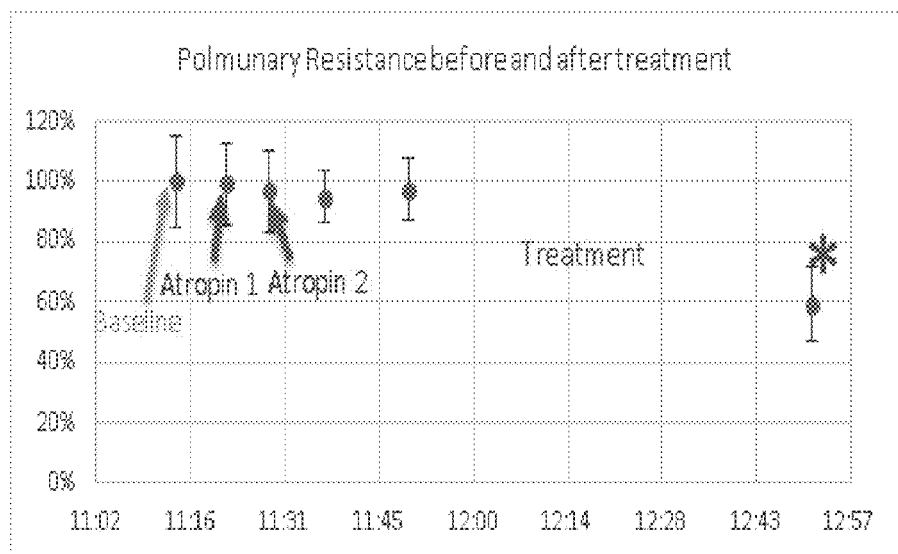
FIG. 35D

| Procedure phase | Peak pressure [cmH2O] | Threshold pressure [cmH2O] | VT [L] | T [sec] | Freq [BPM] | Flow [L/min] | ΔP | Airway resistance [cmH2O/L/min] |
|---|---|---|---|---|---|---|---|---|
| Before TLD | 21.17 | 20.04 | 0.8 | 1 | 12 | 48 | 1.13 | 0.02121875 |
| Before TLD | 21.17 | 20.2 | 0.8 | 1.05 | 12 | 45.71428571 | 0.97 | 0.019147917 |
| Before TLD | 21.08 | 20.17 | 0.8 | 1.01 | 12 | 47.52475248 | 0.91 | 0.015208333 |
| Before TLD | 20.92 | 20.19 | 0.8 | 1 | 12 | 48 | 0.73 | 0.015208333 |
| Before TLD | 21.15 | 20.1 | 0.8 | 1.03 | 12 | 46.60194175 | 1.05 | 0.02253125 |
| Before TLD | 21.15 | 19.62 | 0.8 | 1.02 | 12 | 47.05882353 | 1.53 | 0.0325125 |
| Before TLD | 21.08 | 19.88 | 0.8 | 1.01 | 12 | 47.52475248 | 1.2 | 0.02525 |
| Before TLD | 21.24 | 19.88 | 0.8 | 1.01 | 12 | 47.52475248 | 1.36 | 0.028616667 |
| Before TLD | 21.24 | 19.69 | 0.8 | 1.04 | 12 | 46.15384615 | 1.55 | 0.033583333 |
| After TLD | 20.42 | 19.56 | 0.8 | 0.91 | 12 | 52.74725275 | 0.86 | 0.016304167 |
| After TLD | 21.04 | 19.35 | 0.8 | 0.95 | 12 | 50.52631579 | 1.69 | 0.033447917 |
| After TLD | 20.95 | 19.58 | 0.8 | 0.93 | 12 | 51.61290323 | 1.37 | 0.02654375 |
| After TLD | 20.99 | 19.51 | 0.8 | 0.94 | 12 | 51.06382979 | 1.48 | 0.028983333 |
| After TLD | 22.24 | 21.15 | 0.8 | 1.03 | 12 | 46.60194175 | 1.09 | 0.023389583 |

FIG. 36A

| Procedure phase | Airway resistance $[\frac{cmH_2O}{L/min}]$ | Airway resistance in % |
|---|---|---|
| Baseline | 0.0328 | 100 % |
| After TLD phase | 0.0339 | 103 % |

| Treatment location | Bronchus branch (Rt.-Right/ Lt.-Left) | Excitation No. | Excitation power [W] | Excitation duration [sec] | Remarks |
|---|---|---|---|---|---|
| 1 | Rt. | 1 | 50 | 40 | |
| | Rt. | 2 | 50 | 30 | 180 deg EEprom error, excitation was stopped |
| 2 | Lt. | 3 | 50 | 40 | |
| | Lt. | 4 | 50 | 19 | 180 deg, balloon was damaged, excitation was stopped |
| | Lt. | 4 | 50 | 40 | |

FIG. 37A

| Treatment location | Bronchus branch (Rt.-Right/ Lt.-Left) | Excitation No. | Excitation power [W] | Excitation time [sec] | Remarks |
|---|---|---|---|---|---|
| 1' | Rt. | 1 | 50 | 60 | |
| | Rt. | 2 | 50 | 60 | 180 deg |
| 1 | Rt. | 3 | 50 | 60 | |
| | Rt. | 4 | 50 | 60 | 180 deg |
| 2 | Lt. | 5 | 50 | 60 | |
| | Lt. | 6 | 50 | 60 | 180 deg |

FIG. 37B

DEVICES AND METHODS FOR REDUCING PARASYMPATHETIC NERVE ACTIVITY IN PATIENTS WITH A RESPIRATORY SYNDROME

RELATED APPLICATIONS

This application is a Continuation of PCT Patent Application No. PCT/IL2021/050396 having International filing date of Apr. 7, 2021, which is a Continuation-in-Part (CIP) of U.S. patent application Ser. No. 16/936,443 filed on Jul. 23, 2020, now U.S. Pat. No. 11,007,001, which claims the benefit of priority under 35 USC § 119(e) of U.S. Provisional Patent Application No. 63/006,196 filed on Apr. 7, 2020. The contents of the above applications are all incorporated by reference as if fully set forth herein in their entirety.

FIELD AND BACKGROUND OF THE INVENTION

The present invention, in some embodiments thereof, relates to modifying (e.g. reducing) parasympathetic nerve activity in patients suffering from a respiratory syndrome, and more particularly but not exclusively, to the treatment of respiratory syndromes associated with bronchoconstriction and/or increased mucus production.

A publication titled "Safety and Adverse Events after Targeted Lung Denervation for Symptomatic Moderate to Severe COPD (AIRFLOW): A Multicenter Randomized Controlled Trial" by Slebos et al. published in AJRCCM Articles on 12 Aug. 2019 as 10.1164/rccm.201903-06240C discloses: "Targeted Lung Denervation (TLD) is a bronchoscopic radiofrequency ablation therapy for COPD, which durably disrupts parasympathetic pulmonary nerves to decrease airway resistance and mucous hyper-secretion." (Abstract);

A publication titled Safety and Dose Study of Targeted Lung Denervation in Moderate/Severe COPD Patients" by Valipour et al. published in Interventional Pulmonology on Jun. 20, 2019 discloses: "Rationale: Targeted lung denervation (TLD) is a novel bronchoscopic treatment for the disruption of parasympathetic innervation of the lungs. Objectives: To assess safety, feasibility, and dosing of TLD in patients with moderate to severe COPD using a novel device design. Methods: Thirty patients with COPD (forced expiratory volume in 1 s 30-60%) were 1:1 randomized in a double-blinded fashion to receive TLD with either 29 or 32 W. Primary endpoint was the rate of TLD associated adverse airway effects that required treatment through 3 months. Assessments of lung function, quality of life, dyspnea, and exercise capacity were performed at baseline and 1-year follow-up. An additional 16 patients were enrolled in an open-label confirmation phase study to confirm safety improvements after procedural enhancements following gastrointestinal adverse events during the randomized part of the trial. Results: Procedural success, defined as device success without an in-hospital serious adverse event, was 96.7% (29/30). The rate of TLD-associated adverse airway effects requiring intervention was 3/15 in the 32 W versus 1/15 in the 29 W group, p=0.6. Five patients early in the randomized phase experienced serious gastric events. The study was stopped and procedural changes made that reduced both gastrointestinal and airway events in the subsequent phase of the randomized trial and follow-up confirmation study. Improvements in lung function and quality of life were observed compared to baseline values for both doses but were not statistically different. Conclusions: The results demonstrate acceptable safety and feasibility of TLD in patients with COPD, with improvements in adverse event rates after procedural enhancements." (Abstract).

SUMMARY OF THE INVENTION

According to an aspect of some embodiments there is provided a method of reducing excess mucosa production and/or secretion in the respiratory tract, comprising: introducing into the lumen of the trachea or the lumen of the bronchi a device configured for damaging nerve tissue or blocking neural conduction in the surroundings of the lumen; and activating the device to damage the nerve tissue enough to suppress parasympathetic nerve activity which causes the excess mucosa production and/or secretion.

In some embodiments, the method comprises, prior to the introducing, selecting patients suffering from a respiratory condition associated with excess mucosa production and/or secretion, the respiratory condition being from the group of: bronchitis, chronic bronchitis, COPD, pneumonia, lung inflammation; and carrying out the activating.

In some embodiments, the method comprises, prior to the introducing, selecting patients suffering from a viral infection associated with excess mucosa production and/or secretion, the viral infection being from the group of: SARS, SARS-2, MERS, SARS-CoV-2, COVID-19; and carrying out the activating.

In some embodiments, activating comprises delivering energy suitable to thermally damage the nerve tissue.

In some embodiments, the energy is RF energy generated by one or more electrodes of the device.

In some embodiments, the energy is ultrasound energy emitted by one or more transducers of the device.

In some embodiments the ultrasound energy is transferred through a fluid medium in a balloon surrounding the one or more transducers.

In some embodiments, the method comprises introducing a blocking element into the lumen, and then partially filling the lumen with fluid which acts a transfer medium for the energy; the fluid allowed to accumulate in the lumen due to the blocking element.

In some embodiments, activating comprises generating an electric field or a magnetic field which damages the nerve tissue.

In some embodiments, activating comprises applying cryotherapy to block neural conduction by cooling the target nerves to a temperature below $-30°$ C.

In some embodiments, activating comprises injecting or releasing into tissue surrounding the lumen one or more substances from the group of: neurolytic blockers, medications, irritants, proteolytic enzymes, polyacid, toxins.

In some embodiments, the method further comprises assessing the effectiveness of treatment by sensing a humidity level in the lungs.

In some embodiments, the method further comprises assessing the effectiveness of treatment by triggering a natural reflex and detecting changes in that reflex caused by the damage to the nerves.

In some embodiments, the method further comprises anchoring at least a portion of the device to the wall of the lumen.

According to an aspect of some embodiments there is provided a method for treating a respiratory syndrome, comprising: introducing a device comprising at least one ultrasound emitting element into the lumen of the trachea or the lumen of the bronchi; emitting ultrasound energy suitable to thermally damage nerve tissue located peripherally to the lumen to reduce in mucus section, reduce bronchoconstriction; and/or reduction inflammation.

In some embodiments, the respiratory condition is from the group of: bronchitis, chronic bronchitis, COPD, pneumonia, lung inflammation.

In some embodiments, the respiratory condition is a condition associated with a viral infection from the group of: SARS, SARS-2, MER, COVID-19, SARS-CoV-2.

In some embodiments, introducing is via an endotracheal tube.

In some embodiments, emitting comprises emitting non-focused ultrasound energy.

In some embodiments, an intensity of the non-focused ultrasound energy is between 10 W/cm^2-50 W/cm^2 and a frequency is between 8 MHz-20 MHz.

In some embodiments, emitting is performed from a plurality of rotational positions along the lumen circumference.

In some embodiments, emitting is performed from a plurality of axial position along the lumen long axis.

In some embodiments, the at least one ultrasound emitting element is positioned within a fluid filled balloon.

In some embodiments, emitting heats the nerve tissue to a temperature between 50° C.-80° C.

In some embodiments, the method comprises positioning the at least one ultrasound emitting element within the lumen of the bronchi at a distance of between 1 cm to 10 cm from the trachea bifurcation.

In some embodiments, the nerve tissue comprises branches of the vagal nerve which innervate the lungs.

In some embodiments, the method comprises oscillating the ultrasound transmitting element at frequency of the delivered ultrasound energy to cause vibration of surrounding tissue.

In some embodiments, activating comprises activating the device to damage nerve tissue enough to reduce at least one of: a number of ACE2 receptors in the bronchus, and a binding affinity of the ACE2 receptors.

According to an aspect of some embodiments there is provided a system for treating a respiratory disorder by suppression of nerve activity, comprising: a catheter shaped and sized for insertion into the lumen of the trachea or the bronchus, the catheter including a head comprising one or more energy emitting elements; a balloon inflatable with a fluid medium and configured to surround the catheter head; and a control console configured for controlling emission of energy by the one or more energy emitting elements, the control console configured for setting energy parameters suitable to thermally damage nerve tissue surrounding the lumen.

In some embodiments, the catheter defines at least one conduit for the passing of air flow through.

In some embodiments, the controller is configured to control flow of air through the at least one conduit.

In some embodiments, the one or more energy emitting elements comprise ultrasound transducers.

In some embodiments, the one or more energy emitting elements comprise RF electrodes.

In some embodiments, the fluid medium comprises a fluid from the group of: saline, water, cooling fluid.

In some embodiments, the catheter is sized for insertion through an endotracheal tube.

According to an aspect of some embodiments there is provided a method for accelerating separation of lung mucus from tissue and/or for thinning mucus, comprising: introducing a device comprising an oscillating element into the lumen of the trachea and/or the lumen of a bronchus; and activating the oscillating element to at least one of oscillate and raise a temperature of surrounding tissue.

In some embodiments, the oscillations are transferred to the tissue via a fluid filled balloon surrounding the oscillating element.

In some embodiments, the oscillating element comprises an ultrasound transducer.

According to an aspect of some embodiments there is provided a method for assessing effectiveness of a denervation treatment applied from within the bronchus, comprising: sensing neural activity in a location proximal to a location from which denervation was applied, along the long axis of the lumen of the bronchus; and sensing neural activity in a location distal to a location from which denervation was applied, along the long axis of the lumen of the bronchus.

In some embodiments, the location proximal to the denervation location defines a control location which was not affected by the denervation; and wherein the location distal to the denervation location defines a location which was affected by treatment.

In some embodiments, sensing comprises detecting and/or measuring an electric field produced by neural conduction, the sensing performed using an electrode and/or an antennae.

According to an aspect of some embodiments there is provided a method of treating a patient suffering from a COVID-19 infection, comprising: selecting a patient suspected to have lung damage caused by the COVID-19 virus; and damaging or blocking nerves of the respiratory tract to: reduce lung mucus secretion; reduce inflammation; and/or reduce bronchoconstriction.

In some embodiments, damaging or blocking nerves comprises thermally damaging the nerves using ultrasound energy.

In some embodiments, damaging or blocking nerves reduces lung mucus secretion by between 30%-80% relative to the amount of mucus secreted before treatment.

In some embodiments, damaging or blocking nerves reduces at least one of: a number of receptors which bind to COVID-19 pathogens, and a binding affinity of the receptors.

In some embodiments, selecting a patient comprises selecting a patient previously diagnosed with a respiratory condition.

In some embodiments, selecting a patient comprises selecting a patient who does not suffer from a prior respiratory condition.

In some embodiments there is provided method for selectively modifying nerve activity without causing substantial damage to non-targeted tissue, comprising: introducing a catheter device comprising one or more ultrasonic transceivers to the pulmonary artery lumen; receiving, using the one or more ultrasonic transceivers, echo signals reflected from the non-targeted tissue following emission of ultrasound energy by the one or more ultrasonic transceivers; analyzing the received echo signals to identify at least one of a type and location of the non-targeted tissue relative to the one or more ultrasonic transceivers; and emitting ultrasound energy from the one or more ultrasonic transceivers in accordance with the analyzing, to modify nerve activity without substantially damaging the identified non-targeted tissue. In some embodiments, the method further comprises selecting at least one of a location of the transceivers, an orientation of the transceivers, and a denervation treatment profile according to the analyzing. In some embodiments, the non-targeted tissue comprises one or more of: lung, trachea, vagus, lymph, bronchi. In some embodiments, analyzing comprises determining a distance between the non-targeted tissue and the one or more transceivers. In some embodiments, analyzing comprises identifying targeted tissue. In some embodiments, emitting comprises targeting nerve tissue at a distance ranging between 0.5 mm to 10 mm from an inner wall of the artery lumen. In some embodiments, ultrasound energy is non-focused energy applied at an intensity sufficient to cause at least semi-permanent nerve modification to targeted tissue. In some embodiments, the method further comprises diagnosing the patient with one or more of pulmonary hypertension, asthma and/or COPD, and selecting a denervation treatment profile in accordance with the diagnosing. In some embodiments, the method further comprises collecting feedback and modifying the emitting based on the feedback by measuring one or more physiological parameters before and after the emitting. In some embodiments, one or more physiological parameters include one or more of heart rate, pulmonary artery diameter, bronchi diameter, cardiac output, respiratory rate, lung volumes, arterial constriction, pulmonary artery pressure, blood flow, artery stiffness. In some embodiments, the pulmonary artery diameter is estimated by analyzing echo signals reflected by walls of the artery and received by the one or more ultrasonic transceivers. In some embodiments, measuring comprises stimulating the sympathetic nervous system, and measuring the physiological parameter in response to the stimulation.

In some embodiments there is provided a method for selectively targeting nerve tissue, comprising: introducing a catheter comprising one or more ultrasonic transceivers to the pulmonary artery lumen; selecting to damage only nerves that are not coated by myelin; emitting ultrasound energy at a frequency, intensity and duration sufficient to damage only nerves that are not coated by myelin, by producing a predetermined temperature profile in the treated tissue, the temperature profile ranging between 47-57 degrees C. In some embodiments, the method comprises modifying at least one of the frequency, intensity and duration of the energy to produce a temperature profile ranging between 58-70 degrees C. in the treated tissue, to selectively damage both myelin coated nerves and non-coated nerves. In some embodiments, the method further comprises assessing a bronchial reaction to the emitting as feedback to the targeting, and modifying at least one of the frequency, intensity and duration of the energy in accordance with the bronchial reaction. In some embodiments, the method comprises positioning the one or more ultrasonic transceivers away from a wall of the pulmonary artery lumen to allow blood to flow between the transceivers and the wall.

In some embodiments there is provided an ultrasonic catheter for selectively targeting nerve tissue from a pulmonary artery lumen, comprising: a head configured at a distal end of the catheter, the head comprising one or more ultrasonic transceivers, the transceivers configured to emit non-focused ultrasound energy; a controller configured to select one or more of frequency, intensity and duration of the non-focused ultrasound energy emitted by the transceivers to selectively damage only nerves that are not coated by myelin. In some embodiments, the controller is configured to select one or more of the frequency, intensity and duration of the non-focused ultrasound energy emitted by the transceivers to selectively damage both myelin coated nerves and non-coated nerves.

In some embodiments there is provided an ultrasonic catheter device comprising: an elongated shaft; a head configured at a distal portion of the shaft, the head comprising a plurality of leaflets expandable in a radially outward direction relative to the shaft, each of the leaflets comprised of a rod-like element bendable into an elbow shaped configuration; and a plurality of ultrasonic transceivers, each transceiver mounted onto one of the expandable leaflets. In some embodiments, each of the transceivers comprises an energy emitting surface and an opposing surface, the opposing surface coupled to the leaflet to position the energy emitting surface to face a central direction. In some embodiments, a distal tip of the shaft is retractable for expanding the leaflets relative to the shaft and advanceable for contracting the leaflets closer to the shaft. In some embodiments, the transceiver is mounted onto the leaflet at the elbow shaped bend of the leaflet.

In some embodiments there is provided an ultrasonic catheter device for modifying nerve activity from an air filled lumen, comprising: a head comprising one or more ultrasonic transceivers, the transceivers configured to emit energy having parameters suitable to modify nerve tissue in target tissue; a balloon arrangement in which fluid is circulated, the balloon arrangement comprising at least an inner balloon, surrounding the transceivers, and an outer balloon, surrounding the inner balloon, wherein cold fluid is circulated in the inner balloon for cooling the one or more transceivers, and warm fluid is circulated in the outer balloon for enhancing a thermal heating effect of energy emitted by the transceivers, to effectively increase a depth of the produced ultrasonic field in the target tissue. In some embodiments, cold fluid and the warm fluid are the same fluid, the cold fluid heated as a result of cooling the transceivers and circulated as the warm fluid to enhance the thermal heating effect of the emitted energy. In some embodiments, the balloon arrangement comprises two or more balloons which when inflated cover only portions of the head, and do not surround the head circumferentially. In some embodiments, emitting surfaces of the one or more transceivers are exposed in between the balloons. In some embodiments, the balloon arrangement is configured to push the one or more transceivers away from a wall of the lumen when inflated. In some embodiments, the air filled lumen is the trachea.

In some embodiments there is provided a method for modifying nerve activity, comprising introducing a catheter device comprising at least one ultrasonic transceiver to the aorta; engaging the celiac artery ostium using an elongated tool extending from the catheter; and emitting ultrasound energy to modify nerve activity of the celiac ganglion. In some embodiments, the method comprises selecting a position of the at least one transceiver in the aorta in accordance with a location of the celiac artery ostium. In some embodiments, the method comprises positioning and orienting the at least one transceiver relative to the celiac artery ostium using the elongated tool.

In some embodiments there is provided a kit for modifying nerve activity of the celiac ganglion, comprising a catheter comprising at least one ultrasonic transceiver; an elongated tool extendible from the catheter, the tool long enough to engage the celiac artery ostium, the tool comprising a curvature suitable to direct the ultrasonic transceiver towards the celiac artery ostium when the tool engages the ostium. In some embodiments, the elongated tool comprises a rod insertable through a cannulated shaft of the catheter and extendible from a distal opening of the catheter shaft.

In some embodiments there is provided an ultrasonic catheter system for modifying nerve activity, comprising a catheter comprising a head at its distal end, the head comprising one or more ultrasonic emitters, the emitters configured to emit energy suitable for modifying nerve activity; a tool usable with the catheter, the tool comprising: a supporting section; an emitter-positioning section configured distally to the supporting section; wherein the catheter is cannulated to be advanced over the tool into a blood vessel, until the emitters are axially aligned with the emitter positioning section of the tool; wherein the tool is shaped and sized such that the supporting section leans against a vessel wall opposite the wall to be treated, setting a location of the emitter positioning section at a predetermined radial distance from the vessel wall to be treated. In some embodiments, the tool comprises a sigmoid shaped curvature, so that when the tool is within the blood vessel, the emitter-positioning section is located away from a central longitudinal axis of the vessel, at an angle to the longitudinal axis. In some embodiments, an arrangement of the emitters on the catheter head is selected so that when the head is advanced over the emitter-positioning section, an emitting surface of at least one of the emitters faces the vessel wall to be treated. In some embodiments, at least one of advancement of the catheter over the tool, and axial rotation of the tool when the catheter is positioned over it provide for treating the blood vessel circumferentially. In some embodiments, the tool is a guide wire, the guide wire comprising a spiral shape, the spiral having a cross sectional diameter which is no more than 10% smaller than a cross sectional diameter of the lumen. In some embodiments, the tool is a guide wire the guide wire comprising a Z shape, tracing a jagged path between the opposite walls of the body lumen so that when the guide wire is rotated, at least the one or more emitters are maintained at the predetermined radial distance from the lumen wall. In some embodiments, the catheter is positionable over the tool such that the head is proximal to at least one of the supporting section, and the emitter-positioning section.

In some embodiments there is provided an ultrasonic catheter for modifying nerve activity from within a blood vessel, comprising a shaft comprising at least one curved portion; a head configured at a distal end of the shaft, the head comprising one or more ultrasonic emitters, the emitters configured to emit energy suitable for modifying nerve activity; wherein the curved portion of the shaft comprises a sigmoid-shape curvature which pushes the head away from one wall of the blood vessel and in proximity to an opposite wall of the blood vessel. In some embodiments, the sigmoid shaped shaft portion distances the head away from a central longitudinal axis of the vessel, at an angle to the longitudinal axis. In some embodiments, an arrangement of the emitters on the catheter head is selected so that an emitting surface of at least one of the emitters faces the vessel wall to be treated. In some embodiments, axial rotation of the catheter provides for treating the blood vessel circumferentially. In some embodiments, the sigmoid shaped shaft portion comprises a cross sectional diameter which is no more than 10% smaller than a cross sectional diameter of the blood vessel.

In some embodiments there is provided a method for advancing an ultrasonic catheter within a body lumen while keeping at least emitters of the catheter at a predetermined radial distance range from the walls of the body lumen, comprising delivering a catheter comprising one or more ultrasonic emitters over a guide wire into a body lumen, the guide wire comprising a curvature selected in accordance with a cross sectional profile of the body lumen; advancing the catheter over the guide wire within the lumen, while the emitters are maintained within the predetermined radial distance range from a wall of the body lumen. In some embodiments, the radial distance range is between 1 mm from the wall of the body lumen, and 1 mm from a central longitudinal axis of the body lumen. In some embodiments, the cross sectional profile comprises a diameter of the body lumen, and the curvature of the guide wire comprises a diameter at least 5% shorter than the lumen diameter. In some embodiments, the catheter is advanced over the guide wire to a position in which the emitters are located proximally to the curvature of the guide wire. In some embodiments, the catheter comprises a single ultrasonic emitter, and wherein the method further comprises rotating the guide wire to treat the body lumen circumferentially.

In some embodiments there is provided an ultrasonic catheter structured to reduce movement of a distal portion of the catheter when at least a proximal portion of the catheter is subjected to movement resulting from heart pulsation, comprising a head configured at a distal end of the catheter, the head comprising one or more ultrasonic emitters configured to emit energy to modify nerve activity; a shaft comprising at least one axial decoupling at a distance of no more than 10 cm away from the head. In some embodiments, the axial decoupling is provided by a coil configured to dampen movement of the head when a proximal portion of the catheter is moved due to heart pulsation. In some embodiments, the catheter is sized for insertion into the pulmonary artery, the distance between the head and the axial decoupling selected so that when the head is positioned within the pulmonary artery, the axial decoupling is between the heart and the catheter head.

In embodiments there is provided a method for treating pulmonary hypertension, comprising inserting a catheter comprising one or more ultrasonic emitters into the pulmonary artery; emitting non-focused ultrasound energy to thermally damage nerve tissue; measuring pulmonary arterial pressure; modifying the emitting in accordance with the pulmonary arterial pressure. In some embodiments, the catheter is equipped with one or more pressure sensors, and the measuring of pulmonary arterial pressure is performed using the one or more pressure sensors. In some embodiments, the method further comprises measuring one or more of cardiac output, systemic pressure. In some embodiments, emitting is performed at a distance of at least 1 mm from the wall of the pulmonary artery, allowing blood to flow between the emitter and the wall.

In some embodiments there is provided a method for modifying nerve activity from within the pulmonary artery, comprising introducing a catheter comprising an ultrasonic emitter into the pulmonary artery; emitting ultrasound energy having parameters suitable for thermally damaging nerve tissue; axially rotating the catheter to emit the energy circumferentially towards the walls of the artery.

According to an aspect of some embodiments there is provided a method of reducing excess mucosa production and/or secretion in the respiratory tract, comprising:
  introducing into a respiratory tract lumen a device configured for damaging nerve tissue or blocking neural conduction in the surroundings of the lumen, the device comprising a plurality of energy emitters;
  positioning the energy emitters of the device inside the lumen at a distance from walls of the lumen; and
  activating the energy emitters to emit energy suitable to damage the nerve tissue enough to suppress parasympathetic nerve activity which causes the excess mucosa production and/or secretion.

In some embodiments, the method comprises, prior to the introducing, selecting patients suffering from a respiratory condition associated with excess mucosa production and/or secretion, the respiratory condition being from the group of: bronchitis, chronic bronchitis, COPD, pneumonia, lung inflammation; and carrying out the activating.

In some embodiments, the method comprises, prior to the introducing, selecting patients suffering from a viral infection associated with excess mucosa production and/or secretion, the viral infection being from the group of: SARS, SARS-2, MERS, SARS-CoV-2, COVID-19; and carrying out the activating.

In some embodiments, the respiratory tract lumen comprises the lumen of the trachea or the lumen of the bronchi.

In some embodiments, activating comprises delivering via the energy emitters energy suitable to thermally damage the nerve tissue.

In some embodiments, the energy is RF energy generated by one or more electrodes of the device.

In some embodiments, the energy is ultrasound energy emitted by one or more transducers of the device.

In some embodiments, the method comprises introducing a blocking element into the lumen, and then partially filling the lumen with fluid which acts a transfer medium for the energy; the fluid allowed to accumulate in the lumen due to the blocking element.

In some embodiments, activating comprises generating an electric field or a magnetic field which damages the nerve tissue.

In some embodiments, activating comprises applying cryotherapy to block neural conduction by cooling the target nerves to a temperature below −30° C.

In some embodiments, activating comprises injecting or releasing into tissue surrounding the lumen one or more substances from the group of: neurolytic blockers, medications, irritants, proteolytic enzymes, polyacid, toxins.

In some embodiments, the method further comprises assessing the effectiveness of treatment by at least one of sensing a humidity level in the lungs and triggering a natural reflex and detecting changes in the reflex caused by the damage to the nerves.

In some embodiments, the method comprises anchoring at least a portion of the device to the wall of the lumen.

In some embodiments, the plurality of energy emitters comprise ultrasound emitting elements, and the method comprises
  emitting ultrasound energy suitable to thermally damage nerve tissue located peripherally to the lumen to reduce in mucus section, reduce bronchoconstriction; and/or reduction inflammation.

In some embodiments, the method is applied for the treatment of a respiratory condition from the group of: bronchitis, chronic bronchitis, COPD, pneumonia, lung inflammation.

In some embodiments, the method is applied for the treatment of a respiratory condition associated with a viral infection from the group of: SARS, SARS-2, MER, COVID-19, SARS-CoV-2.

In some embodiments, introducing is via an endotracheal tube or a bronchoscope working channel.

In some embodiments, the ultrasound energy is non-focused ultrasound energy.

In some embodiments, an intensity of the non-focused ultrasound energy is between 10 W/cm^2-50 W/cm^2 and a frequency is between 8 MHz-20 MHz.

In some embodiments, emitting is performed from: a plurality of rotational positions along the lumen circumference; a plurality of axial position along the lumen long axis.

In some embodiments, the plurality of energy emitters are positioned within a fluid filled balloon.

In some embodiments, emitting heats the nerve tissue to a temperature between 50° C.-80° C.

In some embodiments, the method comprises positioning the ultrasound emitting elements within the lumen of the bronchi at a distance of between 1 cm to 10 cm from the trachea bifurcation.

In some embodiments, the method comprises oscillating the ultrasound emitting elements at frequency of the delivered ultrasound energy to cause vibration of surrounding tissue.

In some embodiments, activating comprises activating the device to damage the nerve tissue enough to reduce at least one of: a number of ACE2 receptors in the bronchus, and a binding affinity of the ACE2 receptors.

According to an aspect of some embodiments there is provided a method of treating a patient suffering from a COVID-19 infection, comprising:

- selecting a patient suspected to have lung damage caused by the COVID-19 virus; and
- damaging or blocking nerves of the respiratory tract to: reduce lung mucus secretion; reduce inflammation; and/or reduce bronchoconstriction.

In some embodiments, damaging or blocking nerves comprises thermally damaging the nerves using ultrasound energy.

In some embodiments, damaging or blocking nerves reduces lung mucus secretion by between 30%-80% relative to the amount of mucus secreted before treatment.

In some embodiments, damaging or blocking nerves reduces at least one of: a number of receptors which bind to COVID-19 pathogens, and a binding affinity of the receptors.

In some embodiments, selecting a patient comprises selecting a patient previously diagnosed with a respiratory condition.

In some embodiments, selecting a patient comprises selecting a patient who does not suffer from a prior respiratory condition.

According to an aspect of some embodiments there is provided a system for treating a respiratory disorder by suppression of nerve activity, comprising:

- a catheter shaped and sized for insertion into the lumen of the trachea or the bronchus, the catheter including a head comprising one or more ultrasound emitting transducers;
- a balloon inflatable with a fluid medium and configured to surround the head; and
- a shield positioned and configured to block at least a portion of the energy emitted by the one or more ultrasound emitting transducers.

In some embodiments, the system comprises a control console configured for controlling emission of energy by the one or more ultrasound emitting transducers, the control console configured for setting energy parameters suitable to thermally damage nerve tissue surrounding the lumen into which the catheter is inserted.

In some embodiments, the catheter is sized to be introduced into the lumen via a working channel of a bronchoscope.

In some embodiments, the shield comprises an arc shaped cross section which extends along less than 40% of a perimeter of the catheter head.

In some embodiments, the shield comprises a thickness at least as long as an axial length of the one or more ultrasound emitting transducers.

In some embodiments, the shield is formed of a material configured for absorbing ultrasound energy emitted by the one or more ultrasound emitting transducers.

In some embodiments, the shield is integrally attached to a chassis of the catheter on which the ultrasound emitting transducers are mounted.

In some embodiments, the shield is mounted onto an inner wall and/or onto an outer wall of the balloon.

According to an aspect of some embodiments there is provided a method for treating a respiratory disorder by suppression of nerve activity while reducing or preventing thermal damage to the esophagus, comprising:

introducing into the bronchus a catheter comprising a distal head including a plurality of ultrasound transducers;

irradiating ultrasound energy suitable to damage nerves surrounding the bronchus, while reducing or preventing thermal damage to the esophagus.

In some embodiments, reducing or preventing thermal damage to the esophagus is by at least one of:

(a) positioning a shield which blocks at least a portion of the ultrasound energy emitted in the direction of the esophagus;

(b) selecting energy parameters such that a radial extent of the emitted ultrasound energy is shorter than a distance between the catheter head and the external wall of the esophagus;

(c) positioning the catheter such that ultrasound energy is emitted only from one or more transducers of the plurality of transducers which do not face the esophagus.

In some embodiments, the plurality of transducers comprise a single transducer and wherein the method further includes rotating the catheter head to emit ultrasound energy from the single transducer in multiple directions.

In some embodiments, the plurality of transducers comprise two transducers.

In some embodiments, the plurality of transducers comprise three transducers arranged in a triangular configuration.

According to an aspect of some embodiments there is provided an intraluminal catheter device for emission of ultrasound energy, comprising:

a head configured at a distal end of the catheter, the head comprising:

a ring shaped or disc shaped ultrasound transducer positioned to lie on a plane that is perpendicular to a long axis of the catheter head;

at least one cone shaped reflector positioned along the long axis such that a tapered end of the cone shaped reflector faces the ring shaped or disc shaped ultrasound transducer, the cone shaped reflector configured to reflect ultrasound energy emitted by the transducer radially outwardly.

According to an aspect of some embodiments there is provided a method for determining a type of medium and/or a change in the type of medium using an intraluminal ultrasound emitting catheter, comprising:

introducing the catheter into the trachea or the bronchus;

emitting ultrasound energy from a plurality of ultrasound transceivers of the catheter;

receiving returning ultrasound echoes; and analyzing the returning ultrasound echoes to determine a type of medium and/or a change in the type of medium, the analyzing comprising identifying a distance of the medium relative to a surface of at least one of the plurality of ultrasound transceivers.

In some embodiments, the medium is from the group of: blood, saline, air, cartilage, soft tissue, bone tissue.

In some embodiments, analyzing comprises identifying the esophagus based on the determination of an air filled cavity.

In some embodiments, the method further comprises emitting ultrasound energy having parameters suitable to thermally damage nerves surrounding the trachea or bronchus, while reducing or avoiding emission in the direction of the identified esophagus.

According to an aspect of some embodiments there is provided an adaptor for coupling a bronchoscope working channel to a handle of a catheter insertable into the bronchoscope working channel, comprising:

an elongate handle portion defining a long axis, the handle comprising a slot extending along the long axis;

a distal coupler extending from the handle portion, the distal coupler shaped and sized for fitting onto a proximal opening of the bronchoscope working channel;

a proximal coupler extending from the handle portion, the proximal coupler shaped and sized for receiving and holding a proximal portion of the catheter; the proximal coupler attached to a knob slidable along the slot; wherein sliding the knob along the slot advances or retracts the catheter within the bronchoscope working channel.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of neural networks and organs in the vicinity of a pulmonary artery, in a human thorax;

FIGS. 2A-2B illustrate an ultrasonic catheter device, according to some embodiments of the invention;

FIGS. 3A-3B illustrate an ultrasonic device used with a distancing device, according to some embodiments of the invention;

FIGS. 4A-4B are a flowchart of various aspects of selective treatment (4A), and a schematic graph of selectively treating different types of nerve tissue (4B), according to some embodiments of the invention;

FIG. 5 is a flowchart of an exemplary feedback loop associated with a denervation procedure, according to some embodiments of the invention;

Figure 7:
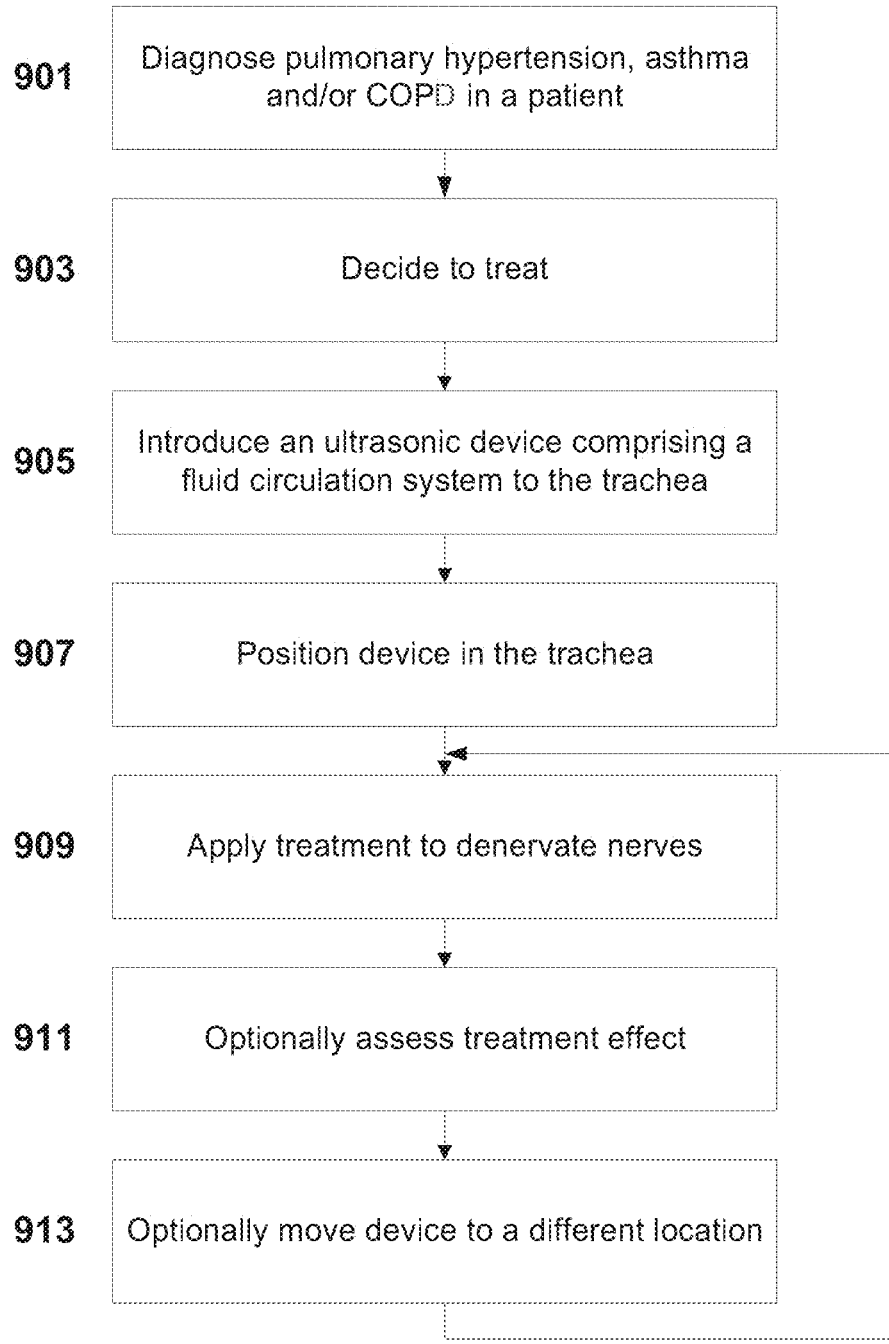
Figure 8A:
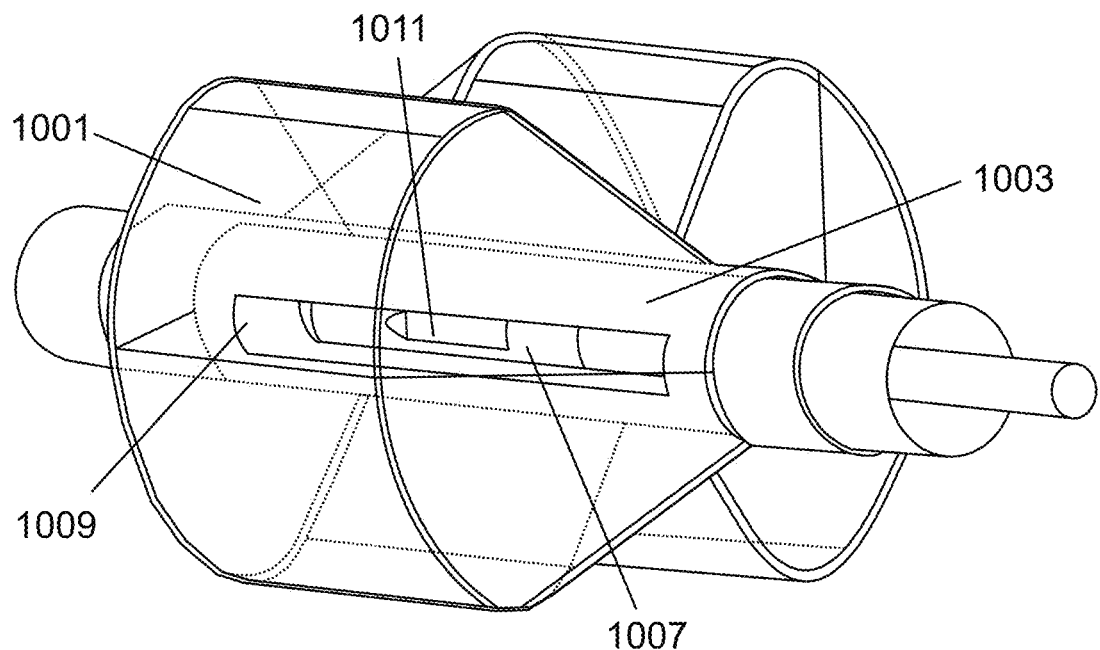
Figure 8B:
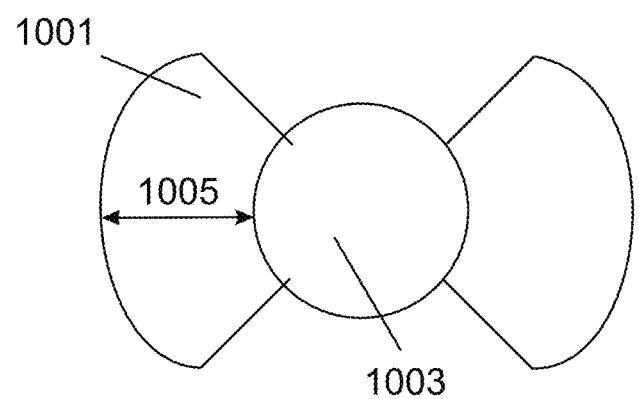
Figure 9A:
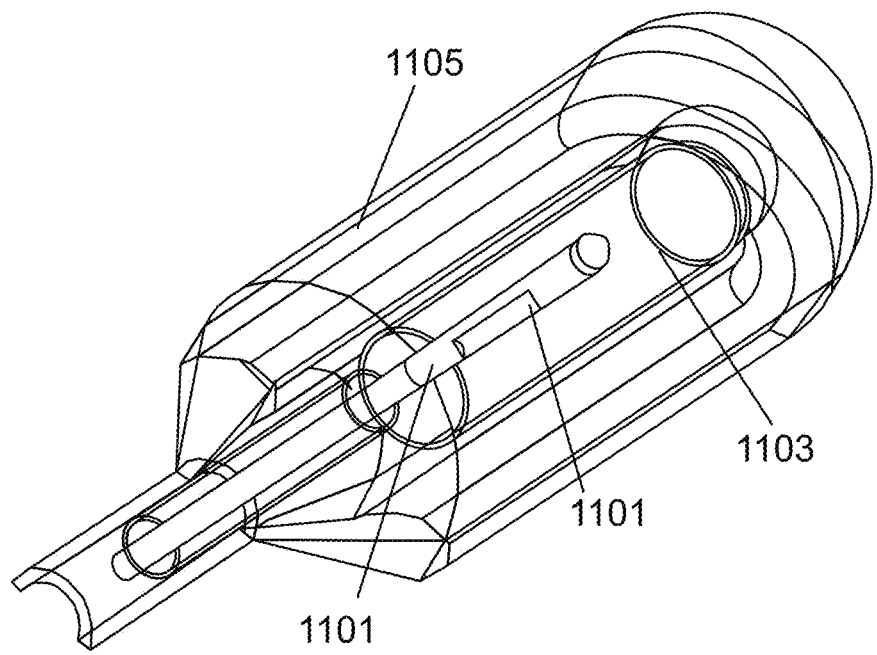
Figure 9B:
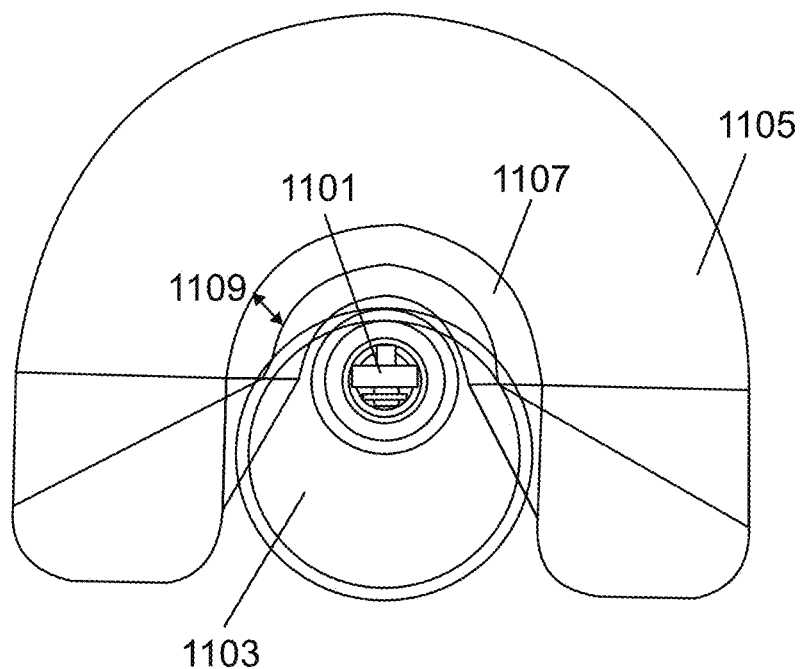
Figure 10:
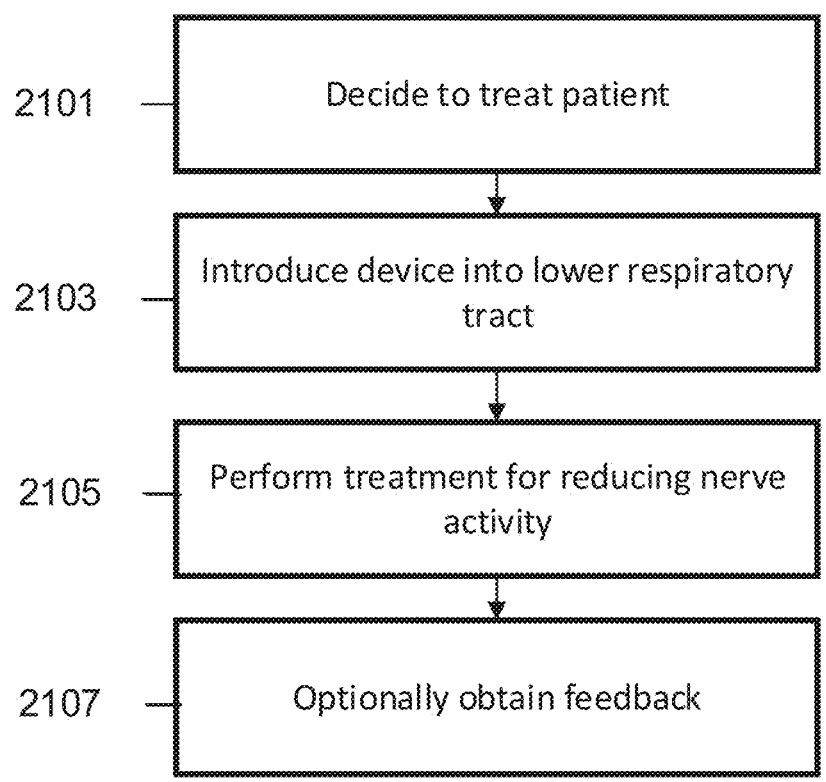
Figure 11:
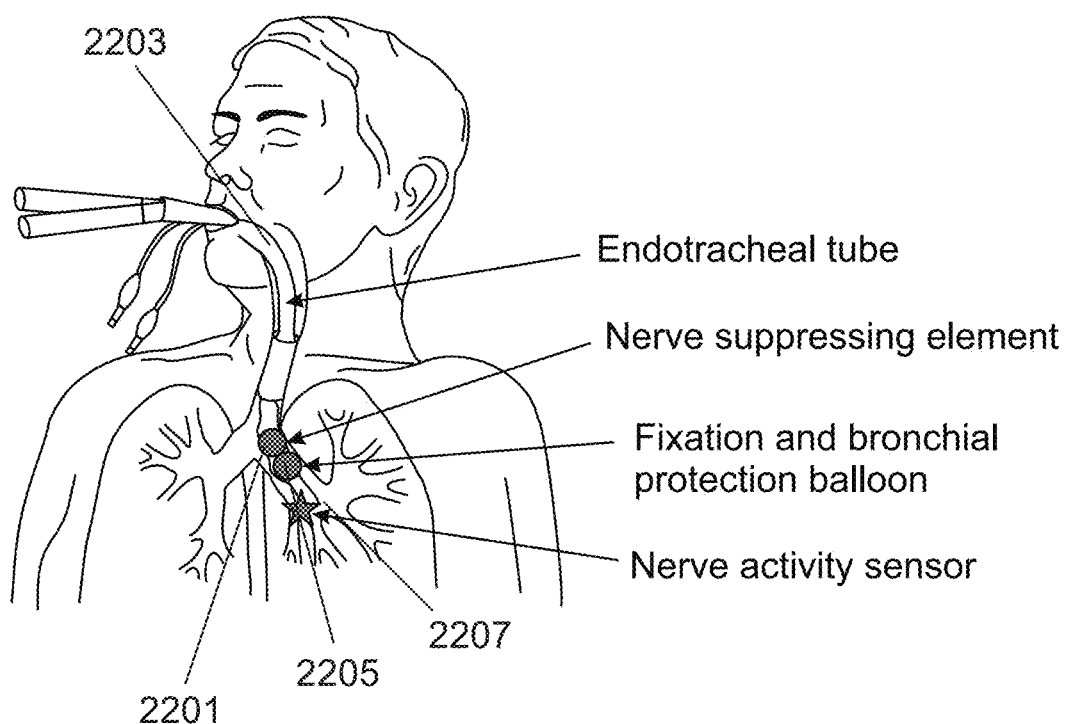
Figure 12:
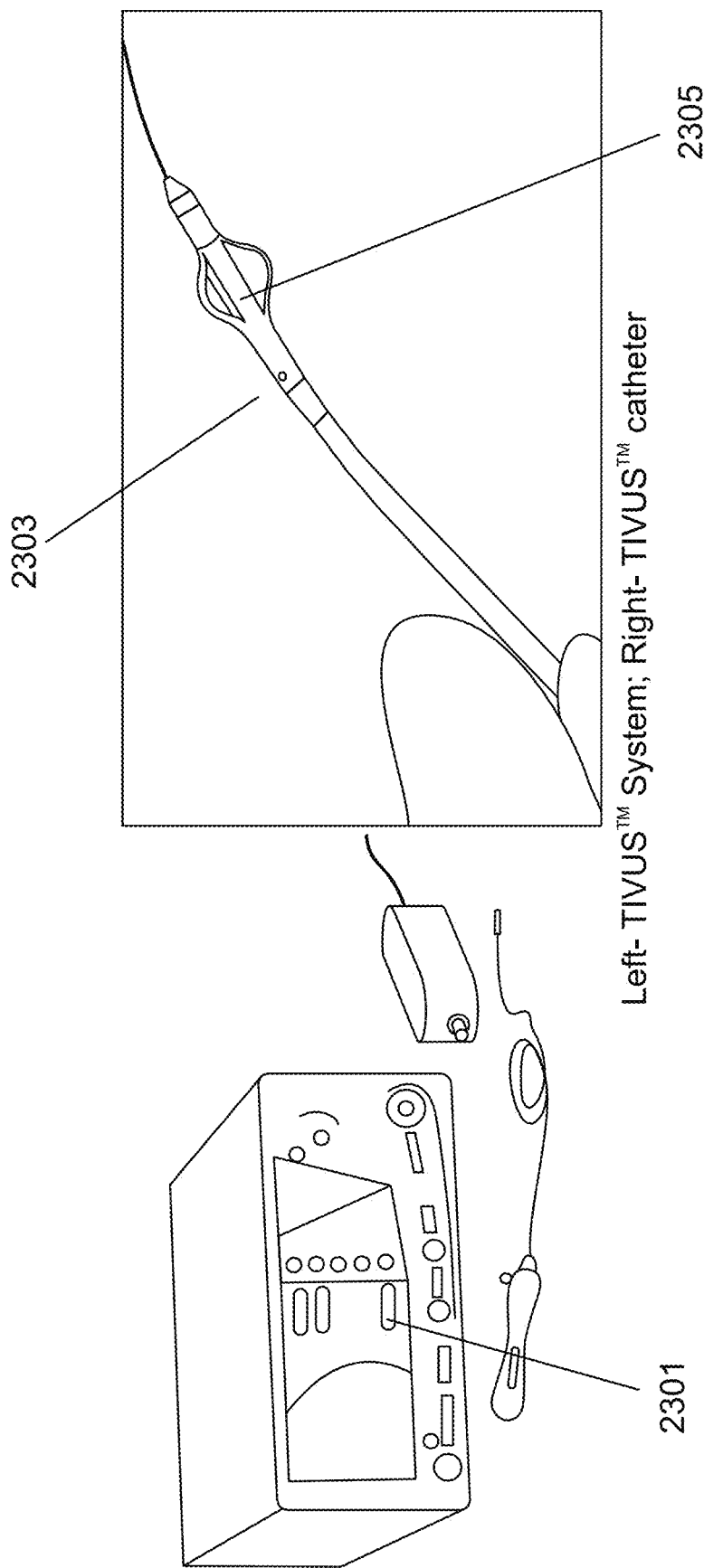
Figure 13A:
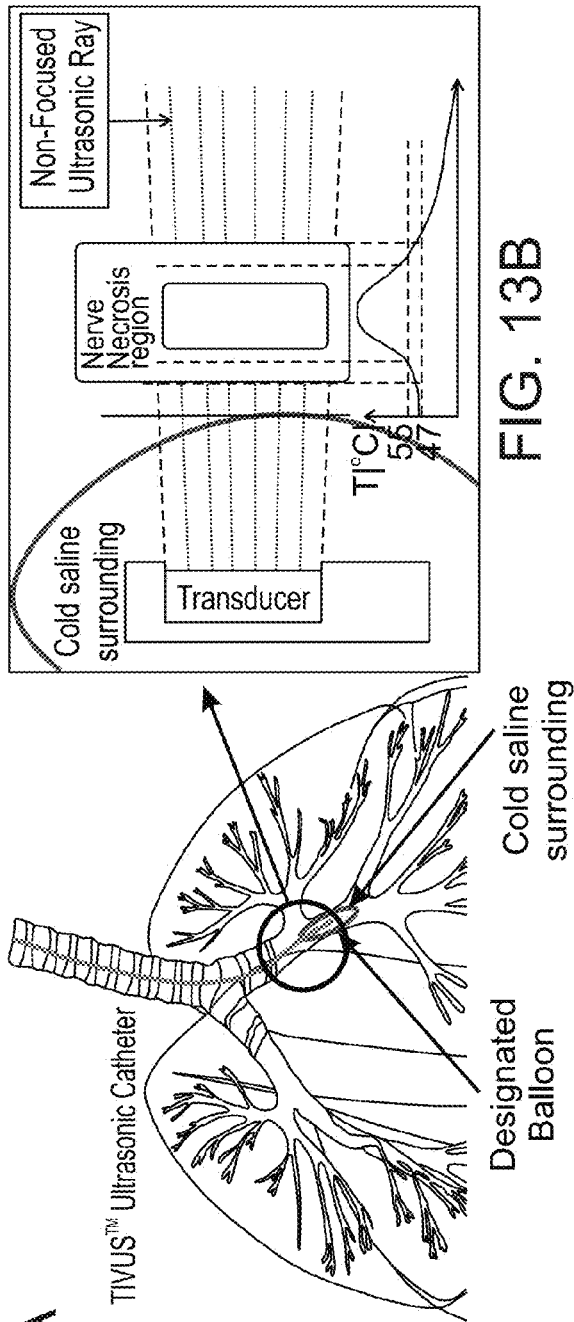
Figure 13B:
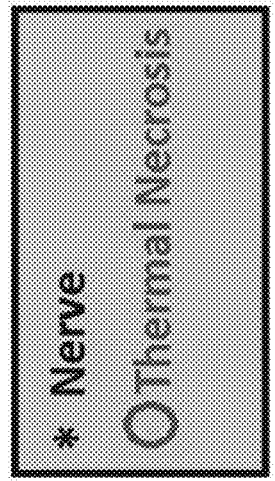
Figure 13C:
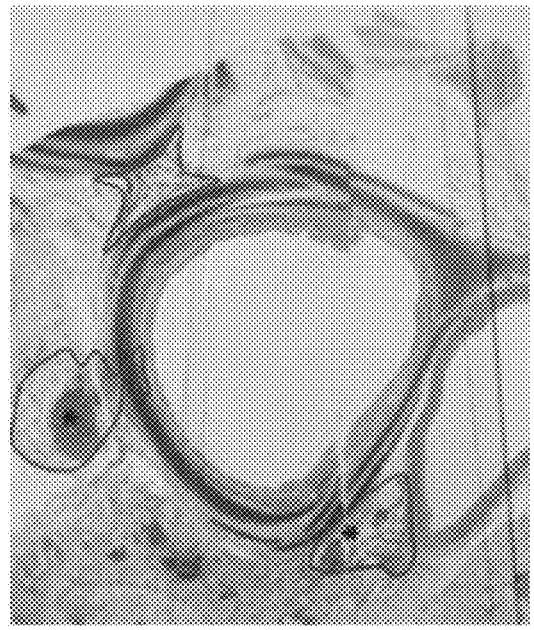
Figure 14A:
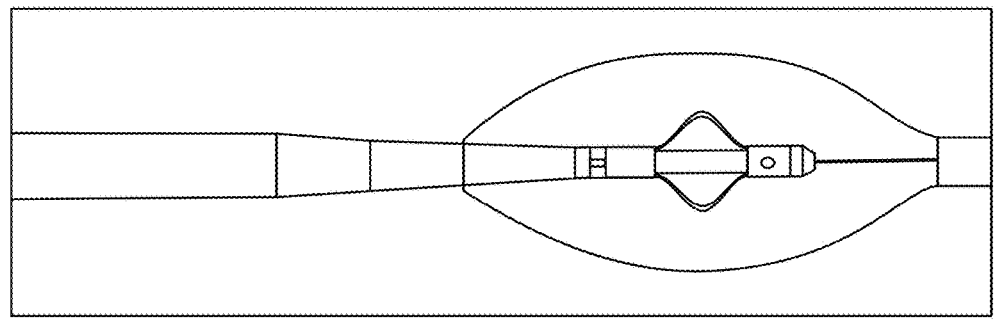
Figure 14B:
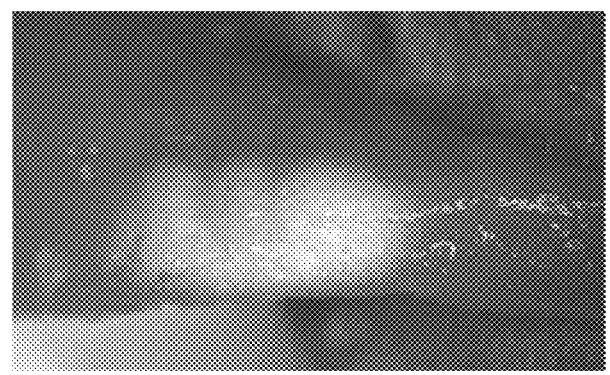
Figure 14C:
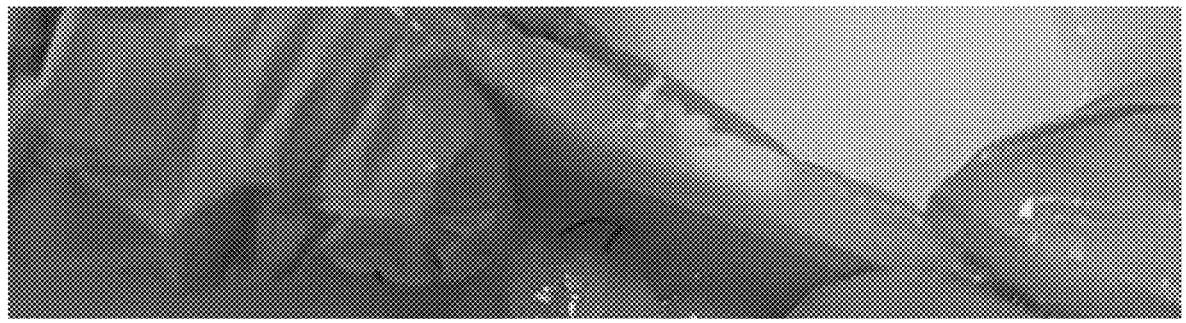
Figure 15:
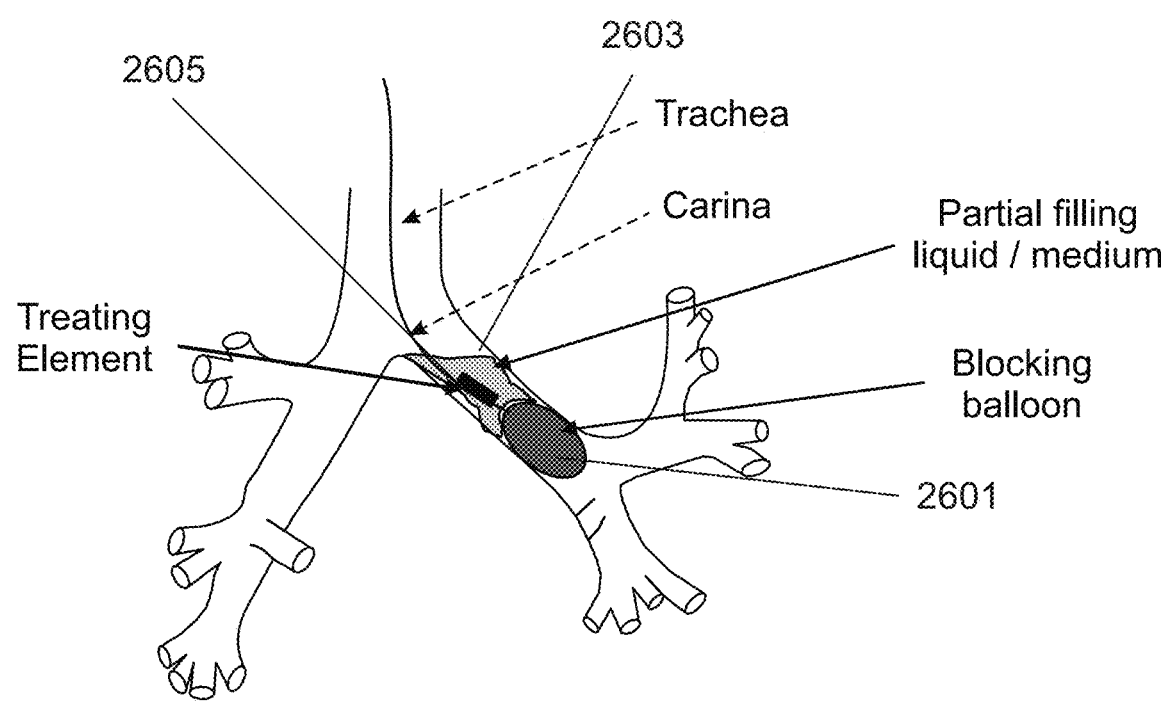
Figure 18A:
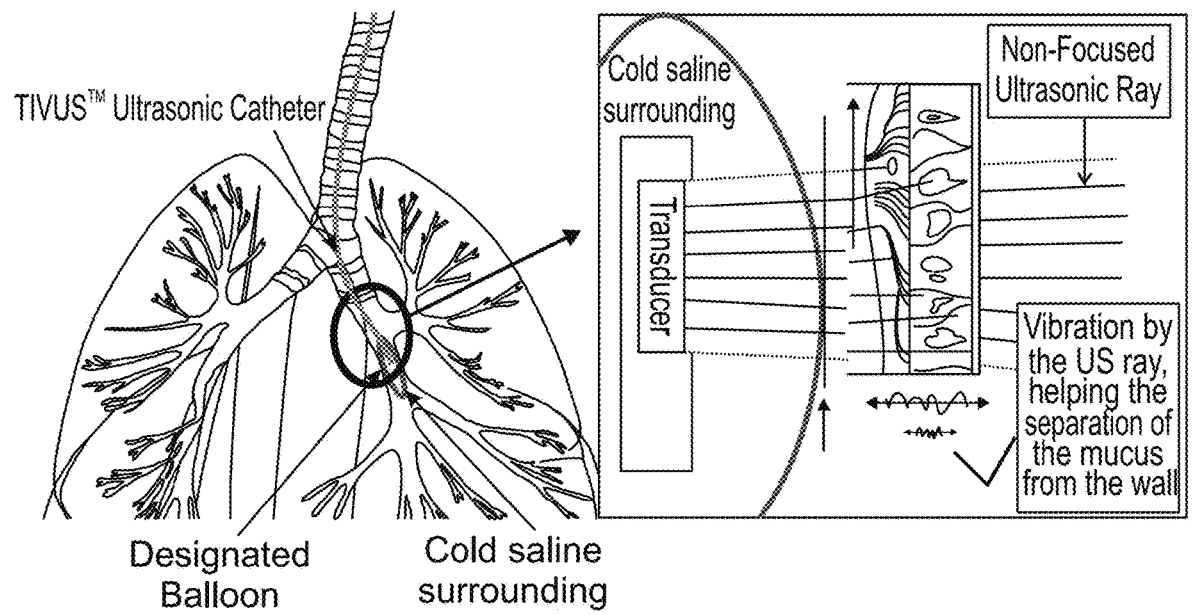
Figure 18B:
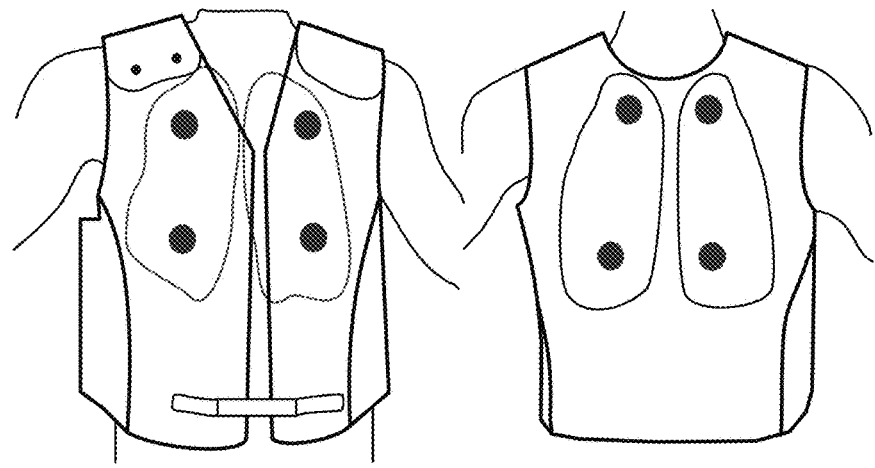
Figure 19A:
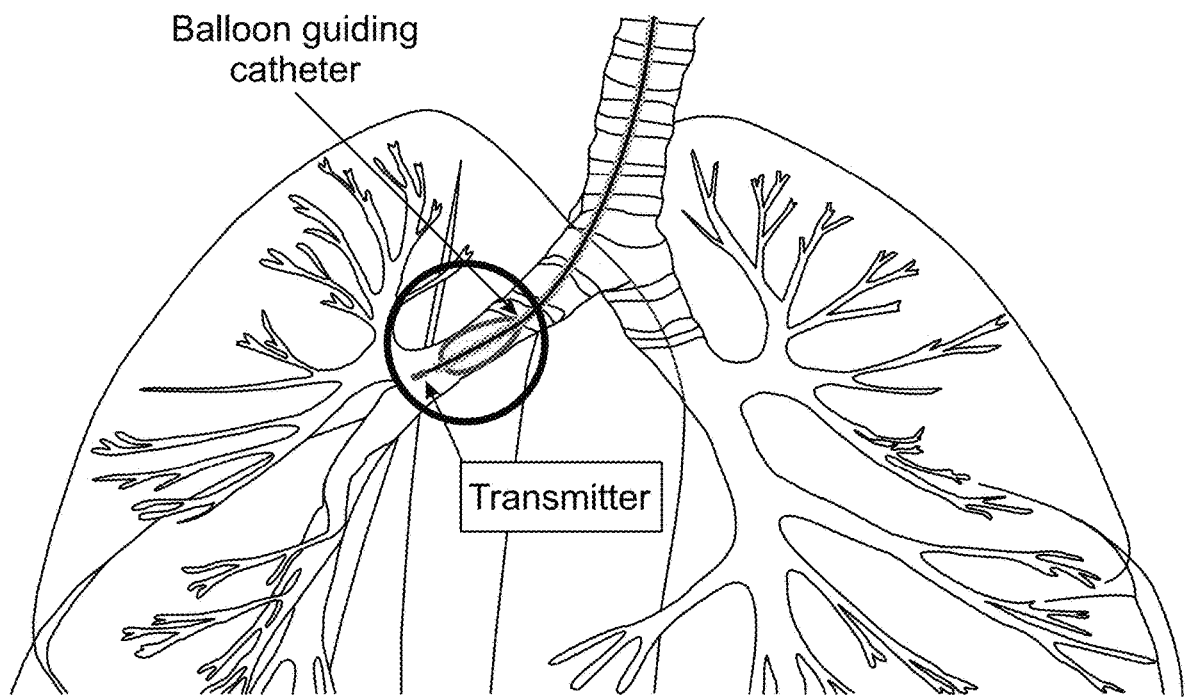
Figure 19B:
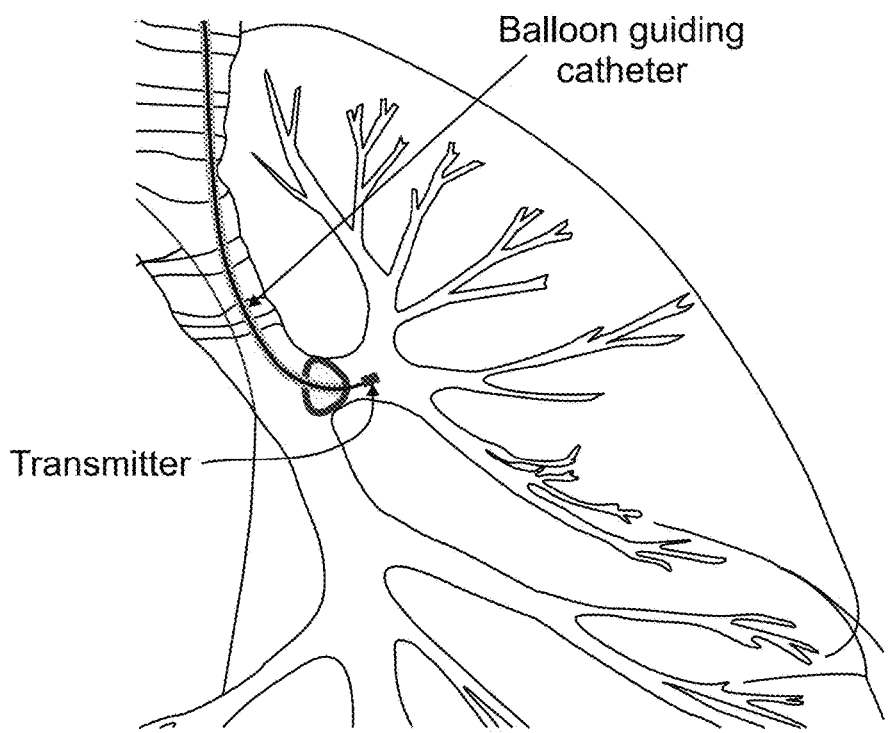
Figure 20A:
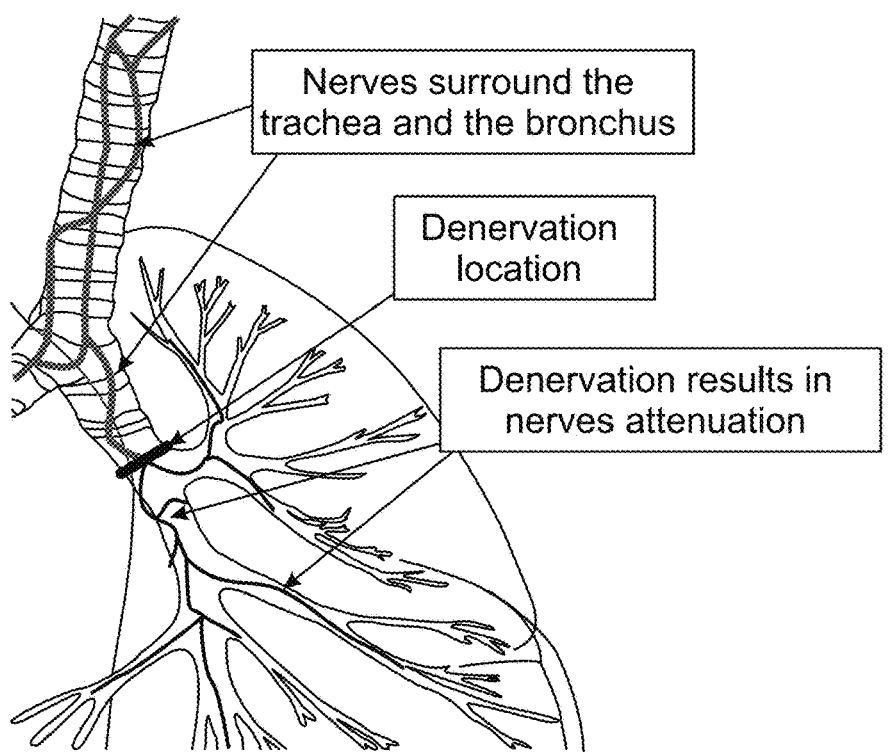
Figure 20B:
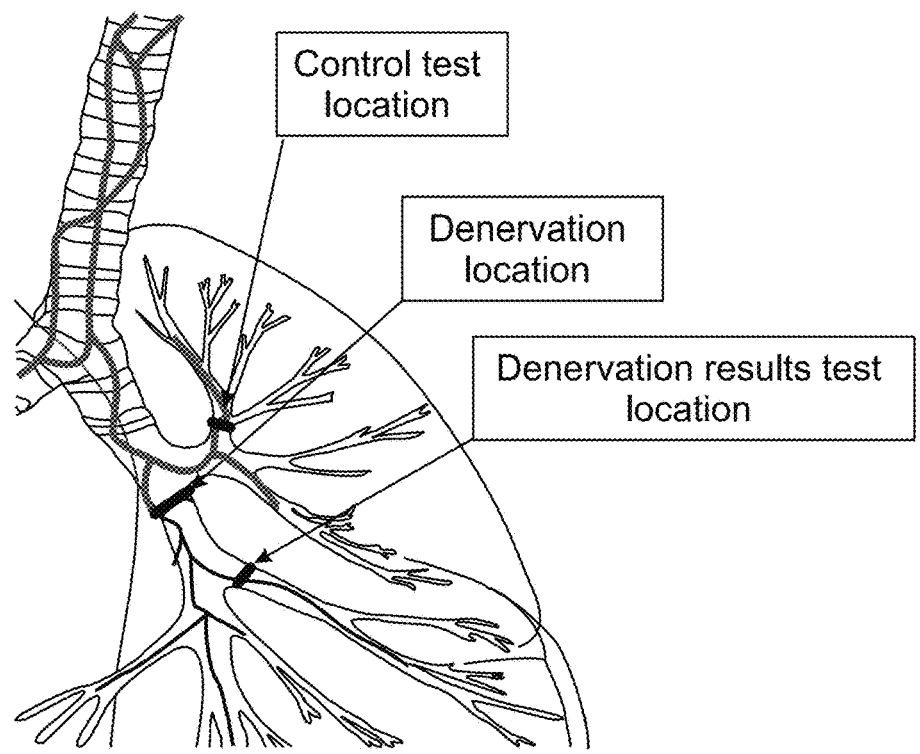
Figure 21:
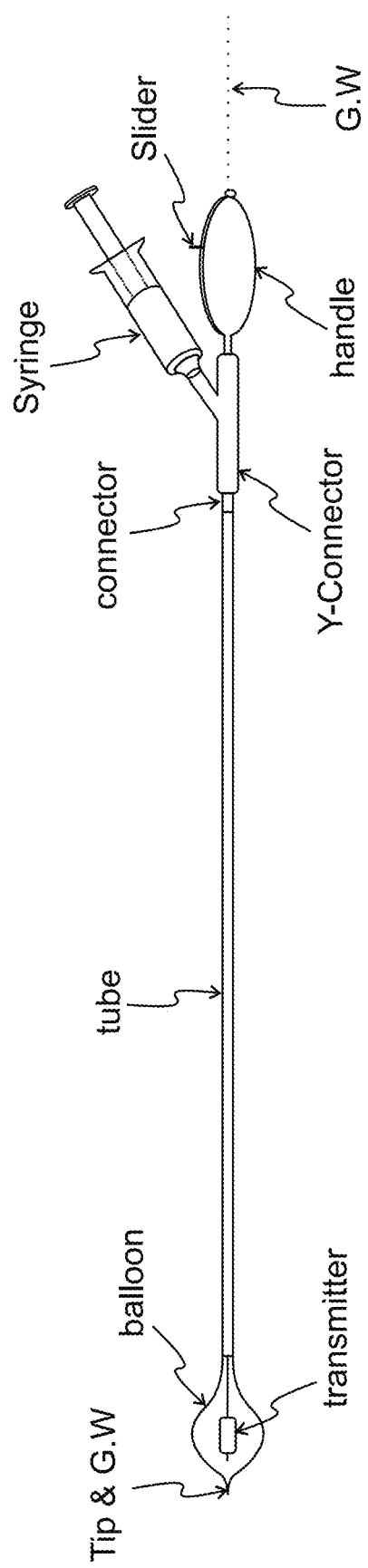
Figure 22:
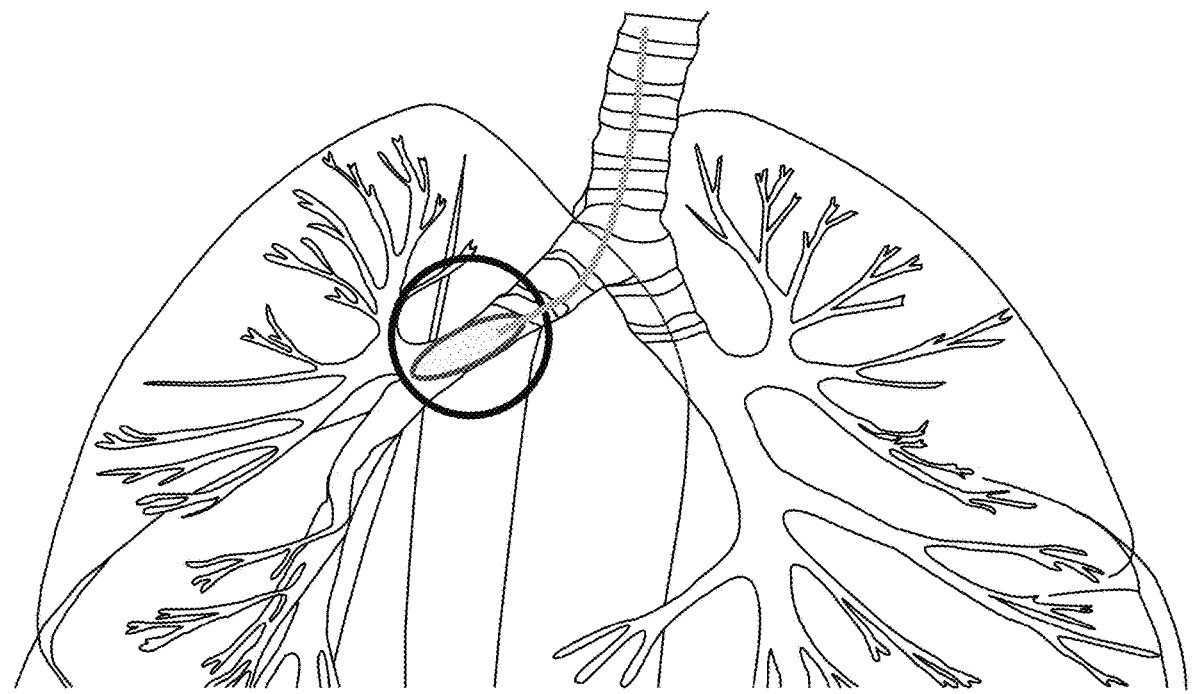
Figure 23:
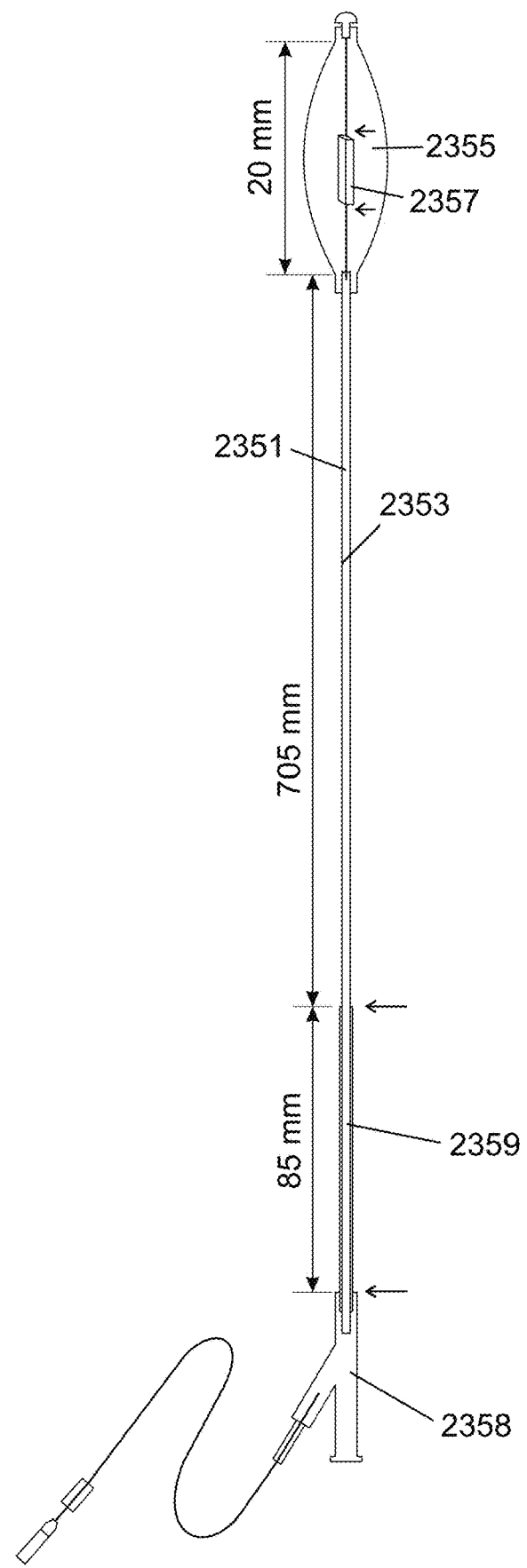
Figure 24A:
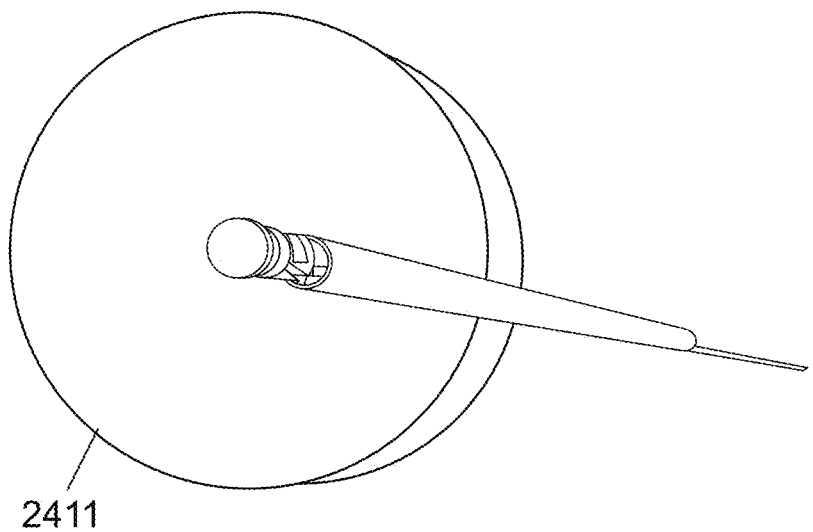
Figure 24B:
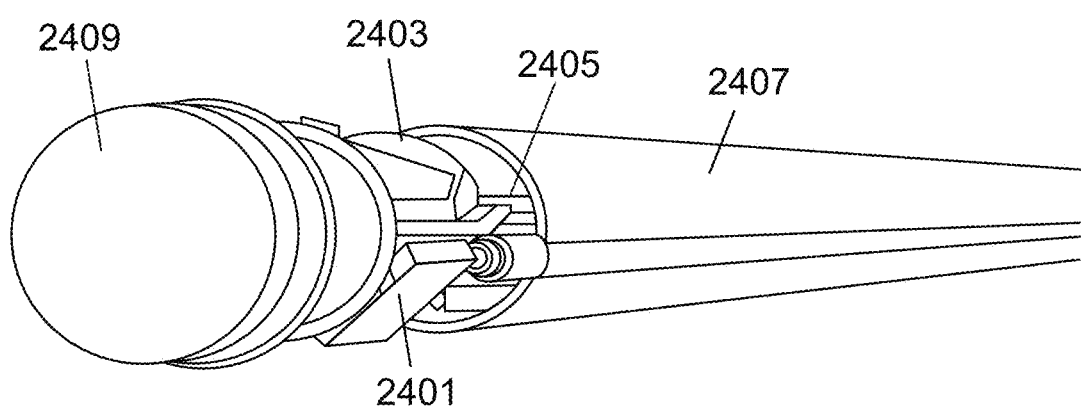
Figure 25A:
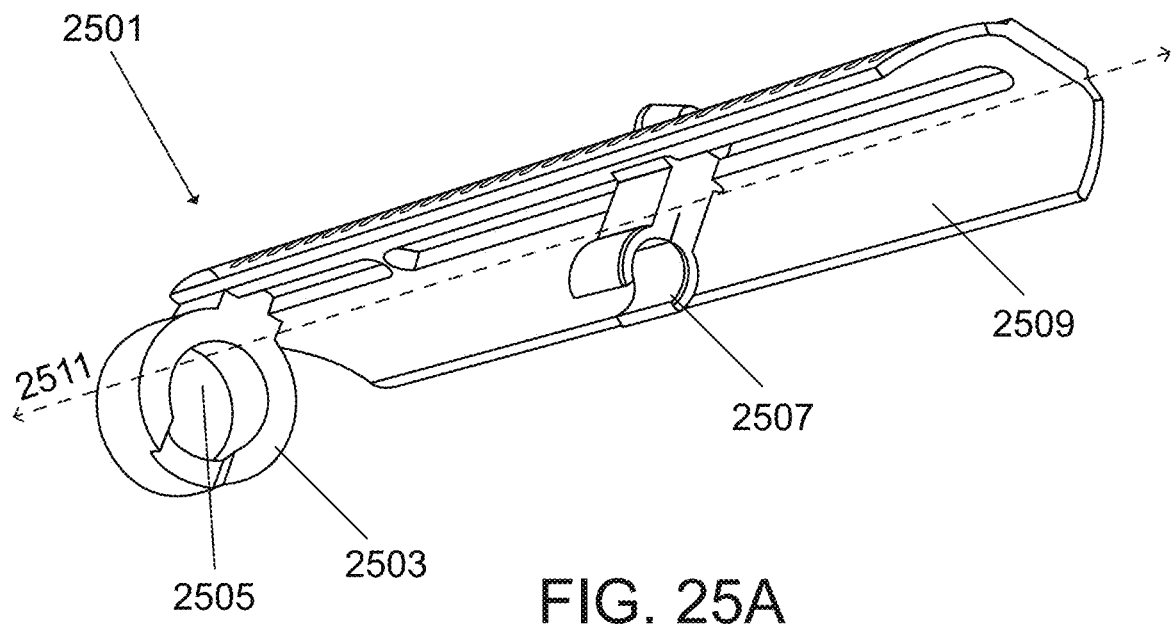
Figure 25B:
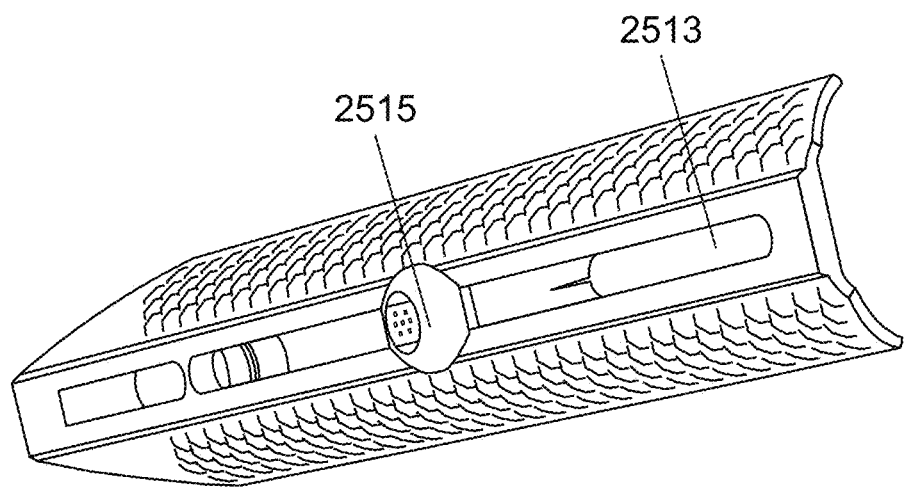
Figure 26:
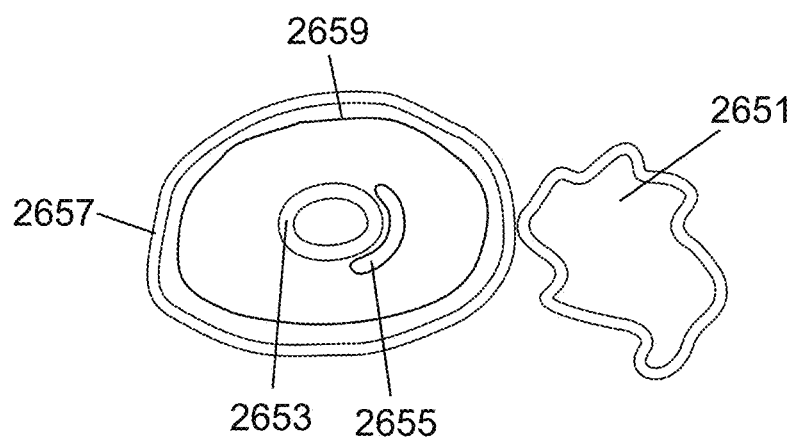
Figure 27A:
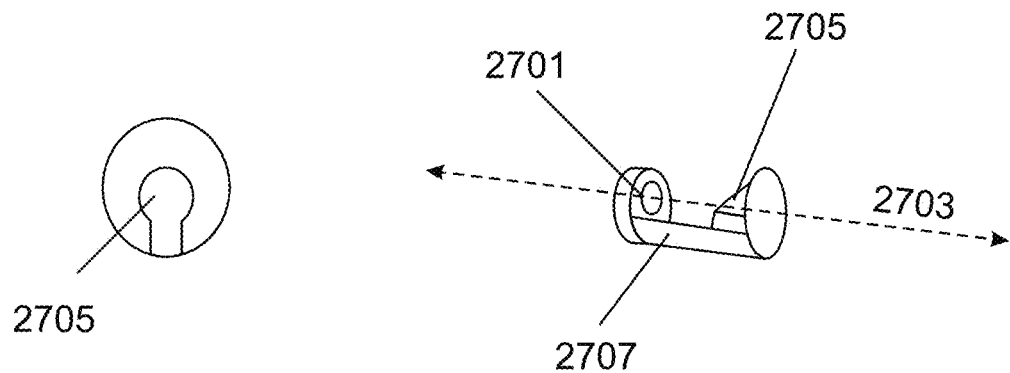
Figure 27B:
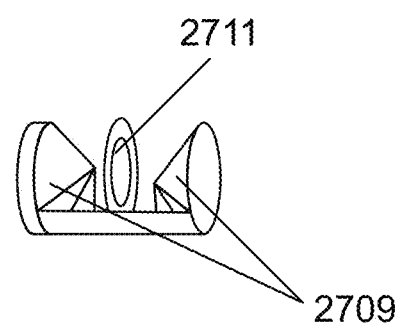
Figure 28A:
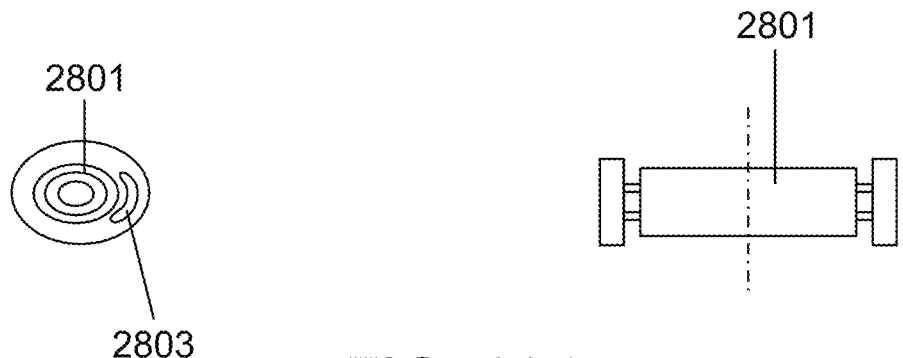
Figure 28B:
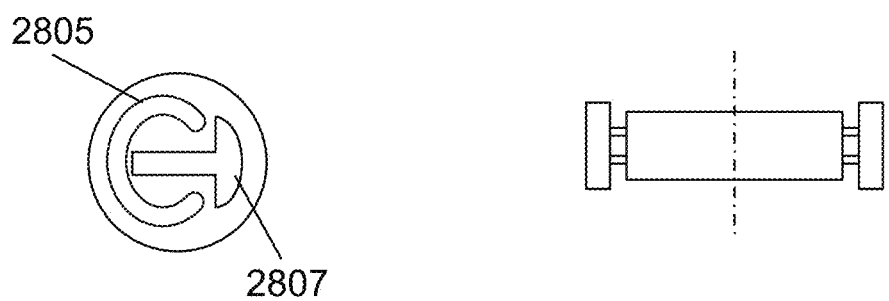
Figure 30:
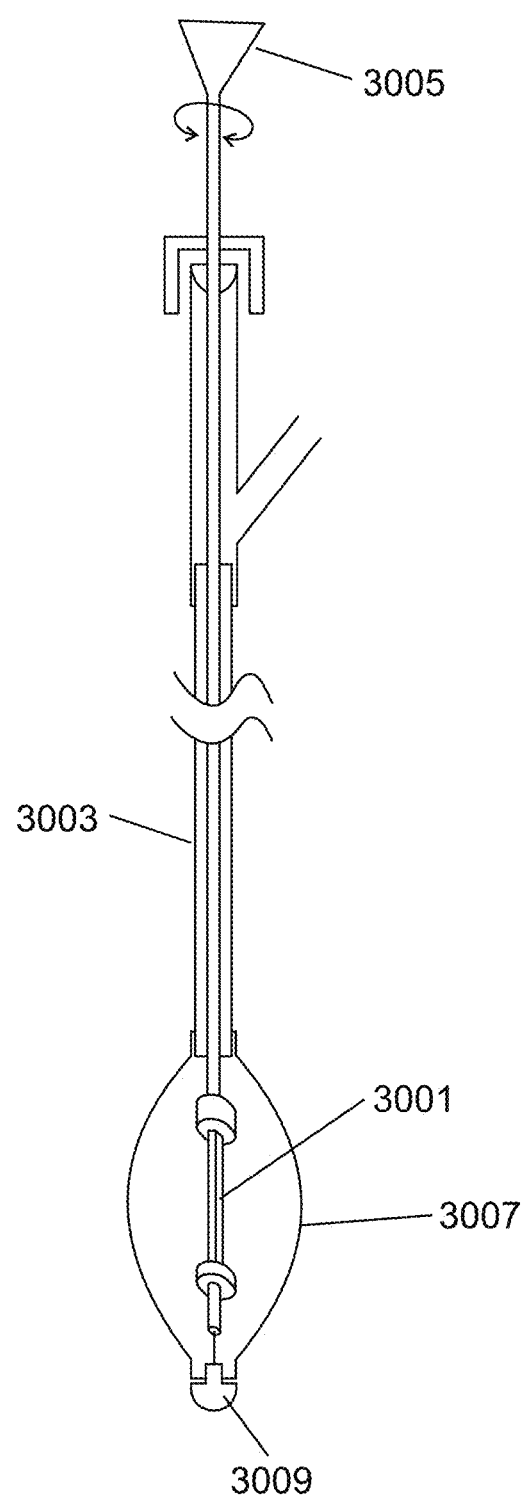
Figure 31:
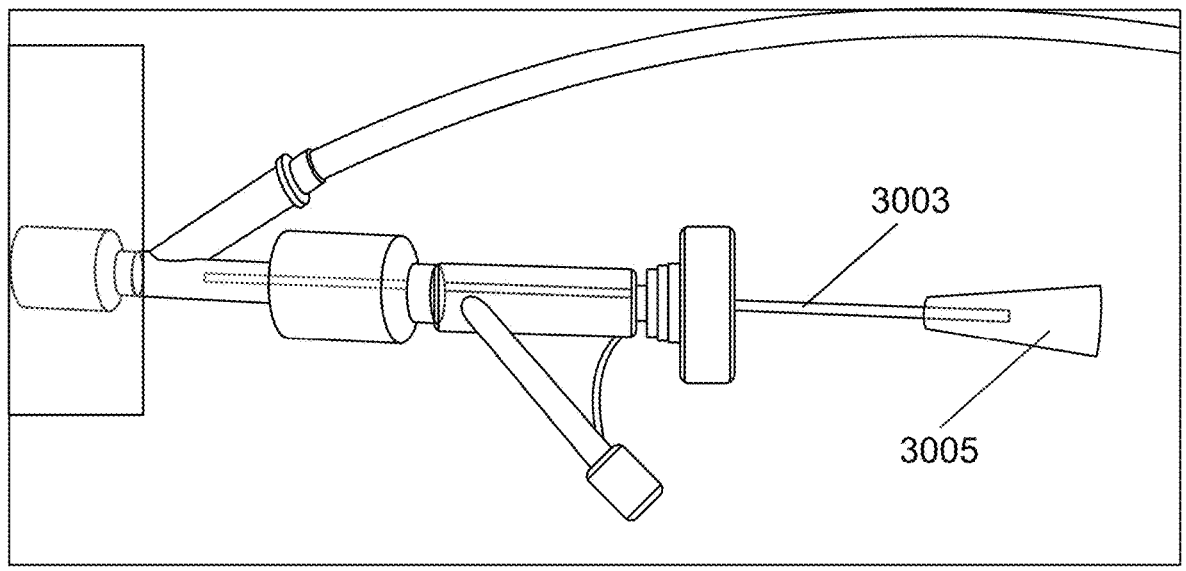
Figure 32:
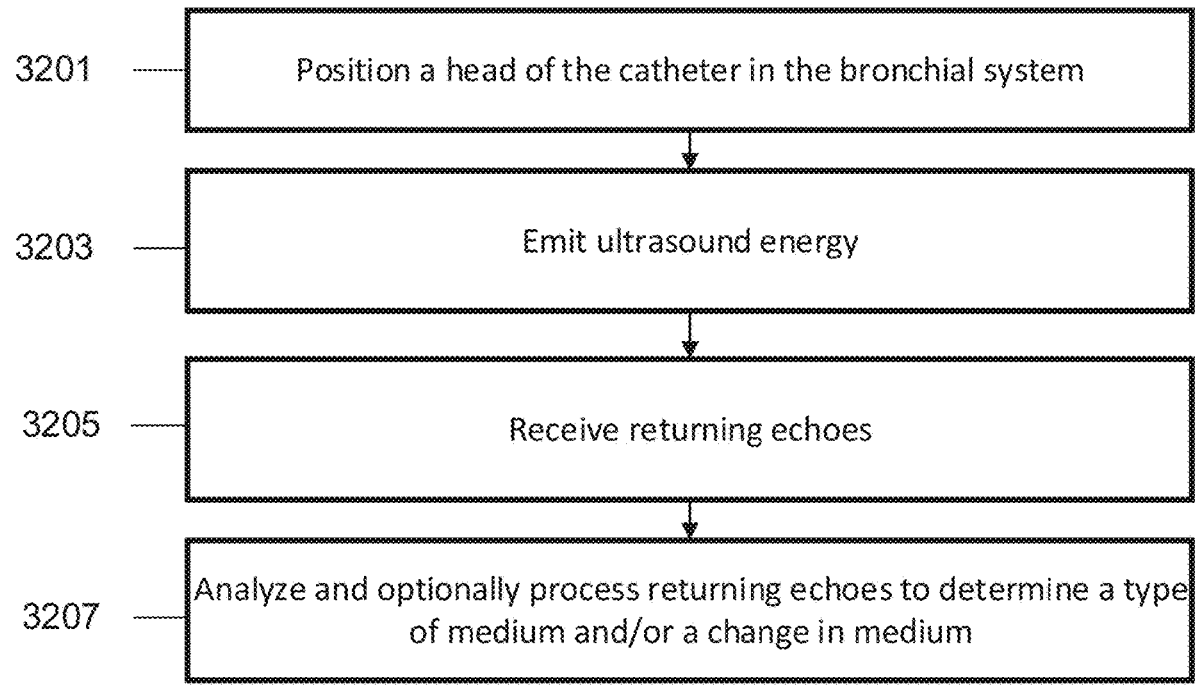

FIGS. 6A, 6B, 6C, 6D1, 6D2, 6E1, 6E2, 6F1 and 6F2 are various configurations of an ultrasonic catheter device, according to some embodiments of the invention;

FIG. 7 is a flowchart of a method for treating nerves by positioning an ultrasonic device in the trachea, according to some embodiments of the invention;

FIGS. 8A-8B show an ultrasonic catheter equipped with one or more balloons, according to some embodiments of the invention;

FIGS. 9A-9B shows an ultrasonic catheter equipped with a multiple balloon assembly for providing heating and/or cooling fluid circulation, according to some embodiments of the invention;

FIG. 10 is a flowchart of a general method for reducing parasympathetic nerve activity for the treatment of a respiratory syndrome, according to some embodiments;

FIG. 11 schematically illustrates introducing of a nerve suppressing element through an endotracheal tube, according to some embodiments;

FIG. 12 shows a system configured for ultrasound denervation from within the trachea and/or from within the bronchus, according to some embodiments;

FIGS. 13A-13C illustrate a treatment scheme using an energy emitting catheter inserted into the bronchus, according to some embodiments, and an example of a histopathological result of the treatment;

FIGS. 14A-14C are images of an in-vitro experiment performed to demonstrate the effects of treating from inside the bronchus, according to some embodiments;

FIG. 15 schematically illustrates treatment applied from inside the bronchus, according to some embodiments;

FIGS. 16A-16G demonstrate a setup and results of a denervation study performed in swine, in accordance with some embodiments;

FIGS. 17A-17D are anatomical illustrations showing the target nerves peripheral to the bronchus and/or to the trachea, according to some embodiments;

FIGS. 18A-18B demonstrate an effect of internally (FIG. 18A) and externally (FIG. 18B) applied vibrations on the tissue, according to some embodiments;

FIGS. 19A-19B are examples of a catheter positioned in the bronchi with the aid of an anchoring balloon, according to some embodiments;

FIGS. 20A-20B schematically show locations of nerve denervation, control testing locations and result testing locations along the bronchus, according to some embodiments;

FIG. 21 is a schematic drawing of a catheter comprising a head including an energy transmitter positioned within an inflatable balloon, according to some embodiments;

FIG. 22 is a schematic drawing of a catheter including a cryo-balloon, according to some embodiments;

FIG. 23 is a schematic drawing of an energy emitting catheter for insertion through a bronchoscope working channel, according to some embodiments;

FIGS. 24A-B are enlarged views of a distal catheter portion surrounded by a balloon, according to some embodiments;

FIGS. 25A-B are isometric views of an adapter which couples a proximal portion of a catheter to a bronchoscope working channel, according to some embodiments;

FIG. 26 schematically illustrates shielding which reduces or prevents thermal damage to non-targeted tissues or organs, according to some embodiments;

FIGS. 27A-B schematically illustrate catheter head structures comprising a shield for preventing or reducing thermal damage to non-targeted tissues, according to some embodiments;

FIGS. 28A-B schematically illustrate catheter head structures comprising a shield for preventing or reducing thermal damage to non-targeted tissues;

FIGS. 29A-B schematically illustrate catheter heads configured for emission of energy only towards a limited circumferential region, according to some embodiments;

FIGS. 30 and 31 are a schematic illustration and an image of a catheter comprising proximal handle mechanism for rotating a distal head of the catheter without rotating a balloon which surrounds the catheter head, according to some embodiments;

FIG. 32 is a flowchart of a method for identifying a medium and/or changes in medium according to ultrasound echoes, according to some embodiments; and FIGS. 33-34, 35A-D, 36A-D, 37A-B, 38A-B and 39A-C include details and results of experiments performed by the inventors of this application in swine and sheep models for assessing targeted lung denervation using systems and/or methods for example as described herein, according to some embodiments.

DESCRIPTION OF SPECIFIC EMBODIMENTS OF THE INVENTION

The present invention, in some embodiments thereof, relates to modifying (e.g. reducing) parasympathetic nerve activity in patients suffering from a respiratory syndrome, and more particularly but not exclusively, to the treatment of respiratory syndromes associated with bronchoconstriction and/or increased mucus production.

A broad aspect of some embodiments relates to reducing or eliminating parasympathetic nerve activity of nerves innervating the respiratory tract or portions thereof for improving one or more of the following conditions associated with a respiratory syndrome: bronchoconstriction, increased mucus production and/or increased hyaluronic fluid production, inflammation.

In some embodiments, treatment is applied to patients diagnosed with a respiratory condition such as bronchitis, chronic bronchitis, COPD, pneumonia, lung inflammation. In some embodiments, treatment is applied to patients whose respiratory condition was caused by and/or affected by a viral infection, such as SARS, SARS-2, MER, COVID-19, SARS-CoV-2 and/or other virus. In some embodiments, treatment is applied to patients receiving respiratory support (e.g. ventilation and/or oxygen supplements) and/or to patients which are expected to need respiratory support. In some cases, suppressing of the parasympathetic nerve activity may lead to reduced mucus production, increased oxygenation, dilating of the bronchus, weaker inflammatory response, and/or other improvements of a diseased respiratory tract.

In some embodiments, treatment is applied to COPD patients diagnosed with COVID-19 virus. In this group of patients, denervation may be especially advantageous as it may reduce the need for external ventilation and/or reduce the ventilation time required. In some embodiments, treatment is applied in addition to provision of one or more medicaments to the patient. Such medication may include, for example, mucus reducing and/or blocking substances, medication which reduces bronchoconstriction, and/or medication. In some cases, the provided medication has a synergistic effect with the denervation treatment.

An aspect of some embodiments relates to suppressing nerve activity via a device introduced into the lumen of the trachea or the bronchi (e.g. the left and/or right bronchus; the primary and/or secondary bronchus), the device comprising at least one nerve suppressing element. In some embodiments, the device is shaped and sized for insertion through an endotracheal tube.

In some embodiments, the nerve suppressing element is configured for emitting energy suitable to damage nerves and/or block nerve conduction of nerves located peripherally to the lumen and/or otherwise surrounding the lumen. In an example, the nerve suppressing element is configured to emit ultrasound energy suitable to thermally damage the nerves (for example, via an ultrasonic transducer). In an example, the nerve suppressing element comprises an RF electrode. In some cases, ultrasound emission may be advantageous over RF, for example because RF involves direct heating which may cause sparks or ignition in the presence of oxygen, while ultrasound energy does not impose that risk.

In some embodiments, the energy-emitting nerve suppressing element is positioned within and/or surrounded by a fluid medium, for example by insertion of the element into a fluid filled balloon. Optionally, energy emitted by the nerve suppressing element is transferred via the fluid medium. In some embodiments, the fluid medium acts to cool the tissue of the inner wall of the lumen in which the element is positioned (e.g. the inner wall of the trachea and/or bronchus (bronchial epithelium layer)). In some embodiments, the fluid medium acts to cool the surface of the element, such as to prevent overheating. In some embodiments, a temperature of the fluid medium (for example, saline inside the balloon) is selected in accordance with parameters of the emitted energy, for example, use of a cooler fluid may provide for emitting energy of a higher intensity while preventing or reducing damage to the inner walls of the lumen being treated since the walls are sufficiently cooled by the fluid.

Additionally or alternatively to using a fluid filled balloon, a blocking element is inserted into the lumen, and the lumen is then partially filled with fluid (e.g. saline or water), which acts as a transfer medium.

In some embodiments, the nerve suppressing element is configured to generate a magnetic and/or electric field suitable to damage nerves and/or block nerve conduction of nerves located peripherally to the lumen and/or otherwise surrounding the lumen.

In some embodiments, the nerve suppressing element is configured to cool the nerve tissue to an extent sufficient to reduce or eliminate neural activity, for example using cryotherapy (e.g. via a cryo-balloon).

In some embodiments, treatment is applied towards one or more rotational positions along the lumen circumference. In some embodiments, treatment is applied at a plurality of axial positions along the lumen long axis. In an example, when positioning the nerve suppressing element in the bronchi, the element is positioned at a distance of between 1 cm-10 cm from the bifurcation of the trachea.

In some embodiments, the nerve suppressing element is positioned and/or maintained in position during treatment with the aid of an anchoring element, such as an anchoring balloon. Optionally, the anchoring balloon is inflated in a location proximal to the location from which treatment is applied, along the lumen (e.g. along the bronchus lumen or the trachea lumen).

In some embodiments, treatment involves injecting and/or releasing one or more substances which affect nerve structure and/or function, for example: medications, alcohol or phenol (neurolytic blockers), toxins such as botulinum toxin, tetanus toxin and tetrodotoxin, irritants, proteolytic enzymes, polyacid and/or other.

In some embodiments, one or more effects of the treatment are sensed and/or monitored, optionally in real time. In some embodiments the device comprises one more sensors configured to detect direct and/or indirect changes caused by the treatment. For example, assessing the humidity level and/or a change in humidity in the lungs, for example using humidity sensors; for example, assessing nerve activity distally to the treated location, for example by using an electrode and/or an antenna to detect and/or measure a magnetic field of the nerves conductivity.

In some embodiments, effects of treatment are assessed by triggering a physiological response, such as by triggering a Hering-Breuer reflex of the lungs. In an example, a change in the reflex (e.g. delay, non-occurrence, reduced strength and/or other) is indicative of the extent of nerve damage produced by denervation.

In some embodiments, treatment is applied such that flow or air to the lungs is maintained. For example, in some embodiments, the catheter device and/or a balloon used with the device include one or more conduits for passing air through. Air flow to the treated patient may be provided actively (e.g. via ventilation means) and/or passively (e.g. via natural inhalation). In some embodiments, the catheter comprises an opening and/or a conduit for shunting air into the lung opposite the side being treated. (For example, when treatment is applied from the left bronchus, a conduit and/or an opening in the catheter may be provided for allowing flow of air to the right bronchus and into the right lung).

In some embodiments, treatment is applied to different areas of the respiratory tract, for example based on their functionality and/or diseased state. In an example, an area which exhibits obstruction (optionally more than other areas) is treated. Optionally, assessment of the different areas is performed using a bronchoscope.

An aspect of some embodiments relates to internal and/or external applying of vibration (such as acoustic vibration) which accelerates mucus separation from tissue and/or thinning of mucus. In some embodiments, an oscillating element (such as an oscillating ultrasound transducer used for denervation) inserted into the bronchi and/or the trachea produces vibration in the lumen walls and/or surrounding tissue. Optionally, the oscillations are transferred to the tissue via a balloon surrounding the element. Additionally or alternatively, vibrations are applied to the chest wall from externally to the body, such as via a vibrating wearable device, e.g. a vest. Potential advantages of applying internal and/or external vibration may include: accelerating the separation of mucus from tissue which it is adhered to; thinning of the mucus and/or a reduction in mucus viscosity (optionally due to a rise in temperature in the oscillated tissue); breaking of mucus chunks; reduction in mucus accumulation; promoting movement of mucus towards the upper respiratory tract, from which the mucus exits naturally (such as by coughing) and/or removed, e.g. by suction. In some embodiments, vibration (such as high frequency chest wall oscillation) is applied to patients suffering from conditions such as CF, COPD, Covid-19 patients whose condition has deteriorated and their blood oxygenation has decreased, SARS patients, bronchiectasis and/or other respiratory conditions. In such patients, clearing the airway from mucus may help prevent infection and/or reduce inflammation.

Some embodiments relate to positioning an ultrasonic catheter in the pulmonary tract, trachea and/or bronchi for targeting and treating nerve tissue by thermally damaging the nerve tissue. In some embodiments, treating comprises emitting ultrasound energy, such as non-focused ultrasound, for modifying nerve function. In some embodiments, activity of one or more nerves, nerve segments, nerve plexuses and/or other nerve tissue is reduced or eliminated. In some embodiments, treatment comprises ablating nerve tissue and causing a damage sufficient to prevent regeneration of the tissue.

Some embodiments relate to selectively treating nerve tissue, using at least one ultrasonic transceiver to characterize tissue and using that same transceiver to emit energy for treating targeted tissue. In some embodiments, selective treatment comprises causing damage to selected nerves without causing substantial damage to non-targeted tissue, such as surrounding organs and/or other nerve tissue. In some embodiments, characterizing tissue comprises identifying one or more organs such as the lungs, trachea, lymph, bronchi or others. In some embodiments, organs are identified based on their echo signal reflection. Optionally, the reflected signals are received by the one or more ultrasonic transceivers of the catheter device, and are analyzed to determine the organ type and/or the relative distance of the organ from the lumen from which treatment is applied, such as the trachea lumen and/or the bronchi lumen. In some embodiments, the ultrasonic transceivers are activated at a first energy profile to identify and/or characterize tissue, and at a second energy profile to treat tissue. Optionally, non-targeted tissue is identified. Additionally or alternatively, targeted tissue is identified.

In some embodiments, selective treatment comprises differentiating between nerves during treatment, for example by producing a predetermined temperature profile in the treated nerves. Optionally, the predetermined temperature profile is obtained by emission of ultrasound energy at a selected profile, suitable to heat the nerves to a desired temperature or range of temperatures. In an example, differentiating between nerves comprises causing damage only to nerves that are not coated by myelin by producing a first temperature range, and causing damage to both coated and non-coated nerves by producing a second temperature range.

In some embodiments, selective treatment comprises emitting energy for thermally damaging nerve tissue without causing substantial damage to the wall of the lumen from which treatment is applied, for example the wall of the bronchus. Optionally, damage to the wall is reduced by keeping the one or more ultrasonic transceivers away from the wall, for example by using a distancing device.

Selective treatment is pursued, in some embodiments, by activating one or more transceivers to emit energy towards a selected direction, and/or deactivating one or more transceivers to reduce or prevent emission in one or more other directions.

Some embodiments relate to feedback based treatment of nerves innervating the respiratory tract or portions thereof. In some embodiments, treatment is continued and/or modified based on one or more measurements of physiological control parameters, including local parameters such as, for example, bronchi diameter, and/or systemic parameters, which may be a byproduct of denervation, including, for example, heart rate, respiratory volume, and/or other physiological parameters. In some embodiments, the physiological parameters are measured internally to the body. Additionally or alternatively, the physiological parameters are measured externally to the body. In some embodiments, the ultrasonic catheter is configured to acquire the one or more physiological parameters. In an example, a physiological parameter such as a diameter of a lumen is estimated by analyzing echo signals reflected by the walls of the lumen and received by the one or more transceivers of the catheter device. In some embodiments, the physiological parameter is acquired by stimulating the nervous system to evoke an observable physiological response and/or a chain of responses, one or more of which are detectable and optionally measureable.

In some embodiments, a measurement of the physiological parameter acquired before treatment is compared to a measurement of the same physiological parameter following treatment, to determine treatment effectiveness. For example, an increase in diameter of the bronchus above a certain threshold, measured following treatment, may indicate that the treatment was effective.

In some embodiments, immediate feedback is provided, and treatment is modified and/or ceased based on the feedback. In an example, immediate feedback comprises assessing dilation of the bronchi, which may be observed shortly after denervation. In another example, immediate feedback comprises assessing blood pressure.

Some embodiments relate to an ultrasonic catheter structure and/or to elements used with the catheter that are suitable for reducing unwanted movement of the catheter, and more specifically movement of at least a distal portion of the catheter.

In some embodiments, a structure of the catheter shaft is selected to damp movement. In some embodiments, one or more locations along the catheter shaft are structured to provide a full or partial axial decoupling between axial segments of the catheter, for example so that movement of the head at a distal end of the device is least affected by movement of a more proximal portion of the catheter shaft. Additionally or alternatively, the catheter is anchored to a certain location, to prevent or reduce movement of the catheter relative to the tissue, for example during emission of ultrasound. Optionally, a small range of movement is permitted, such as movement to an extent which does not affect targeting. Additionally or alternatively, a "working frame" is provided, and the catheter is maneuvered within the working frame. Additionally or alternatively, movement of the catheter is synchronized with movement of the targeted tissue, for example by anchoring the catheter to a structure that moves in a similar pattern to the targeted tissue.

In some embodiments, at least a head of the catheter, comprising the one or more ultrasonic transceivers, is positioned and/or oriented within the lumen from which treatment is applied at a predetermined location. Optionally, positioning of the catheter and/or directing of the ultrasonic beam is selected based on one or more of: a distance from the tissue to be treated, a distance from the lumen wall, a position along the length of the lumen, parameters of the ultrasonic beam emitted by the transceivers (e.g. beam shape), and/or others. In some embodiments, positioning of the catheter and/or directing of the beam is performed by delivering the catheter over a pre-shaped guide wire, for example a spiral guide wire or a guide wire curved to a substantial Z shape. A potential advantage of the spiral configuration may include setting an advancement path for the catheter in which at any point along the path, at least the catheter head is maintained at a selected distance from the lumen wall, for example in proximity to the lumen wall. Optionally, the catheter is positioned a distance between 0.1 mm to 20 mm from the lumen wall. Optionally, the distance is selected in accordance with the intensity applied, for example a distance ranging between 0.1 mm to 5 mm, 5 mm-10 mm, 15 mm-20 mm or intermediate, larger or smaller distance ranges are used with an intensity between 20 W/cm^2 to 80 W/cm^2. In some embodiments, the spiral diameter (i.e. a diameter of a loop) is selected according to the lumen diameter. Additionally or alternatively, the spiral diameter is selected according to the catheter diameter, for example a diameter of the catheter head. In some embodiments, a similar effect to delivering the catheter over a helical structure may be obtained by delivering the catheter over the Z-shaped wire, and rotating the wire. Optionally, the catheter is introduced over the wire to a position in which the catheter head is proximal to the curved portion of the wire. Alternatively, the catheter is introduced over the wire to a position in which the catheter head is distal to the curved portion of the wire. Another potential advantage of the spiral and/or Z-shaped configurations (and/or any other configurations suitable to position the catheter away from the center of the lumen and in proximity to the walls) may include facilitating treating the lumen circumferentially. Optionally, when applying circumferential treatment by delivering the catheter over a curved guide wire, the curvature of the wire can be selected to obtain a certain orientation of the transceivers at the head of the catheter, for example positioning a transceiver such that a longer dimension of the transceiver (for example being a rectangular transceiver) extends at an angle relative to a longitudinal axis of the lumen.

Some embodiments relate to applying treatment by positioning an ultrasonic catheter comprising a temperature-controlled balloon arrangement in an air filled lumen, such as the trachea. In some embodiments hot and/or cold fluid is circulated within the balloons. In some embodiments, circulation of fluid at selected temperatures or ranges thereof is controlled to shape the treated tissue area, such as to obtain a predetermined depth of the effective field in the tissue. In an example, cold fluid is circulated within an inner balloon which surrounds the catheter, for cooling the one or more transceivers, and warm fluid is circulated within an external balloon, for enhancing the thermal heating effect of the emitted energy and potentially increasing a depth of the effective ultrasound field in the tissue. In an embodiment, cool fluid flows over the transceivers to cool them, thereby absorbing the excess heat and warming up. Optionally, the same warmed-up fluid or a partial volume thereof is then circulated to the outer balloon, to enhance the thermal heating effect.

In some embodiments, the balloons do not surround a full circumference of the catheter head. Optionally, the balloons are arranged relative to the catheter head and/or relative to each other such that an emitting surface of the one or more transceivers is exposed to face the tissue. Alternatively, the balloons are positioned to cover at least a portion of the transceiver's surface.

In some embodiments, a balloon arrangement comprises a plurality of balloons which are effective to push the catheter away from the wall of the trachea.

In some embodiments, the fluid in the one or more balloons acts as a transferring medium for carrying the ultrasound energy from the transceivers to the trachea wall.

In some embodiments, the catheter, even when the one or more balloons are inflated, does not block the airway. Optionally, a total cross sectional diameter of the catheter with the inflated balloons is at least 5%, at least 10%, at least 20% or intermediate, larger or smaller percentages smaller than a cross sectional diameter of the trachea.

In some embodiments, one or more organs and/or tissues are identified for selectively applying the treatment from the air filled lumen, such as the trachea. In an example, cartilage rings of the trachea are identified, and energy is emitted in between the rings. Optionally, the cartilage rings are identified by processing of echo signals reflected from the rings and received by the transceivers of the catheter.

It is noted that various conditions may be treated using the methods and/or devices described herein, including, for example, one or more of pulmonary hypertension, pulmonary arterial hypertension (PAH), asthma, chronic obstructive pulmonary disease (COPD), mesothelioma, heart failure, atrial fibrillation, sleep apnea, insulin resistance and/or other conditions directly or indirectly associated with nerve activity.

In some embodiments, nerve activity along the bronchial tree is reduced. In some examples, a reduction in nerve activity may reduce the number of binding sites (receptors) in the respiratory tract due to the reduced para-sympathetic nerve output. In some examples, the receptors binding affinity is reduced, thereby reducing a likelihood of binding pathogens, for example viruses such as, but not limited to, COVID-19, SARS, SARS2 pathogens. In an example, receptors affected by the denervation treatment include ACE2 receptors and/or other acetylcholine binding sites in the bronchus area. In some embodiments, a reduction in the number of receptors and/or a reduction in the receptors binding affinity is a result of a reduced risk of symptomatic infection, associated with a reduced constriction of the airways and reduced mucus production, for example as further described herein.

An aspect of some embodiments relates to reducing or preventing thermal damage to non-target tissue by shielding the non-target tissue from energy emitted by a denervation device. In some embodiments, a catheter head comprises a plurality of energy emitting transducers (e.g. ultrasound transducers) and a physical shield located radially outwardly to at least a portion of the transducer(s), the shield configured to block or reduce energy emitted by the transducer(s) from being transferred to non-target tissue. In an example, in use, the catheter is introduced into the bronchus. Before emission of energy for denervation of the nerves surrounding the bronchus, the catheter is rotationally oriented such that the shield is positioned between the transducer(s) and non-target tissue such as the esophagus, the spinal cord, the vagal nerve, and/or other tissue or organs.

In some embodiments, the shield is arc-shaped at its cross section. In some embodiments, the shield comprises an axial length (thickness) at least as long as an axial length of the transducer(s). In some embodiments, the arc shaped shield extends about 20%, 30%, 40% or intermediate, longer or shorter percentage of a perimeter of the catheter head.

In some embodiments, the shield is configured to absorb the energy emitted by the catheter transducer(s). Additionally or alternatively, the shield is configured to reflect the energy emitted by the catheter transducer(s). In some embodiments, the shield is configured and positioned so that energy does not penetrate through it.

In some embodiments, a position of the shield is measured or estimated to determine if the shield is located at a suitable anatomical location to protect non-target tissue. In some embodiments, the shield position is determined visually through the bronchoscope and/or using imaging modalities.

In some embodiments, a relative position of non-target tissue such as the esophagus is assessed using ultrasonic echoes (for example using methods as described herein), and the shield is positioned according to the results of the measurement.

In some embodiments, the shield is integrally connected to the catheter head, for example attached to the chassis of the catheter. Additionally or alternatively, the shield is connected to the balloon, e.g. mounted onto an inner wall and/or an outer wall of the balloon.

Alternatively, in some embodiments, the shield is a separate component. Optionally, the shield is configured to be coupled to the catheter head before and/or during insertion to the body.

Additionally or alternatively to shielding the non-target tissue from the energy, parameters of the emitted energy may be selected so that a depth of the effective field is shorter than a distance between the transducer(s) and the non-target tissue, so that the energy does not reach or only partially reaches the non-target tissue, without thermally damaging it. Optionally, by reducing one or more parameter values such as an intensity level of the emitted energy, a duration of the emitted energy, a depth of the effective field can be reduced (shortened).

Additionally or alternatively, the catheter head comprises a non-circumferential arrangement of transducers, for example comprising a single transducer or two transducers, which can be selectively positioned (rotated) to emit energy only towards target tissue, avoiding emission towards non-target tissue such as the esophagus.

An aspect of some embodiments relates to identifying a medium and/or a change in medium using ultrasound echoes received by the catheter. In some embodiments, ultrasound energy is emitted by the one or more transducers of the catheter, the energy having parameters different from energy parameters used during denervation. Optionally, the ultrasound energy is emitted in pulses having a high intensity and/or a short duration.

In some embodiments, echo signals returning following the emission are received by the transducers, and are analyzed and optionally processed. In some embodiments, a change from one medium to another and/or a type of medium is identified, for example: blood, saline, air, soft tissue, bone tissue, cartilage, and/or other mediums. In an example, an air cavity is identified, allowing for example to determine a location and/or position of the esophagus (which is air-filled) relative to the emitting transducer(s). Optionally, upon identifying a relative position and/or location of the esophagus, it is possible to reduce or avoid, such as during denervation, emission of thermally-damaging energy towards the direction of the esophagus.

An aspect of some embodiments relates to an adaptor for coupling a proximal portion of a catheter (e.g. a handle of a catheter) to a proximal opening of a working channel of an endoscope (e.g. a bronchoscope) through which the catheter is inserted. In some embodiments, the adaptor comprises at least two couplers, a first coupler shaped and sized to hermetically fit onto a proximal opening of the working channel, and a second coupler shaped and sized to receive or hold the catheter proximal portion. In some embodiments, the adaptor provides for manual manipulation of the catheter to move the catheter relative to the working channel (for example, to move at least a distal portion of catheter). For example, the second coupler is attached to a slidable knob configured to be moved along a length of the adaptor body, producing axial movement (advancement or retraction) of the catheter inside the working channel; for example, rotation of the adaptor body produces rotation (e.g. roll) of the catheter. Optionally, the adaptor is connected to the bronchoscope in a coupling that enables rotation, such that rotation of the adaptor does not generate rotation of the bronchoscope's working channel, when the catheter inside is rotated.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Examples of Targeted Nerve Tissue

Figure 1:
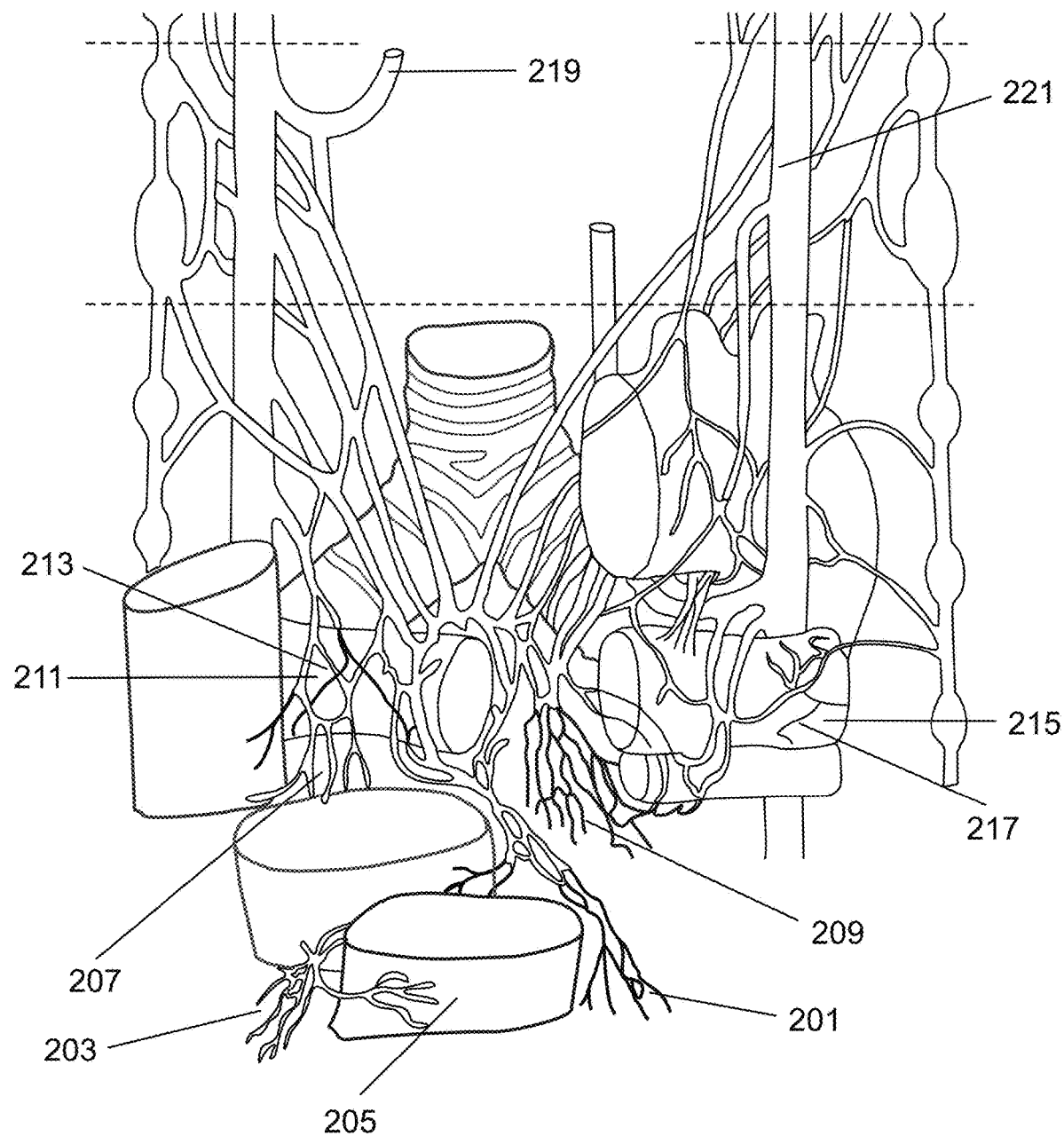

FIG. 1 is a schematic illustration of neural networks and organs in a human thorax. Some of the organs are shown only in part, to enable viewing adjacent organs. The illustration shows the layout of nerves and nerve plexuses, which may be treated by an apparatus for example as described herein. In some embodiments, the targeted nerves may include one or more of, for example, the left coronary plexus 201 and/or the right coronary plexus 203, surrounding the main pulmonary artery 205; the right atrial plexus 207 and/or the left atrial plexus 209; the right pulmonary plexus 211, surrounding the right pulmonary artery 213; and the left pulmonary plexus 215, surrounding the left pulmonary artery 217.

In some embodiments, damage to nerves such as the laryngeal nerve 219 and/or the vagus nerves such as the left vagus nerve 221 is reduced or prevented. Alternatively, in some cases, pulmonary branches of the vagus nerve are treated, for example to modify bronchi activity.

An Ultrasonic Catheter Structure

Figure 2A:
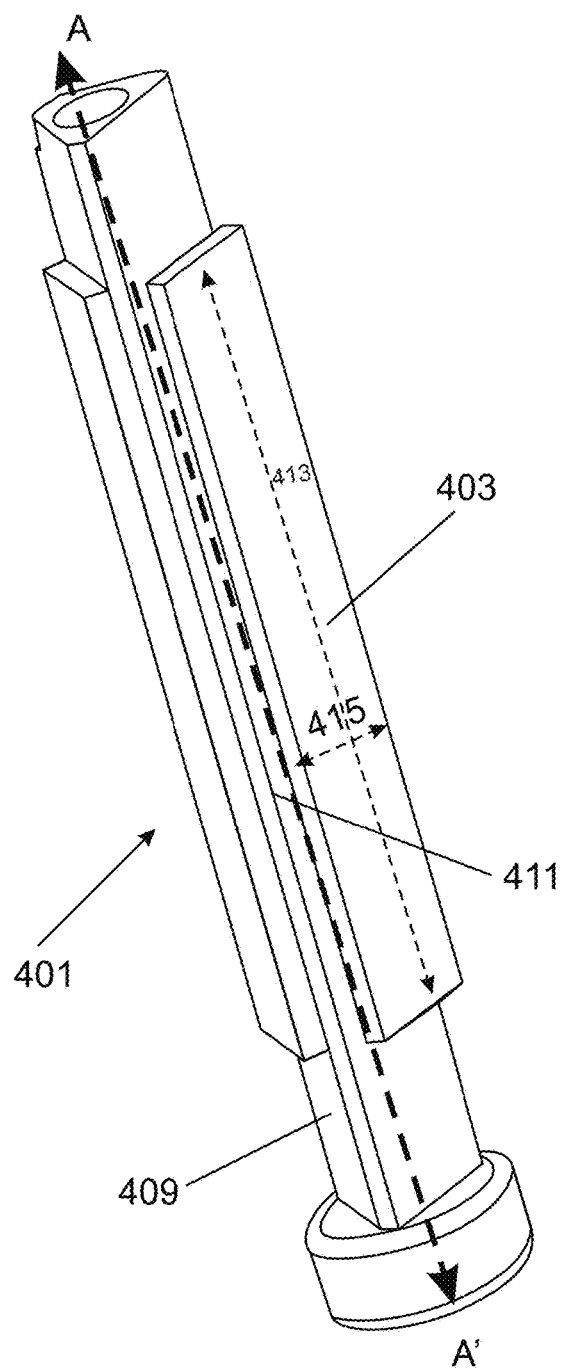
Figure 2B:
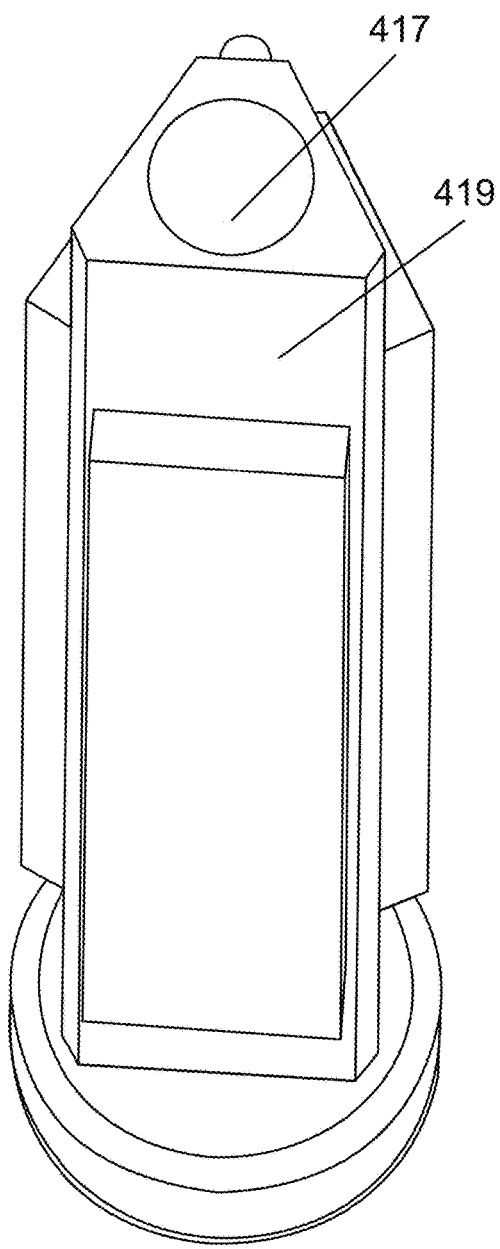

FIGS. 2A-2B are isometric drawings of an exemplary catheter head comprising a plurality of ultrasonic transceivers, according to some embodiments of the invention.

In some embodiments, head 401 comprises one or more piezoelectric transceivers such as transceiver 403, configured for emitting and/or receiving ultrasound by comprising a body vibratable at ultrasonic frequencies. In some embodiments, the transceivers are coupled to a chassis 409 of head

401. Optionally, the transceivers are mounted onto one or more external surfaces of chassis 409.

In some embodiments, catheter head 401 is sized to fit within the bronchus and/or the trachea, the head having a diameter ranging between, for example, 1.3 mm to 4 mm (corresponding with a catheter of between 4-12 F).

In some embodiments, the plurality of transceivers include three transceivers, for example arranged in a triangular configuration. Alternatively, the head comprises a different number of transceivers, such as 2, 4, 5, 6, 8 or intermediate, larger or smaller number. The transceivers may be arranged in various configurations, such as a squared configuration, a hexagonal configuration, an octagonal configuration, or other polygonal configurations. Optionally, the spatial arrangement of the transceivers is configured such that a periphery of head 401 is reduced to a minimum.

In some embodiments, adjacent transceivers are positioned such that a spacing 411 is formed between them. Optionally, spacing 411 provides an electrical and/or thermal isolation between the adjacent transceivers.

In some embodiments, one or more of the transceivers is adapted for emitting ultrasound. In some embodiments, one or more of the transceivers is adapted for receiving ultrasound. In some embodiments, a single transceiver is adapted for both emitting and receiving ultrasound. Optionally, a portion of the transceiver is adapted for emitting ultrasound, and another portion is adapted for receiving ultrasound.

In some embodiments, the one or more transceivers are adapted for receiving echo signals, such as echo signals reflected by walls of the lumen.

In some embodiments, the transceivers are arranged circumferentially. Optionally, the irritated energy is suitable for treating a circumferential region of tissue.

In some embodiments, each of the transceivers faces a different direction than the other transceivers. Optionally, each of the transceivers is configured for emitting and/receiving ultrasound from a different portion of the lumen wall. Additionally or alternatively, two or more of the transceivers face the same portion of the lumen wall. Optionally, the transceivers are arranged so that each of the transceivers covers a sector of the cross section of the lumen, such as a semicircle, a quadrant, a sextant, or a sector having other central angle such as 20 degrees, 40 degrees, 70 degrees.

In some embodiments, for example as shown in this figure, a transceiver is shaped as a rectangle. Exemplary dimensions of a rectangular transceiver include a length 413 ranging between, for example, 3 mm to 8 mm, and a width 415 ranging between 0.8 mm to 2 mm. Optionally, all transceivers are uniformly shaped, for example all transceivers are shaped as rectangles. A potential advantage of uniformly shaped transceivers may include producing a symmetric effective field. Optionally, by having a symmetric field, additional safety is provided, for example in cases where an uncontrolled axial rotation of the catheter head occurs within the lumen. Another potential advantage may include simplifying the manufacturing process. Alternatively, in some embodiments, each of the transceivers comprises a different shape, for example one transceiver shaped as a rectangle, a second transceiver shaped as a trapezoid, etc. Additionally or alternatively, in some embodiments, all transceivers are uniformly shaped with a shape other than a rectangle, such as a trapezoid, a circle, a triangle, or any other shape.

In some embodiments, the transceivers are selected during the assembling of the catheter. Optionally, the transceivers are sorted according to characteristics such as a resonant frequency and/or impedance properties. Optionally, a catheter assembled with pre-sorted transceivers can be operated at a frequency range that is determined according to the resonant frequencies of its transceivers, thereby optionally increasing the efficiency of the catheter.

In some embodiments, the transceivers of a single catheter comprise different resonant frequencies. Optionally, the transceivers are operated independently of one another. Alternatively, two or more of the transceivers are operated together.

In some embodiments, the catheter can be used as a unidirectional catheter, a bidirectional catheter, a triple directional catheter or any multidirectional catheter. Optionally, this is obtained by selectively operating one or more transceivers at an efficiency higher than one or more other transceivers.

In some embodiments, the operating frequency is selected and/or modified so that two opposing transceivers of a catheter (for example transceivers that are furthest apart from each other on a squared shaped catheter) are operated together. The operating frequency may then be modified to sweep between the transceivers and operate a second set of transceivers. A potential advantage of alternating between the transceivers may include reducing overheating of the transceivers, which may occur when a transceiver is activated over time. Optionally, one or more transceivers that are directed towards the target tissue are activated, while one or more transceivers that are directed towards non-target tissue are deactivated.

In some embodiments, the transceivers are operated (e.g. by a controller, for example comprised within a console of the catheter) according to a lookup table. Optionally, the lookup table correlates between an efficiency of each of the transceivers and a certain operating frequency. By operating the transceivers according to the lookup table, various combinations and alternations between the transceivers can be obtained.

In some embodiments, a radially outward facing surface of the one or more transceivers is flat. Additionally or alternatively, one or more transceiver surfaces are concave. Additionally or alternatively, one or more surfaces are convex.

In some embodiments, chassis 409 is formed as an elongated shaft, in this example having a triangular cross section profile. Alternatively, in other embodiments, the chassis may comprise a square profile, a rectangular profile, a circular profile, a hexagonal profile, or an arbitrary profile. Optionally, a cross sectional profile of the chassis corresponds with the transceiver configuration, for example, a triangular configuration of transceivers is mounted (directly or indirectly) onto a triangular chassis.

In some embodiments, chassis 409 is cannulated. Optionally, a lumen 417 (as clearly shown, for example, in FIG. 2B) within the chassis is dimensioned to receive a guide wire. In some embodiments, lumen 417 is sized to receive a pressure measurement device, for example a guide wire comprising one or more pressure sensors. In some embodiments, lumen 417 is sized and/or shaped to receive a guide wire of a predefined curvature, for example a Z-shaped guide wire.

In some embodiments, substances such as saline, cooling fluid, contrast liquid, medication and/or other fluids are delivered through the lumen of chassis 409. In some embodiments, a collapsed balloon is delivered through the lumen of chassis 409, and delivered through the distal tip of the catheter to be inflated within the lumen. Optionally, an inflating substance such as air or saline are passed through the lumen to fill the balloon. In some embodiments, the balloon comprises one or more pressure sensors. Optionally, the one or more sensor are configured on an external wall of the balloon, for example at a distally facing wall, and are used for assessing pressure.

In some embodiments, a radially outward facing surface of chassis 409 such as facet 419 serves as a platform onto which a PCB and/or one or more transceivers can be mounted.

In some embodiments, chassis 409 is formed of an electrically conductive material. Additionally or alternatively, chassis 409 is formed of a thermally conductive material, for transferring heat away from the transceivers. Optionally, chassis 409 is coated by a thermally and/or electrically conductive material. Exemplary materials include metal such as gold or copper. Optionally, various components of the catheter such as electrical wiring are soldered onto a surface of the chassis, and may thereby reduce the need for soldering pads. Optionally, chassis 409 is rigid enough to prevent deformation of the piezoelectric transceivers that are mounted onto it.

In some embodiments, the facets of chassis 409 are evenly distributed with respect to a longitudinal axis AA' of the chassis. For example, each facet of a triangular chassis is positioned at an equal radial distance from longitudinal axis AA'. Optionally, by mounting the transceivers onto facets such as facet 419 of the chassis, the transceivers are aligned with respect to longitudinal axis AA' and/or with respect to each other. Optionally, a radial distance between each transceiver and axis AA' is equal for all peripherally arranged transceivers. Alternatively, the distance varies for different transceivers. A potential advantage of utilizing a periphery of the catheter head for mounting of components such as the transceivers may include a simpler, more reliable manufacturing and assembly process.

In some embodiments, one or more of the transceivers is electrically coupled to a circuit board (not shown in this figure). Optionally, a surface of the PCB opposite the transceiver is mounted onto a chassis 409. Additionally or alternatively, one or more of the transceivers is mounted directly onto chassis 409.

In some embodiments, catheter head 401 is in communication, such as by a wire connection or wireless connection, with an operating console. In some embodiments, the console comprises software for processing the acquired echo signals.

In some embodiments, the console is configured for scanning an impedance of the transceivers and comparing the scanning results to calibrated values, to determine if the catheter is qualified for use.

A Distancing Device of a Catheter

Figure 3A:
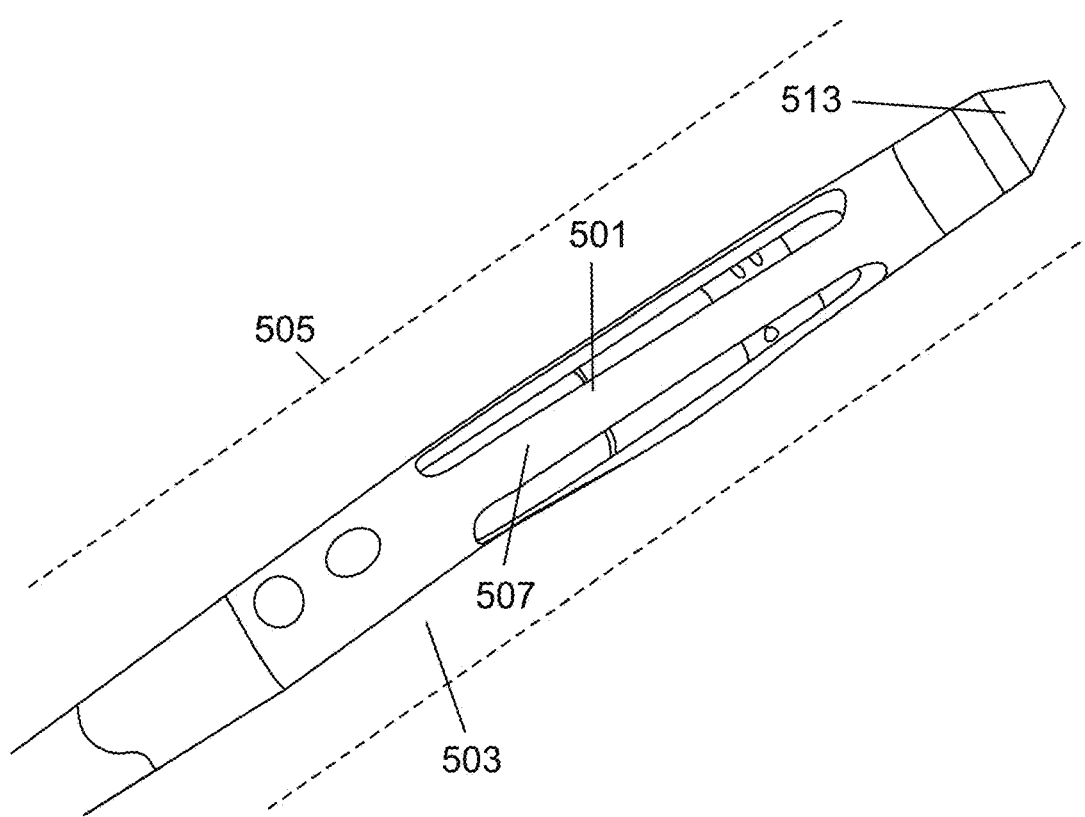
Figure 3B:
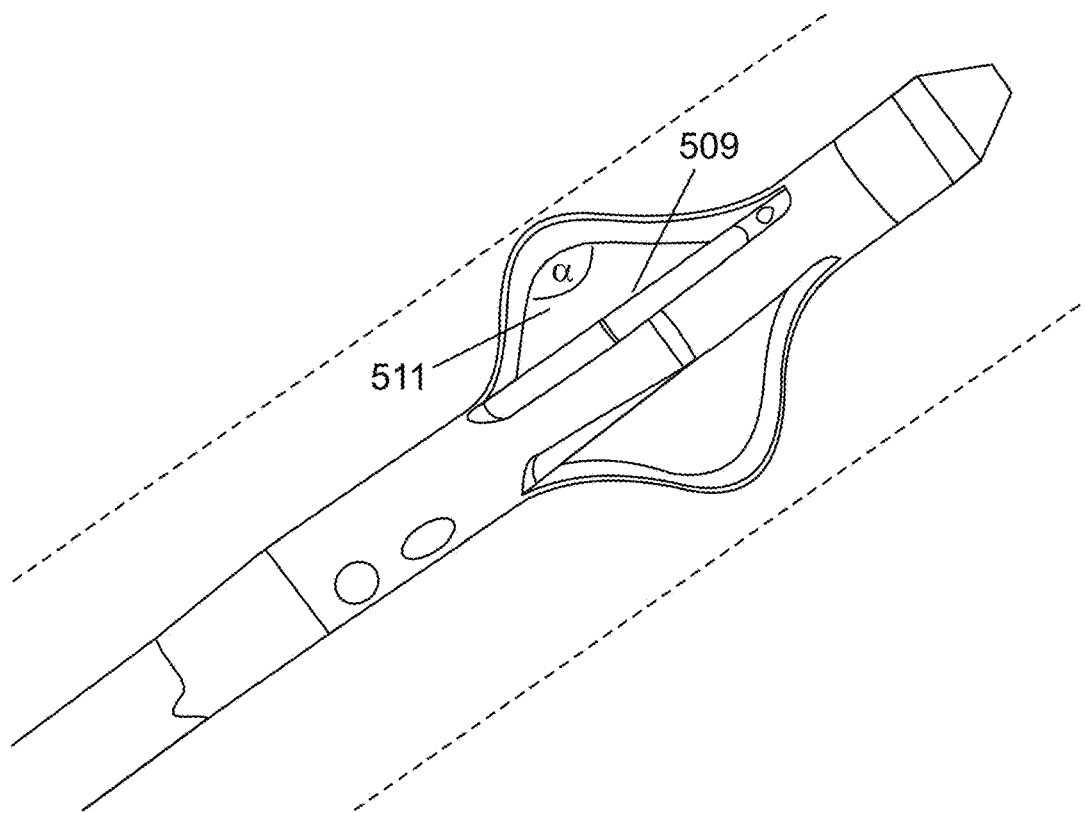

FIGS. 3A-3B are images of a distancing device 501 of a catheter in a closed configuration (FIG. 3A) and an expanded configuration (FIG. 3B), according to some embodiments of the invention. In some embodiments, distancing device 501 is configured for pushing catheter head 503 away from the lumen wall 505. In some embodiments, one or more of the transceivers 509 is pushed away from the wall. In some embodiments, distancing device 501 is configured for centering head 503 with respect to the wall.

In some embodiments, when device 501 is in the closed configuration, a total diameter of the catheter head 503 including the distancing device threaded onto the head is small enough to provide for insertion and/or removal and/or positioning of the catheter within the lumen. For example, the total diameter ranges between 1.3 mm to 2.6 mm or intermediate, longer or shorter diameters. In some embodiments, a total diameter of head 503 is small enough to enable delivery through a guiding catheter or sheath.

In some embodiments, distancing device 501 is formed in the shape of a slotted cylinder. Optionally, cylinder portions 507 in between the slots form bendable leaflets. In some embodiments, in an expanded configuration, as shown for example in FIG. 3B, the leaflets are forced into a rounded 'elbow' shaped configuration, pushing the one or more transceivers 509 away from wall 505. Optionally, the transceiver is pushed at least 1 mm, at least 0.5 mm, at least 2 mm or intermediate, large or smaller distances away from the wall.

In some embodiments, leaflets 507 are positioned such that in the open position, they do not interfere with the field of emitted ultrasound, and in the closed position, the leaflets conform into recesses between the transceivers for maintaining a minimal diameter of the catheter.

In some embodiments, in the closed configuration, leaflets 507 cover at least a portion of the transceiver surface and protect it. In some embodiments, a width of a leaflet is small enough to reduce an unwanted thermal effect on the lumen wall. Additionally or alternatively, a width of a leaflet 507 is selected such as to prevent mechanically induced damage such as scratches to the wall tissue.

In some embodiments, distancing device 501 is expanded in multiple steps, for example 2, 3, 4, 5 steps. In an exemplary embodiment, distancing device 501 is first bended such that an angle α ranging between 110-175 is formed by leaflet 507, and in the second step angle α is reduced to, for example, 90-110 degrees, as transceiver 509 is being pushed further away from wall 505.

In some embodiments, distancing device 501 is transferred into an open configuration by retracting distal tip 513 of catheter head 503 in the proximal direction. Optionally, retraction is performed by pulling an internal shaft of the catheter which is connected to tip 513, such as a guide wire shaft, in the proximal direction. Optionally, retraction is performed by pulling on an inner cable coupled to tip 513. In some embodiments, the guide wire shaft and/or the cable are coupled on one end to distal tip 513, and on an opposite end to a handle configured externally to the body. Optionally, the handle comprises a lever for operating the distancing device, for example by remotely pulling on tip 513 to move it in the proximal direction. In some embodiments, a diameter of the proximal end of tip portion 513 is equal to a diameter of the cylinder of distancing device 501, and by retraction of tip 513 force is applied by the tip on the cylinder of distancing device 501, causing leaflets 1307 to bend.

In some embodiments, distancing device 501 comprises a combination of rigid and soft materials, for example layered on top of each other. Optionally, by using a rigid material, the distance between catheter head 503 and wall 505 is maintained. Optionally, by using a soft material, damage to the tissue of wall 505 is reduced or prevented. In some embodiments, distancing device 501 comprises a soft plastic material embedded with fibers such as Nitinol fibers.

Selective Treatment

Figure 4A:
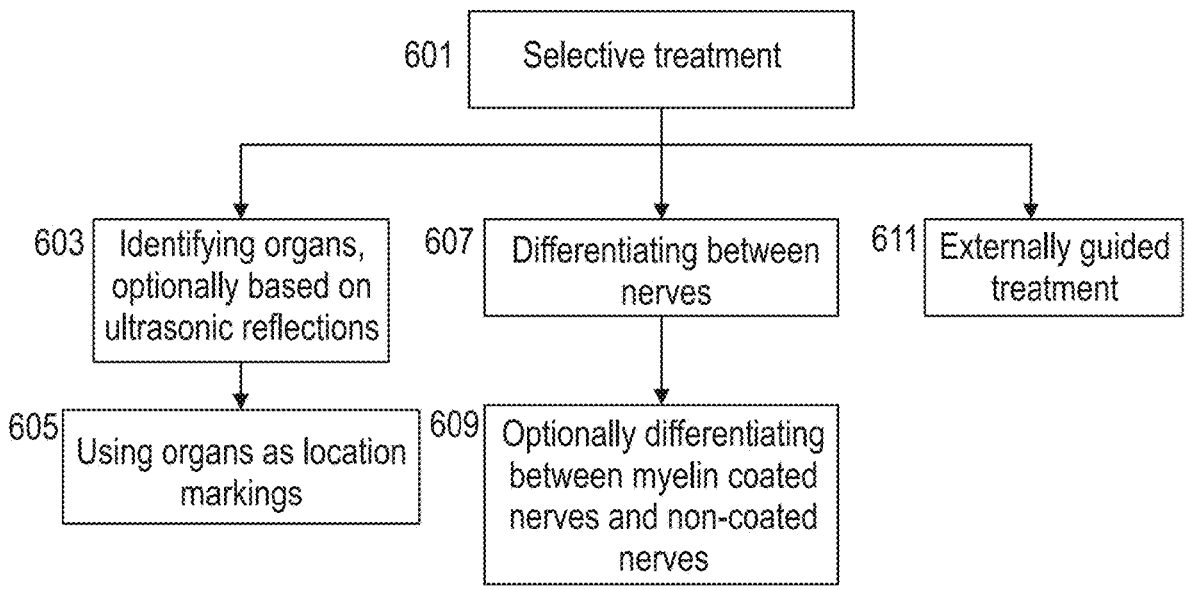

FIG. 4A is a flowchart describing a variety of options for selectively treating nerve tissue, according to some embodiments of the invention. It is noted that any of the described options may be used independently and/or together with one or more of the other options described.

In some embodiments, selective treatment (601) comprises targeting nerves while damage to non targeted tissue, such as surrounding organs and/or non targeted nerves, is reduced or prevented. In some embodiments, selective treatment comprises targeting a predetermined nerve, nerve segment, and/or nerve plexus. In some embodiments, selective treatment comprises identifying nerves according to their innervating function, and targeting those nerves. In some embodiments, selective treatment comprises modifying energy emission parameters such as intensity, frequency, duration, timing and/or other operational parameters according to the selected target, for example according a size of the target and/or a distance of the targeted nerve(s) from the lumen. Optionally, the temperature profile is selected according to desired level of thermal damage and/or according to a location of the targeted nerves with respect to the catheter and/or according to the type of nerve tissue intended for treatment.

In some embodiments, one or more organs are identified before and/or during the procedure (603). Optionally, a location of the organs relative to the lumen is identified based on an ultrasonic reflection of an organ. Additionally or alternatively, organs are identified using imaging modalities.

In some embodiments, echo signals reflected by one or more surrounding organs are received by the one or more transceivers of the catheter device. Optionally, the signals are processed, for example by a console in communication with the device, to identify one or more organs which reflected the signals, such as, for example, one or more of the heart, lungs, aorta, and/or trachea. In an example, a distinctive echo signal pattern may be acquired from the trachea, since it is mostly filled with air. A potential advantage of identifying organs may include increasing a safety level of the device, by distinguishing between the organs even though they may be located very close to each other, and orienting the catheter device to emit energy in certain directions, selected with respect to the identified organs so that damage to those organs is reduced. In some embodiments, the identified organs are used as location markers (605). Optionally, a position of the catheter along the lumen and/or an angular orientation of the catheter are selected using the location markers. In some embodiments, an operating console of the device is configured to provide, for example to a physician, an indication to activate and/or deactivate emission of ultrasound energy, in accordance with the detected location of one or more identified organs. A potential advantage of treating nerves using location markers, such as identified organs acting as location markers, may include reducing a risk of damage to non-targeted tissue. In an example, air ways such as the trachea are identified based on a relatively strong ultrasonic reflection. In another example, the esophagus is identified based on an echo pattern indicating peristaltic movement.

Figure 4B:
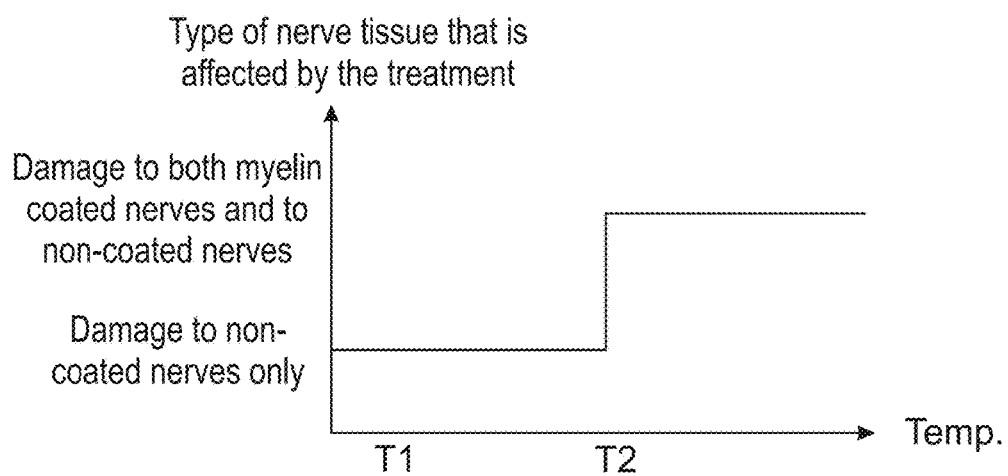

In some embodiments, applying selective treatment includes differentiating between nerves (607). Optionally, differentiating comprises not causing thermal damage to myelin coated nerves (609). The inventors have observed that by selecting a certain temperature profile, for example by denervating using a temperature above, for example, 47 degrees C., yet below, for example, 57 degrees C., thermal damage is caused to nerves that are not coated by myelin, while myelin coated nerves are not damaged. By increasing the temperature, for example to a temperature of 58 degrees C. or higher, myelin coated nerves are damaged. Differentiating between myelin coated and non coated nerves may provide an advantage when treating nerves which innervate the lung vasculature. According to Schelegle et al. (Respir Physiol Neurobiol. 2012 May 31; 181(3): 277-285. doi: 10.1016/j.resp.2012.04.003., "Vagal afferents contribute to exacerbated airway responses following ozone and allergen challenge") myelinated fibers initiate bronchodilation. FIG. 4B is a schematic graph illustrating selectively treating nerves by modifying a temperature profile. As explained hereinabove, when heating at certain temperature range T 1, for example ranging between 47-57 degrees C., only non-coated nerves are damaged. When increasing the temperature to a range T2, for example ranging between 58-70 degrees C., both non-coated nerves and myelin coated nerves are thermally damaged.

In some embodiments, differentiating between nerves comprises identifying the vagus or its branches. A potential advantage of identifying the vagus may include reducing a risk of damaging or affecting the heart, for example due to heating of the vagus which may affect heart rate. Alternatively, the vagus and/or its branches are treated, for example vagal fibers are treated to affect dilation and/or constriction of the bronchi. In some embodiments, the vagus is identified by emission of short bursts of ultrasonic energy, which are capable of exciting the vagus to an extent that substantially does not cause damage to structures that are innervated by the vagus. In some cases, excitation of the vagus affects heart pulsation, and measuring a change in heart rate may provide an indication that the vagus is located within the range of the ultrasonic field emitted by the catheter. Additionally or alternatively, in some embodiments, branches of the vagus such as the recurrent laryngeal nerve are excited by emission of ultrasonic energy, and a response to the stimulation is assessed for identifying whether the vagus and/or one or more of its branches are located within the treatment region.

In some embodiments, for applying selective treatment, an external guiding element is used with the catheter device. Optionally, the external guiding element is positioned externally to the body, for example adjacent the patient's chest. In some embodiments, the guiding element comprises a receiver which receives signals from the catheter device, for example during treatment. Additionally or alternatively, the guiding element is configured to send data to the catheter device, for example to activate or deactivate emission. In some embodiments, the guiding element is in communication with the catheter's operating console. Optionally, the guiding element indicates a current position and/or orientation of the catheter to the console, and treatment is initiated and/or modified and/or ceased based on the indication.

While ultrasound energy, such as non-focused energy, may be specifically advantageous when targeting nerve tissue to modify nerve activity, selective targeting can be performed by using other energy forms and/or methods, such as RF, application of direct heat, and/or other energy forms or methods suitable to thermally affect the targeted nerves.

Feedback

Figure 5:
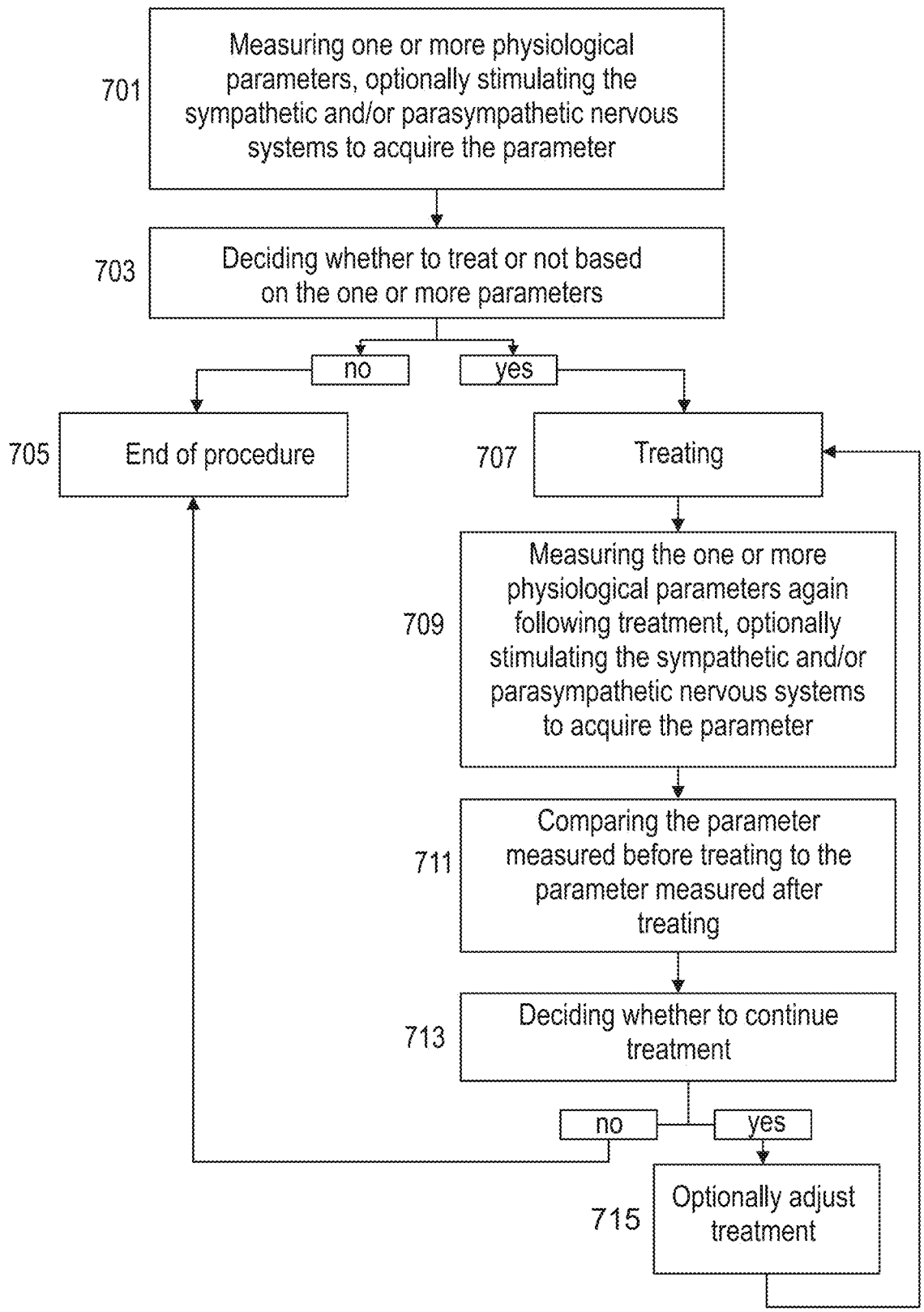

FIG. 5 is a flowchart of an exemplary feedback loop associated with a denervation procedure, according to some embodiments of the invention. In some embodiments, the treatment is modified according to the feedback, for example treatment parameters such as one or more of intensity, duration, frequency, timing, and/or power may be adjusted based on the feedback.

In some embodiments, immediate feedback is obtained in real time. Optionally, feedback is obtained within time periods in between energy emissions. Additionally or alternatively, feedback is obtained before the catheter device is moved to a different location. Additionally or alternatively, feedback is obtained following an excitation and/or a set of excitations of the one or more transceivers, for example 30 seconds, 1 minute, 15 minutes, 1 hour or intermediate, shorter or longer time periods following excitation. In an example, immediate feedback includes observing a visible effect of treatment on the bronchi, such as bronchodilation or bronchoconstriction, which are expected to occur within a relatively short time period, such as 10-120 sec, for example 15 seconds, 30 seconds, 80 seconds or intermediate, longer or shorter time periods following ablation of the nerves which innervate the bronchi, such as the anterior and/or posterior pulmonary plexuses.

In some embodiments, additionally or alternatively to immediate feedback, long term feedback is obtained. Exemplary physiological parameters that can be assessed to obtain long term feedback for the denervation treatment may include one or more of blood pressure, cardiac output, artery wall thickness, artery flow resistance, lung volume, diastolic pressure, and/or other parameters.

In some embodiments, physiological and/or functional changes to the heart, pulmonary artery and/or bronchus are monitored. Optionally, changes are assessed to indicate the effect of treatment. In some embodiments, one or more physiological parameters are measured. Optionally, the parameters are used as control parameters, for deciding whether to continue the treatment and/or whether to modify the treatment.

For example, when monitoring the heart, a parameter such as heart rate may be measured. When monitoring the pulmonary artery, one or more parameters such the artery diameter, arterial blood pressure, blood flow velocity and/or rate, and/or artery stiffness may be measured and/or estimated. When monitoring the bronchus, parameters such as the bronchus diameter and/or the flow rate of air through may be measured and/or estimated.

In some embodiments, one or more parameters are monitored continuously. In an example, heart rate is measured continuously, and if arrhythmia is detected, energy emission from the device is ceased. Alternatively, a parameter is measured once. Alternatively, a parameter is measured intermittently, for example every 30 seconds, every 2 minutes, every 15 minutes, or intermediate, shorter or longer time intervals.

In some embodiments, measurements obtained from the left and right pulmonary arteries are compared to each other, for example to detect a change in the branch that was treated with respect to the branch that was not treated.

In some embodiments, feedback is acquired by receiving echo signals, such as echo signals reflected by the lumen wall, and processing the signals.

In some embodiments, feedback is acquired using a sensor, for example a pressure sensor, a flow sensor, and/or a temperature sensor. Optionally, the sensor is coupled to the catheter device. Additionally or alternatively, a sensor is positioned in the lumen separately from the catheter. In some embodiments, one or more external sensors are used, such as a sensor adapted for detecting breathing of the patient. In some embodiments, a guide wire comprising one or more sensors is delivered through a lumen of the catheter device.

It is noted that where "measurements" or "measuring" are referred to, these may include estimating and/or otherwise indicating a selected parameter.

In some embodiments, one or more physiological parameters are measured (701). In some embodiments, parameters are obtained before treatment. Optionally, the parameters are used as reference (or base line) measurements. In an example, a baseline indication of blood pressure within the pulmonary artery is measured.

In some embodiments, measuring includes one or more of, for example:

assessing heart function, such as heart rate, for example using electrocardiography. In some cases, a change in heart rate is associated with treatment of the vagus and/or vagal nerves. In some cases, a change in heart rate may include arrhythmia.

measuring muscle sympathetic nerve activity (MSNA).

measuring arterial blood pressure and/or other hemodynamic properties, such as mean pulmonary arterial pressure, for example using a "Swan-Ganz" catheter, and/or a pressure sensor mounted onto the catheter device and/or onto a guide wire inserted along with device, for example through a lumen of the device.

measuring artery dimensions, such as diameter, by processing echo signals received by the catheter device and/or by using angiography.

measuring arterial stiffness, for example by processing of echo signals received on the device to determine a movement pattern of the artery wall.

measuring arterial resistance to flow, for example by assessing a difference between pulmonary artery pressure and diastolic left ventricle pressure.

measuring bronchial dimensions, such as diameter, for example by using a balloon. In some embodiments, the balloon is filled with fluid, and a volume of the filled balloon and/or inflation pressure of the balloon is measured for assessing bronchial dimension. Additionally or alternatively, bronchial dimensions are measured using angiography. Additionally or alternatively, dimensions of the bronchus are estimated based on returning echo signals. Optionally, the emitting catheter is located within the pulmonary artery.

measuring air flow (for example measuring parameters such as flow volume, flow rate).

In some embodiments, measuring includes stimulating the sympathetic and/or parasympathetic nervous systems. Optionally, the physiological parameter is a parameter measured in response to the stimulation. In some embodiments, one or more nerves are stimulated to assess their innervating function. Optionally, the nerves that are stimulated are targeted during the treatment. Additionally or alternatively, different nerves than the ones that were stimulated are targeted during treatment.

In some embodiments, stimulating involves one or more of, for example:

using the ultrasonic catheter device for stimulating the nerves. In some embodiments, the device is configured to apply ultrasound energy having parameters suitable for causing a stimulation effect, which does not thermally damage the nerve tissue. Optionally, parameters such as frequency, power, intensity, temperature range, beam shape, catheter location and/or orientation and/or other parameters are selected to produce a stimulating effect, while reducing or preventing thermal damage to the nerves. Optionally, the selected set of parameters defines a stimulating profile that is different from the treating profile.

applying pressure onto the lumen wall, for example by inflating a balloon.

electrically stimulating the nerves. In some embodiments, electrification is provided using one or more electrodes. Optionally, the electrodes are delivered over a balloon which is inflated within the lumen. Additionally or alternately, electrification is applied externally.

heating and/or cooling the trachea which may cause bronchoconstriction.

injecting one or more substances which have a stimulating effect, for example injecting thromboxane A.

In some embodiments, optionally based on the measurement, a decision is made whether or not to treat (703). In some cases, the measured parameter may indicate that treatment (or, in some cases, additional treatment) is not required, and the procedure will end (705). Alternatively, treatment is applied (707). Optionally, parameters of the treatment (for example frequency, power, intensity, duration, temperature profile, and/or other parameters) are selected according to the measurement. Optionally, the targeted nerves are selected according to the measurement. Optionally, a location of the catheter in the lumen is selected according to the measurement.

In some embodiments, the one or more parameters that were measured before the treatment are measured again after the treatment. In some cases, the parameters are measured following emission of a pulse and/or a set of pulses, for example measured 30 seconds, 1 minute, 15 minutes, 1 hour, 3 hours or intermediate, longer or shorter time periods following emission. Additionally or alternatively, the parameters are measured before moving the catheter to a different location.

In some embodiments, parameters acquired before the treatment are compared to the parameters acquired after the treatment (711). In some cases, a change between the response of the nervous system to stimulation before treatment and the response of the system after treatment is observed. Optionally, a threshold is set for defining if the change is significant and indicates that the treatment was effective. Exemplary thresholds may include: a mean diameter of the artery increasing by at least 5%, a heart rate being slowed down by at least 10%, flow pressure in the artery decreasing by at least 20%.

In some embodiments, a decision is made whether or not to continue treatment (713). Optionally, if the parameter comparison indicates that a desired change was observed, for example a mean diameter of the artery increased, for example by at least 5%, 15%, 20% or intermediate, larger or smaller percentages, the treatment is not continued (705). Alternatively, if the comparison indicates that no or partial effects of the treatment were achieved, the treatment is continued. Optionally, treatment parameters are adjusted according to the observed change.

In the following, an exemplary feedback controlled operation of the catheter is described, in which blood pressure in the pulmonary artery is the physiological control parameter that is measured.

In some embodiments, the pressure is measured using an intravascular pressure sensor. Optionally, devices and methods known in the art are used for assessing the intravascular pressure. Additionally or alternatively, in some embodiments, the catheter device is equipped with a pressure sensor, and pressure is measured by the device.

In some embodiments, flow rate, which depends, at least in part, on the resistance of the artery walls to the flow, is estimated, and the arterial pressure is calculated using the flow rate. Optionally, flow rate is estimated using one or more measurements obtained by the catheter device. In some embodiments, flow rate is calculated using the estimated artery cross section area and the flow velocity. Optionally, the artery cross section is estimated using an artery diameter estimation, which was optionally estimated by analysis of echo signals reflected by the artery walls and received by the catheter. Optionally, blood flow velocity is measured using a Doppler device, and/or by using angiography, and/or by thermo-dilution. Optionally, the catheter device comprises an integrated flow velocity measurement mechanism.

In some embodiments, treatment is applied. In some embodiments, to gain feedback following treatment, arterial pressure is measured again. Optionally, stimulation using the balloon is repeated, and the pressure measurements obtained following treatment are compared to the pressure measurements obtained before the treatment. If a change in pressure above a certain threshold is observed, for example the pressure is reduced by at least 5%, at least 15%, at least 50%, at least 70% or intermediate, higher or lower percentages, the treatment is completed. If a sufficient change is not observed, treatment may be repeated, and parameters of the treatment may be modified according to the observed change in attempt to increase the efficiency of the next treatment.

In another exemplary feedback controlled operation regime, the bronchus diameter is measured. Optionally, the diameter is measured continuously. Optionally, the diameter is measured using the catheter device. In some embodiments, the device is positioned within the pulmonary artery, and measurements of the bronchus are performed from within the artery. Treatment is then applied, for example with a gradually increasing intensity level, in parallel to monitoring of the bronchus diameter. Optionally, the treatment is modified based on the measured diameter. In some embodiments, treatment is ceased when reaching a certain intensity level, for example an intensity level above which myelin coated fibers are damaged, since damage to myelin coated fibers may cause constriction instead the desired dilation of the bronchus. In some cases, dilation of the bronchus is achieved by damaging the non-myelin coated fibers, which are prone to thermal damage more than the myelin coated fibers.

Exemplary Configurations of an Ultrasonic Catheter

Figure 6A:
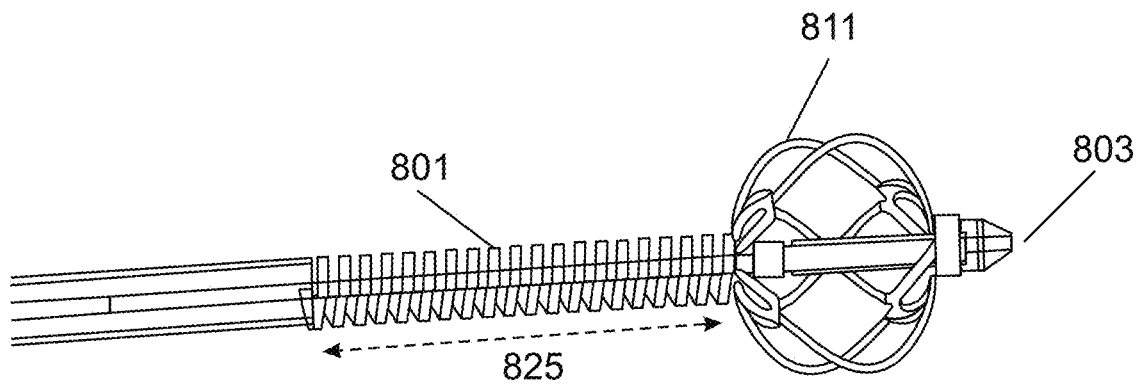

FIGS. 6A-6F2 are various configurations of an ultrasonic catheter device, according to some embodiments of the invention.

In some embodiments, a structure of the device is selected such as to reduce unwanted movement of the device. It is assumed that unwanted movement (i.e. movement beyond a small, allowable range of movement may reduce the efficiency of the treatment, by potentially disrupting the ability to apply a minimal energy intensity level over a minimal period of time which are sufficient to cause a desired effect on the tissue.

In some embodiments, a structure of the device is selected to damp movement such as movement caused by heart pulsation. In some embodiments, axial decoupling or partial axial decoupling is provided between a distal portion of the catheter, which includes the head with the ultrasonic transceivers, and a proximal portion of the catheter.

In some embodiments, a structure is selected to provide damping of movement on one hand, but on the other hand to enable transferring of torque from a proximal portion of the catheter (for example from a handle positioned externally to the body) towards the distal end of the catheter.

In some embodiments, at least a portion of the shaft is rigid enough to enable maneuvering the catheter, for example advancing the catheter. In some embodiments, the shaft comprises one or more flexible portions, facilitating advancing the device along curves of the artery.

In some embodiments, movement damping is provided by a coil 801, for example as shown in FIG. 6A. Optionally, the coil is positioned in proximity to a distal end 803 of the catheter. Optionally, a length 825 of coil 801 is selected according to an expected movement range of head portion 805, for example movement due to heart contraction. In an example, length 825 is selected according to a length of a catheter portion that is most subjected to movement and/or proximal to that part.

Figure 6B:
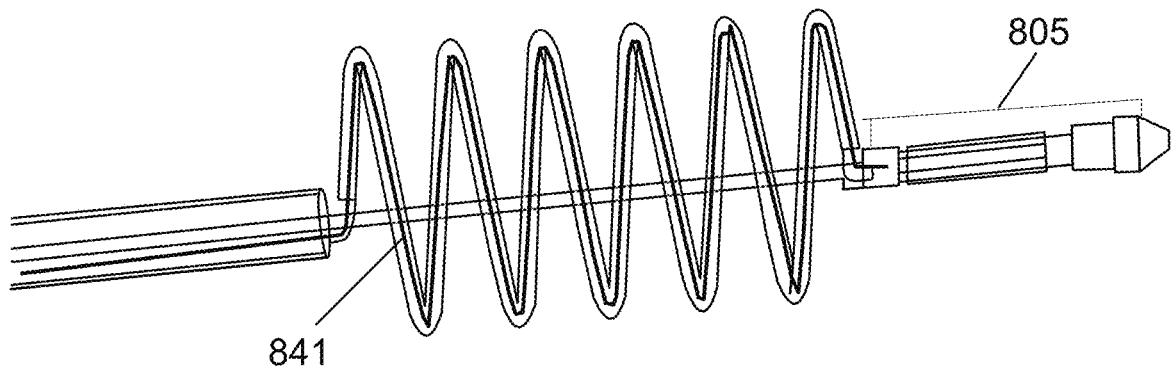

In some embodiments, for example as shown in FIG. 6B, a coil 841 is positioned to reduce movement of head portion 805, for example by extending to a diameter large enough to engage the walls of the artery.

Figure 6C:
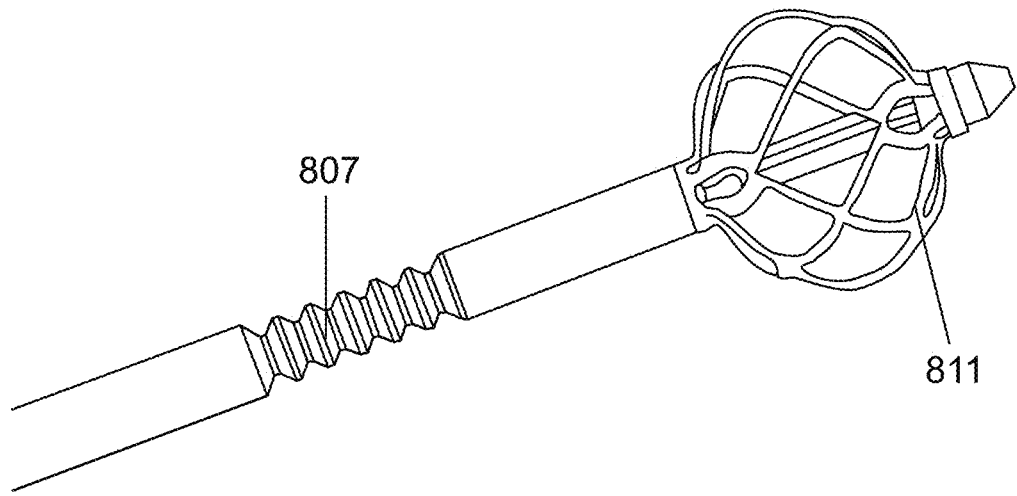

In some embodiments, movement damping is provided by an accordion like portion of the shaft 807, for example as shown in FIG. 6C. In some embodiments, movement damping is provided by a telescopic shaft assembly 809, for example as shown in FIGS. 6D1 and 6D2.

In some embodiments, the catheter device is used with a positioning element. Optionally, the positioning element is shaped to temporarily anchor the device at a certain location and/or orientation. Optionally, the positioning element is shaped to fixate at least a portion of the device in place. In some embodiments the positioning element is structured to push the device, such as push head portion 805, away from one or more lumen walls. Optionally, the positioning element centers the device with respect to the lumen walls.

In some embodiments, the positioning element is delivered in a collapsed configuration, and is expanded in the lumen, for example at a location where treatment is applied. Optionally, the positioning element is expanded in a radially outward direction. In some embodiments, the positioning element is expanded mechanically, for example by pulling at least a portion of the catheter shaft, which is coupled to the positioning element, in a proximal direction, and/or by inflating a balloon within the positioning element, and/or by using an elastic element, such as a spring. In some embodiments, for example as shown in FIGS. 6E1 and 6E2, the positioning element is elastic, and is compressibly folded within a shaft 815 of the catheter. Optionally, when shaft 815 is pulled in a proximal direction, the positioning element is released and is free to expand outwardly.

In some embodiments, for example as shown in FIGS. 6A, 6C and 6D1, a positioning element is shaped as a braided cage 811. Optionally, the braided cage 811 is configured to fixate the catheter device, such as a head portion of the device, with respect to the targeted tissue. In some embodiments, cage 811 is expandable to a diameter in which it abuts against opposing artery walls, reducing axial and/or rotational movement of the catheter device. In some embodiments, cage 811 is formed of a slotted portion of the external shaft of the catheter, which defines expandable leaflets for example as described hereinabove with respect to a distancing device. Additionally or alternatively, cage 811 is threaded onto and/or mounted on the catheter shaft. Optionally, the cage is formed of a shape memory alloy such as nitinol.

In some embodiments, a positioning element comprises a circumferential arrangement of leaflets 813, for example as shown in FIGS. 6E1, 6F1 and 6F2.

In an exemplary embodiment of the catheter device, for example as shown in FIGS. 6F1 and 6F2, an ultrasonic transceiver 817 is coupled to a radially inward facing wall of leaflet 813. Optionally, an emitting surface of transceiver 817 faces a generally central direction, such as towards shaft 821 of the positioning element. In some embodiments, an energy field 819 produced by transceiver 817 is effective to treat nerves located in a radially opposing direction, for example nerves adjacent and/or beyond a wall portion located across from transceiver 817. Optionally, leaflets 813 are arranged with respect to each other in a configuration which permits energy emission in between the leaflets. In some embodiments, a thickness of leaflet 813 is selected to be small enough to reduce the amount of heat absorbed by the leaflet material (e.g. nitinol) during emission of transceiver 817, thereby reducing the amount of heat which may be transferred by the leaflet to a lumen wall that is contact with the leaflet.

In some embodiments, one or more transceivers 817 face a central direction. Additionally or alternatively, one or more transceivers 817 face a direction which is offset from the center.

In some embodiments, leaflets 813 are expandable by retracting a distal tip 827 of the positioning element in a proximal direction, towards a shaft 829 of the catheter. Additionally or alternatively, leaflets 813 are contracted and brought closer to shaft 821 of the positioning element by advancing distal tip 827 in a distal direction.

In some embodiments, the catheter is equipped with a hydrodynamic element, which is suitable, for example, for stabilizing the catheter within the pulmonary trunk, which has a relatively large diameter and carries vast amounts of blood.

A General Method for Treating Nerves Using an Ultrasonic Catheter in the Trachea FIG. 7 is a flowchart a method for treating nerves by positioning an ultrasonic device in the trachea, according to some embodiments of the invention.

In some embodiments, nerve treatment is applied from a tracheal position, for example to treat one or more conditions such as hypertension, asthma, and/or COPD (901, 903).

In some embodiments, an ultrasonic device is introduced to the trachea (905). Since the trachea is a tube like structure which delivers air to the lungs, in some embodiments, the ultrasonic device is adapted to treat surrounding nerves without blocking the air way.

In some embodiments, the ultrasonic device is equipped with a fluid circulation system. Optionally, the fluid in the circulation system (e.g. water, saline) serves as a medium for transferring the ultrasonic energy from the transceivers to the trachea wall.

In some embodiments, fluid circulation system is configured to provide heating and/or cooling. Optionally, heating and cooling are applied simultaneously, for example cooling is applied to prevent over heating of the one or more transceivers, and heating is applied to enhance the thermal damage effect of the ultrasound energy, for example increasing the depth of the effective field in the tissue.

In some embodiments, when positioning the device in the trachea (907), the location and/or orientation of the catheter device are selected according to the relative location of other anatomical structures. For example, in some embodiments, the cartilage rings of the trachea are identified, and treatment is applied in between the rings. Optionally, the cartilage rings are identified by analyzing echo signals reflected by the cartilage tissue and received by the one or more transceivers. In another example, the catheter device is positioned in the trachea at a location in which it is effective to treat pulmonary artery nerves. Optionally, the pulmonary artery is identified according to echo signal reflections, for example signals that indicate pulsed movement of the artery walls.

In some embodiments, treatment is applied to denervate nerves (909), for example by emitting non-focused ultrasound energy having parameters (e.g. intensity, frequency) suitable to thermally damage nerves. In some embodiments, the treatment effect is assessed (911), for example using methods as described in FIG. 21 below (see 2107) and/or as otherwise described in this application.

In some embodiments, the device is moved to a different location (913), such as a different axial location along the trachea. Optionally, treatment is applied again from that location.

For treating in the trachea, various treatment parameters may be specifically selected, for example energy frequency, intensity, beam shape, and/or other parameters.

An Ultrasonic Catheter Equipped with One or More Balloons

FIGS. 8A-8B show an ultrasonic catheter used with one or more balloons, according to some embodiments of the invention.

In some embodiments, as shown for example in FIG. 8A, one or more balloons 1001 are used with the catheter. Optionally, the balloons are symmetrically arranged with respect to a tube 1003 in which catheter 1007 is received, for example as shown in this figure. Alternatively, the balloons are arranged asymmetrically with respect to tube 1003.

In some embodiments, tube 1003 comprises one or more windows 1009, which are sized, shaped and/or positioned to expose the one or more transceivers 1011 of the catheter device.

In some embodiments, the balloons encompass the catheter circumferentially. Alternatively, as shown for example in this figure, the balloons are configured such that they extend along only some portions of the circumference of tube 1003. In some embodiments, the balloons are positioned such that the ultrasonic transceivers lie within spaces in between balloons. In some embodiments, a mechanical element such as one or more rods extend between a transceiver 1011 and a balloon 1001, for example extending to a wall of the balloon, to position the transceiver relative to the balloon, such as axially and/or radially centralize the transceiver with respect to the balloon.

In some embodiments, the balloons are filled with fluid. Optionally, the fluid is heated or cooled. In some embodiments, the fluid is cooled in order to cool the transceiver, allowing it to operate in relatively high intensities, optionally for relatively long periods of time. In some embodiments, the fluid is cooled or heated to control an extent of thermal damage to the tissue, for example heated to increase a depth of thermal damage or cooled to reduce a depth of thermal damage. In some embodiments, an operation console used with the catheter is programmed to activate cooling and/or heating of the fluid, for example by a heating element and/or a cooling element, such as a heating wire positioned within and/or in contact with the fluid in the balloon.

In some embodiments, the balloons are arranged to allow flow in between them and/or over the catheter shaft, such as over the surfaces of the transceivers. In some embodiments, for example when the device is used in the trachea, the balloons are arranged to allow air to flow over the transceivers and/or over the walls of the trachea to cool them. In some embodiments, for example when the device is used in the pulmonary artery, the balloons are arranged to allow blood to flow in between them, over the transceivers and/or adjacent the artery walls to cool them.

In some embodiments, a balloon 1001 is inflated until it contacts the wall of the organ in which the catheter is positioned (such as the pulmonary artery wall, trachea wall). In some embodiments, the balloon is coated with a material suitable to prevent damage to the wall. Optionally, the material is a medicine having a therapeutic effect on the wall, such as Paclitaxel or Heparin. Additionally or alternatively, the material softens the contact of the balloon with the wall, for example having a lubricating effect which reduces friction upon contact with the wall, to reduce a risk of damaging the wall. Exemplary materials for softening a contact between the balloon and wall tissue are acoustic gel, saline and/or water.

In some embodiments, one or more dimensions of the inflated balloon, are selected to provide for energy transfer towards the wall of the organ. In an example, distance 1005 is selected according to the wavelength of the emitted energy.

In some embodiments, the balloons, when inflated, keep the ultrasonic transceivers 1011 of the catheter away from the wall, such as the arterial or tracheal wall.

In some embodiments, a fluid which fills the balloon acts as a transferring medium for the ultrasonic energy. Optionally, a fluid with selected energy transfer characteristics is used. In some cases, energy emitted by the one or more transceivers is modified by the fluid medium when it is transferred through the balloon.

In some embodiments, a balloon 1001 comprises a circular cross section profile, a substantially trapezoidal cross section (for example as shown in this figure), a triangular cross section profile, or other.

In some embodiments, for example during introducing of the catheter into the body, the balloons are in a collapsed configuration. Optionally, the folded balloons are contained within compartments of the catheter, for example compartments configured along an external wall of the catheter shaft. In some embodiments, when the catheter is advanced to a desired location, the balloons are inflated, such as by injection of fluid and/or air. Alternatively, the balloons are introduced separately from the catheter device, for example they are threaded over the guiding sheath following insertion of the catheter. In some embodiments, an angioplasty-like balloon in which the one or more transceivers are contained and/or received is delivered to the target location, and inflated before and/or during energy emission.

FIGS. 9A-9B are an isometric view (9A) and a cross section view (9B) of an ultrasound catheter equipped with a multiple balloon assembly, according to some embodiments of the invention.

In some embodiments, the catheter device 1101 is used with a multiple balloon assembly. In some embodiments, the balloon assembly includes 2, 3, 4, 5, or a higher number of balloons. In the example shown herein, the balloon assembly comprises an internal balloon 1103, which surrounds device 1101, and an external balloon 1105, which encompasses internal balloon 1103 at least in part. A potential advantage of an external balloon which extends only partially over an internal balloon and does not fully surround it may include reducing obstruction of blood flow through the vessel.

In some embodiments, the balloon assembly is adapted to provide heating and/or cooling. Optionally, fluid is circulated within each of the balloons, and is heated and/or cooled according to the need.

In an example, internal balloon 1103 is cooled, for example to cool the ultrasonic transceivers 1111 of the device, and external balloon 1105 is heated, for example to enhance the thermal effect of the emitted ultrasonic energy. A potential advantage of using a hot external balloon may include increasing a depth of the effective field in the tissue.

In some embodiments, a temperature of the fluid within a balloon is selected between 10-43° C., such as 20 degrees, 35 degrees, 40 degrees or intermediate, higher or lower temperature. In an example, fluid is cooled to 10 degrees to provide cooling. In another example, fluid is heated to 40 degrees to provide heating.

Methods and Devices for Reducing Parasympathetic Nerve Activity of the Respiratory Tract of Portions Thereof FIG. 10 is a flowchart of a general method for reducing parasympathetic nerve activity for the treatment of a respiratory syndrome, according to some embodiments.

In some embodiments, a decision is made to treat a patient (2101). In some cases, a patient is selected for treatment when suffering from one or more of: COPD, bronchitis, chronic bronchitis, pneumonia, lung inflammation; a patient diagnosed with SARS, SARS-2, MERS, SARS-CoV-2, COVID-19 and or/other potential viruses which are associated with or may lead to respiratory conditions, for example, inflammation of the respiratory tract or portion thereof; a patient under ventilation or one which is expected to need ventilation; asthma patients; and/or other patients suffering from a respiratory condition.

In some embodiments, a device configured for reducing nerve activity is introduced into the respiratory tract, for example into the lower respiratory tract (2103), such as into the trachea, bronchi or lungs.

In some embodiments, the device is an energy emitting device, configured to emit one or more energy types suitable for damaging nerve structure and/or nerve function. In an example, an ultrasound emitting catheter is used. In an example, an RF emitting catheter is used.

In some embodiments, the device is configured for cryotherapy treatment which reduced or blocks nerve activity, for example by freezing the nerves. In an example, the device comprises a cryo-balloon.

In some embodiments, the device is configured for generating an electric field and/or a magnetic field suitable for reducing, suppressing and/or blocking nerve activity. In an example, the device comprises one or more electrically conductive coils. Optionally, the one or more coils are positioned in the bronchi.

In some embodiments, one or more nerves are temporarily deactivated, for example induction of an electric field. In an example, electrodes positioned inside the bronchi, optionally in contact with the wall of the lumen, generate an electrical current, for example at a frequency that is resonant with the tissue conductivity.

In some embodiments, the device is configured for releasing and/or injecting drugs to the target tissue. For example, one or more of the following substances may be released or injected: medications, irritants, proteolytic enzymes, polyacid, alcohol or phenol (neurolytic blockers), toxin (e.g. Botox, botulinum toxin, tetanus toxin, tetrodoxotin), and/or any other substance suitable for causing a reduction in the parasympathetic activity. In some embodiments, the substance is released continuously; alternatively, the substance is released periodically, for example at selected time intervals.

In some embodiments, the device is configured for performing suction and/or flushing, e.g. of lung secretions.

In some embodiments, treatment for reducing nerve activity is performed (2105). In some embodiments, by reducing nerve activity such as nerve activity in the vicinity of the bronchus, constriction of the bronchial smooth muscles is reduced, potentially reducing coughing and/or shortness of breath. In some embodiments, by reducing nerve activity such as nerve activity in the vicinity of the bronchus, inflammation is reduced. In some embodiments, by reducing nerve activity such as nerve activity in the vicinity of the bronchus, mucus production or in general excess production of secretions in the lungs is reduced.

In some embodiments, treatment is performed taking into account that parasympathetic nerves of the main bronchi of the lungs regulate (by release of acetylcholine) functions such as smooth muscle tone, mucus secretion, and/or local inflammation through interaction with muscarinic receptors found throughout the bronchial tree.

In some cases, such as in COPD patients, pulmonary parasympathetic activity is enhanced. This activity may be the most dominant reversible component affecting airway obstruction in COPD.

In some cases, by improving one or more of the above listed conditions, the oxygenation level of the blood may rise. In some cases, by improving one or more of the above listed conditions, a risk of secondary infection and/or other secondary effects (e.g. pneumonia) is reduced. In some cases, a likelihood of ventilating the patient and/or providing the patient with oxygen supplement is reduced. Optionally, if ventilation is provided, ventilation time may be reduced by the treatment. In some cases, the need for treating the patient with antibiotics is reduced or prevented.

In some embodiments, the applied treatment does not damage the bronchial epithelium and the natural cilia covering the lungs.

In some embodiments, treatment is performed under imaging, for example under fluoroscopy, bronchoscopic visualization, and/or other.

In some embodiments, feedback for the performed treatment is obtained (2107), such as during and/or following treatment. In some embodiments, the device is configured for obtaining the feedback, for example by including one or more sensors. Examples of feedback include: assessing breathing of the patient, for example, the patient's respiratory rate; assessing oxygen levels, for example using an oximeter; assessing flow of air through the respiratory tract or portions thereof, for example using a flow sensor; assessing vital signs of the patient (e.g. heart rate, temperature, blood pressure); assessing lung capacitance; assessing the humidity or the humidity change in the lungs, for example by using humidity sensors; assessing nerves activity distally to the denervation location in the bronchi, for example by using electrode and or antenna to measure magnetic field of the nerves conductivity.

In some embodiments, feedback is obtained immediately following treatment and/or at one or more times post treatment, for example 3 hours, 6 hours, 1 day, 1 week, 1 month or intermediate, longer or shorter time periods post treatment.

In some embodiments, post-treatment measures are compared to pre-treatment measures to assess treatment effectiveness and/or to determine if further treatment should be applied.

FIG. 11 schematically illustrates introducing of a nerve suppressing element through an endotracheal tube, according to some embodiments.

In some embodiments, a device configured for suppressing nerve activity is introduced into the respiratory tract, for example through an endotracheal tube 2203. In some embodiments, the device comprises one or more elements 2201 configured to reduce or eliminate parasympathetic nerve activity, for example in nerves located or extending along the bronchi and/or within tissue surrounding the bronchi. In some embodiments, the nerve activity is suppressed to an extent sufficient to reduce production and/or secretion of mucosa and/or hyaluronic fluid production.

In some embodiments, the endotracheal tube comprises or is coupled to a fixation element 2205, for example a fixation balloon which maintains the endotracheal tube in position. Optionally, the fixation element is located at a distal end of the tube.

In some embodiments, the nerve suppressing element is positioned proximally to the fixation balloon. In some embodiments, the nerve suppressing element is positioned distally to the fixation balloon. In some embodiments, the nerve suppressing element is configured as a part of the fixation balloon, for example located inside the balloon.

In some embodiments, the nerve suppressing element is configured for delivering energy suitable to cause damage to the nerve tissue. In some embodiments, the energy thermally modulates the nerve tissue.

In some embodiments, the thermal modulation is performed using RF energy. Optionally, the RF energy is unipolar and/or bipolar. In some embodiments, one or more radiofrequency emitting electrodes are used. In an example, RG energy is emitted at 10-20 W.

In some embodiments thermal modulation is performed using ultrasound energy. Optionally, the energy is emitted a non-focused beam. Alternatively, the energy is emitted as a focused beam.

In some embodiments, the energy is emitted from a single element. Alternatively, the energy is emitted from multiple elements, such as an array of elements.

In some embodiments, energy emission is performed from one or more rotational positions within the lumen, for example from 1, 2, 4, 8, 10, 15 rotational positions or intermediate, larger or smaller number of positions. In an example, the energy emission element is rotated towards several rotational positions, for example at 180 degree, 90 degree intervals, 60 degree intervals, 30 degree intervals from each other. Additionally or alternatively, circumferential treatment is applied. Additionally or alternatively, continuous excitation is performed while the transducer is rotated in the lumen (e.g. of the bronchi) and energy is emitted circumferentially or along a part of the circumference.

In some embodiments, treatment is applied from several axial positions along the length of the lumen, for example by moving the element axially within the lumen.

In some embodiments, the nerve suppressing element is surrounded by fluid, for example surrounded by a fluid balloon. In some embodiments, the surrounding fluid is used as a transfer medium for the energy. In some embodiments, the surrounding fluid cools the energy emitting element(s). In some embodiments, the surrounding fluid cools tissue, for example tissue of the inner wall of the body lumen from which treatment is applied (e.g. the wall of the trachea, the wall of the bronchus).

In some embodiments, the nerve suppressing element is configured to generate an electrical field and/or a magnetic field.

In some embodiments, a sensor 2207 configured for detecting and/or measuring nerve activity is used. In some embodiments, one or more sensors are positioned distally to the treatment location so as to measure nerve activity. In an example, an electrode and/or antenna are used to sense and/or measure a magnetic field induced by neural conduction.

In some embodiment, to test the effect of treatment, the Hering-Breuer inflation reflex (HBR), is triggered. The HBR is known to prevent over-inflation of the lungs. In some embodiments, a balloon-tipped catheter may be placed in the bronchi in various locations to assess the functionality of this reflex, such as before and/or following the denervation procedure.

In some embodiments, a bronchi bifurcation located prior to (i.e. proximally to) the treatment site may be used as an HBR control test location since the nerves along this portion of the bronchi were not targeted by the treatment. In some embodiments, a bronchi bifurcation located beyond (i.e. distally to) the treatment site may be used as a test location, by evaluating sensory denervation and/or disruption of the HBR following the procedure.

In some embodiments, to assess the presence or absence of the reflex, flow in and out of the endotracheal tube may be measured while the balloon is inflated, and the lung distal to the balloon is pressurized to stimulate the HBR. Cessation of respiratory flow during balloon inflation and lung pressurization may be indicative of a positive HBR and of intact sensory innervation of the occluded and pressurized portion of the lung. These may be observed, for example, in the test location.

In some embodiments, normal breathing during balloon inflation and lung pressurization may be indicative of a disruption of the HBR and loss of innervation to at least a section of the lung. These may be observed, for example, in the test location. Therefore, in some cases, this observation indicates that denervation treatment was effective.

In some embodiments, assessment of the treatment effect is performed by performing a Pulmonary Function Test (PFT), for example according to the guidelines of the current American Thoracic Society/European Respiratory Society (ATS/ERS). This test may be performed in one or more time points following treatment, for example one or more times within a year from treatment.

In some embodiments, a conduit (not shown) is provided for allowing flow of air into the lung, for example the conduit passes through the nerve suppressing element and/or through the balloon and/or through the fixation element positioned distally to the endotracheal tube.

In an example in which a catheter device is used, such air conducting conduit may comprise of an inner lumen of the catheter, for example a lumen of the catheter chassis.

FIG. 12 shows a system configured for ultrasound denervation from within the trachea and/or from within the bronchus, according to some embodiments.

In some embodiments, the system comprises of a control console 2301 and a catheter 2303 (e.g. a TIVUS™), the catheter sized for insertion into the bronchus. For example, a diameter of a catheter for treating in the bronchus is between 4F-12F. For example, a diameter of a balloon used with the catheter can expand to a maximum of between 10 mm-17 mm. Optionally, balloon expansion (e.g. by inflation) is controlled in response to images viewed via a bronchoscope. In some embodiments, the balloon is formed of a compliant material. Alternatively, the balloon is formed of a semi-compliant or a non-compliant material. In some embodiments, the expanded balloon diameter is assessed by measuring the fluid volume (e.g. saline, water) injected into the balloon and/or by measuring the pressure within the balloon.

In some embodiments, the catheter comprises a plurality of ultrasound emitting elements 2305 (e.g. piezoelectric transducers) configured for emission of non-focused ultrasound energy. In some embodiments, the ultrasound emitting elements are configured for emission of high intensity non-focused ultrasound which targets nerves adjacent the lumen of the bronchus.

In some embodiments, the console controls the applying of treatment, for example controls treatment parameters (automatically and/or based on received input). In some embodiments, the console performs analysis and/or contains a user interface and/or displays measurements and/or communicates with additional devices.

In some embodiments, in use, the catheter is positioned into the bronchus while being surrounded by a fluid filled (e.g. saline filled) balloon (not shown). In some embodiments, energy emitted by the plurality of ultrasonic elements passes through the fluid medium of the balloon, through the tissues into the intracellular matrix and into nerve bundles outside (e.g. surrounding) the bronchus.

In some embodiments, the emitted energy targets parasympathetic cholinergic nerves which surround the main bronchi of the lungs. These nerves commonly regulate the airway smooth muscle tone, regulate mucus secretion, and are involved in local inflammation response through interaction with muscarinic receptors found throughout the bronchial tree.

In some embodiments, the emitted energy targets nerves which control the parasympathetic output, which in a condition of inflammation (which may optionally worsen due to viral causes, such as in COVID-19 patients) may cause bronchial constriction, excess mucus and/or excess hyaluronic fluid production, and in some cases, pneumonia and/or alveolar disease, optionally leading to death.

In some embodiments, mucus secretion is reduced by at least 30%, at least 50%, at least 70%, at least 90% or intermediate, higher or lower percentage relative to the amount of mucus secreted before the denervation treatment.

The inventors of this application have found, based on preclinical work for the treatment of COPD patients, that by affecting nerve function and/or structure, e.g. by thermally damaging the nerves, the inflammatory response may be reduced; secretion of mucosa may be reduced; and bronchial constriction may be reduced.

FIGS. 13A-13C illustrate a treatment scheme using an energy emitting catheter inserted into the bronchus, according to some embodiments, and an example of a histopathological result of the treatment.

In FIG. 13A, in accordance with some embodiments, an ultrasound emitting catheter is positioned in the bronchi, surrounded by an inflatable balloon comprising fluid, for example, cooled saline.

As shown in FIG. 13B, in accordance with some embodiments, energy emitted by the one or more ultrasonic transducers of the device travels through the fluid medium of the balloon, through the wall of the bronchus and into the surrounding tissue.

In some embodiments, the energy is absorbed in the targeted tissue region and is transformed to heat, causing thermal effects to the nerves. Optionally, the target tissue is heated to a temperature between 50° C.-80° C. In some embodiments, additional effects on the tissue (e.g. cavitation, streaming) are insignificant.

In some embodiments, damage to the wall of the bronchus (such as to the epithelial layer covering the wall) is reduced or prevented, for example by the cooled fluid within the balloon.

In some embodiments, the cooled fluid within the balloon cools the transducers, e.g. by cooling the transducer surface, thereby preventing overheating.

FIG. 13C shows histopathology results from a study performed in swine model, demonstrating necrosis of the nerves around the bronchi. Thermal damage regions at and/or around nerves (marked by *) are outlined. As can observed, nerve branches extending along the main bronchi, externally to the lumen of the bronchi are damaged. By thermally damaging these nerves, the parasympathetic signaling to the lungs may be affected, potentially resulting in a decreased neural release of acetylcholine. This reduction in acetylcholine was shown to reduce airway obstruction in the lung by decreasing smooth muscle tone and by decreasing hyaluronic section, such as hyaluronic section caused as a response to viral infection (e.g. in COVID19 infection).

Parameters used in the study included:
Ultrasound energy intensity of between 10 W/cm^2-50 W/cm^2;
Ultrasound energy frequency of between 8 MHz-20 MHz;
An emission duration of between 10 seconds-60 seconds;
The location from which energy was emitted included a section of the bronchi (of both left and right bronchi), between about 1 cm to 10 cm from the trachea bifurcation. It is noted that other treatment areas may be implemented, such as about 5 cm to 20 cm from the trachea bifurcation, about 0.5 cm to 5 cm from the trachea bifurcation or intermediate, longer or shorter distances relative to the bifurcation.

FIGS. 14A-14C are images of an in-vitro experiment performed to demonstrate the effects of treating from inside the bronchus, according to some embodiments.

In the experiment performed, an ultrasound emitting catheter was introduced into a saline filled balloon, see FIG. 14A. The catheter surrounded by the balloon was then inserted into a tissue portion having being shaped and sized to match the human bronchus (having a diameter similar to that of the human bronchus), see FIG. 14B.

Following emission of energy, thermal damage was observed in the exterior wall of the tissue portion, see FIG. 14C. No thermal damage was observed in the internal wall of the tissue portion, which surrounds the lumen through which the balloon catheter was introduced.

FIG. 15 schematically illustrates treatment applied from inside the bronchus, according to some embodiments.

In some embodiments, the bronchus and/or trachea are partially filled with a fluid medium, for enabling the transferring of energy (e.g. ultrasound energy) from an energy emitting element 2605 to the surrounding tissue.

In some embodiments, a blocking element 2601 such as a balloon is introduced into the lumen, and positioned at a location distal to the location intended for energy emission. Following deployment of the blocking element (e.g. by inflation of the balloon), fluid 2603 is introduced into the lumen, and allowed to accumulate due to the blocking, for example accumulate above the blocking element. Examples of the fluid medium may include saline, water, cooled fluid.

In some embodiments, the fluid medium provides for energy transfer to the tissue outside the lumen.

In some embodiments, the fluid medium cools the wall of the lumen and/or cools the energy emitting elements of the device (e.g. the ultrasound transducers).

FIGS. 16A-16G demonstrate a setup and results of a denervation study performed in swine, in accordance with some embodiments.

Figure 16A:
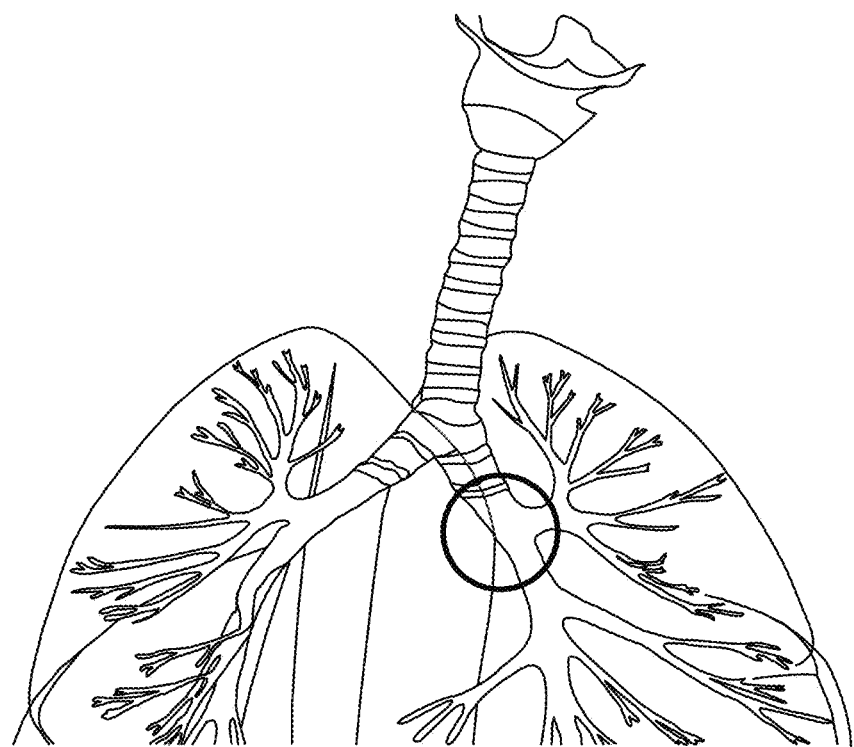

In the study, two swine models were treated via ultrasonic ablation from within the trachea and the bronchi (e.g. to the position shown in FIG. 16A, within the left bronchus). Before treatment, the lung was filled with fluid, to demonstrate a condition of inflammation.

In the study, a TIVUS™ catheter was introduced through an intubation tube. An 8F sheath (morph) catheter was used. Imaging of the trachea and the bronchi was performed with the aid of contrast material (diluted in a saline solution) which was injected into the trachea.

The following steps were performed:
Immediately following euthanasia of the swine, the lungs and trachea were filled with a contrast material diluted in a saline solution and injected through an intubation tube using a syringe pump.

A TIVUS™ catheter comprising multiple ultrasonic transducers was introduced through the intubation tube.

Ultrasonic energy emission was performed while constantly injecting fluid through the catheter in attempt to avoid overheating of the catheter. The intensity of the emitted non-focused ultrasound energy was within the range of 25-40 W/cm^2. The duration of emission at each excitation session was between 20-30 seconds. 12 excitation sessions were performed.

Following ablation, the trachea, bronchi and adjacent tissue were harvested and analyzed by a histopathological analysis.

Figure 16B:
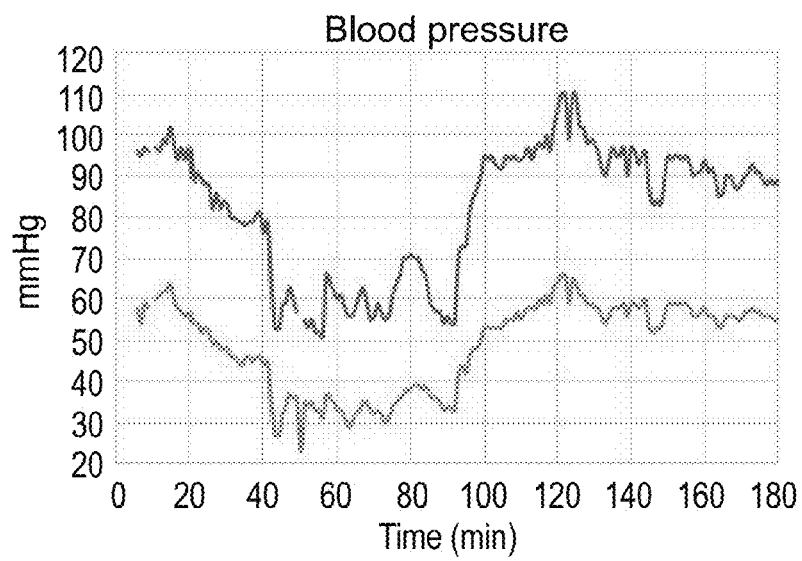
Figure 16C:
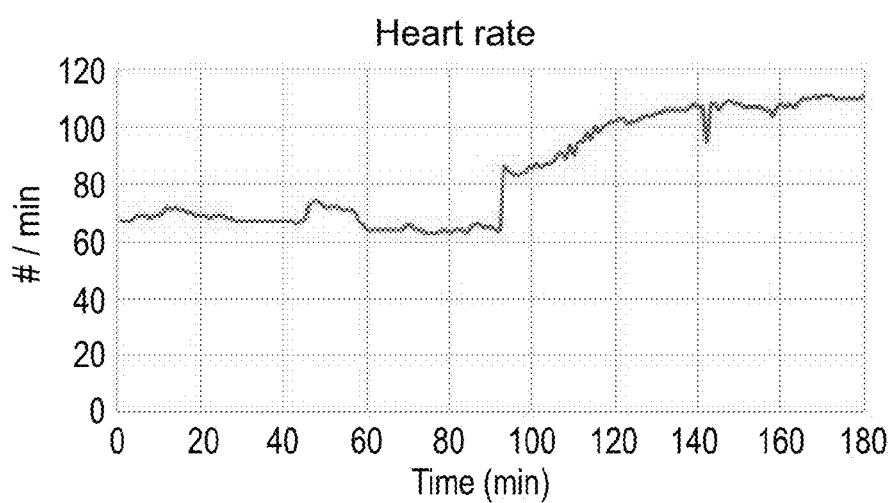
Figure 16D:
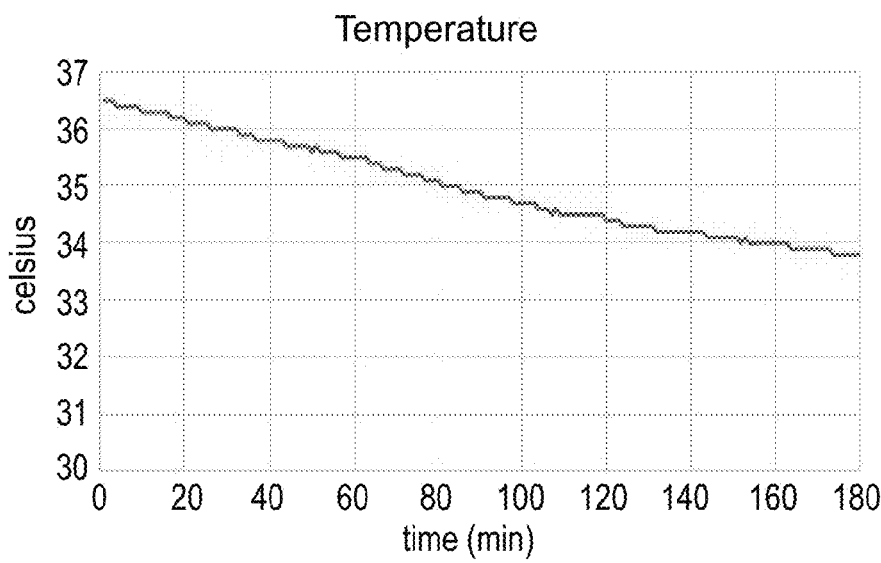

The graphs of FIGS. 16B-D show vital sign monitoring of the swine model during the experiment:

FIG. 16B shows the diastolic and systolic blood pressure changes. At about 90 minutes from the start of the experiment, blood pressure decreased, and noradrenaline was provided in a continuous drip (IV), causing the blood pressure to rise.

FIG. 16C shows the heart rate changes. Simultaneously with the rise in blood pressure, a rise in heart rate was observed.

FIG. 16D shows the swine model body temperature over time.

Figure 16E:
Figure 16F:

FIGS. 16E-16F are images showing the position of the ultrasound emitting catheter, within the bronchus. At the shown position, ablation was performed.

Figure 16G:
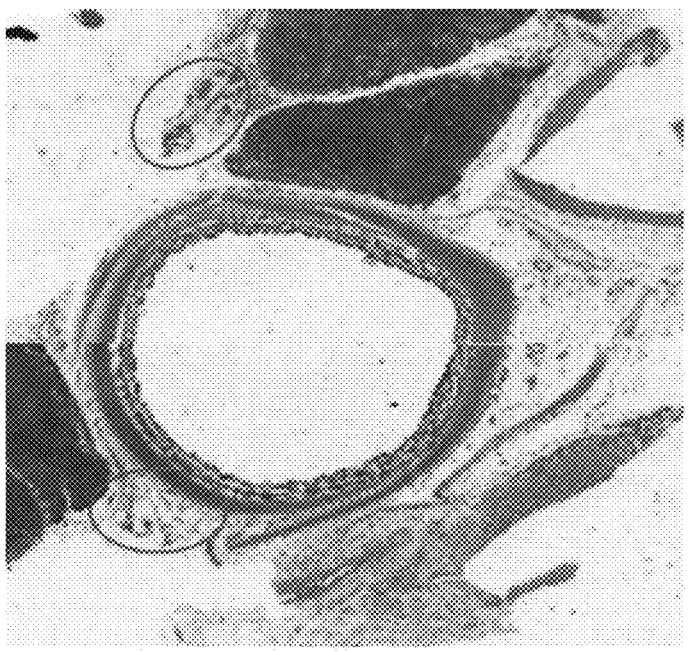
Figure 17A:
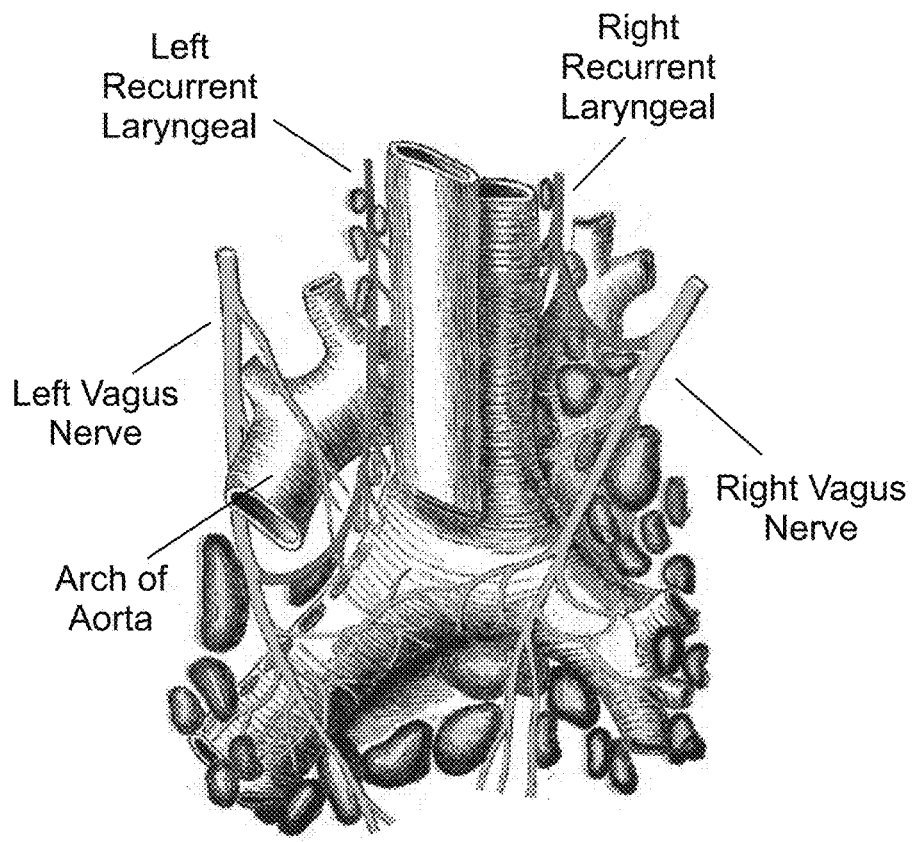
Figure 17B:
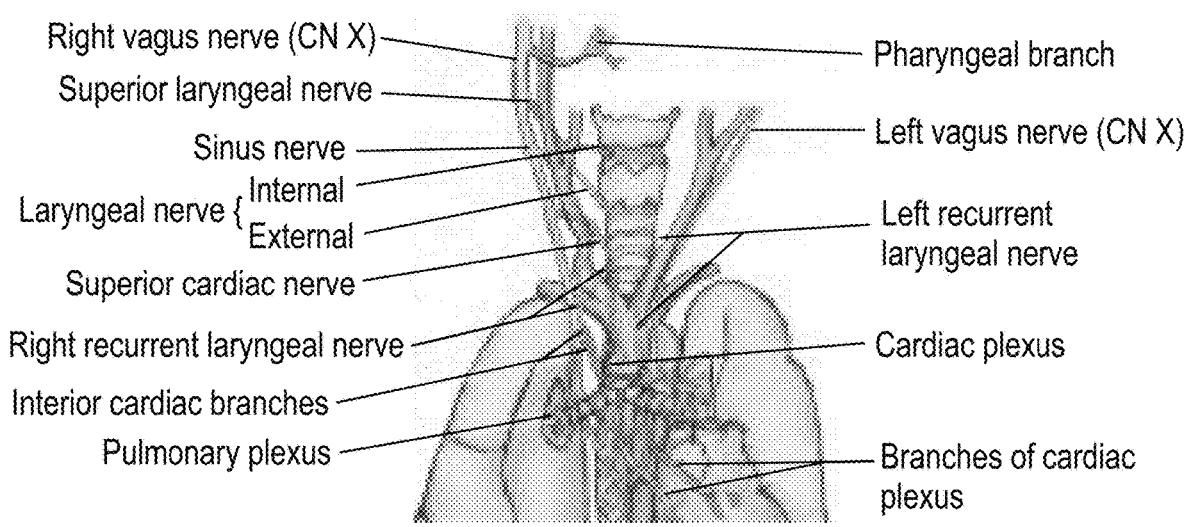
Figures 17C, 17D:
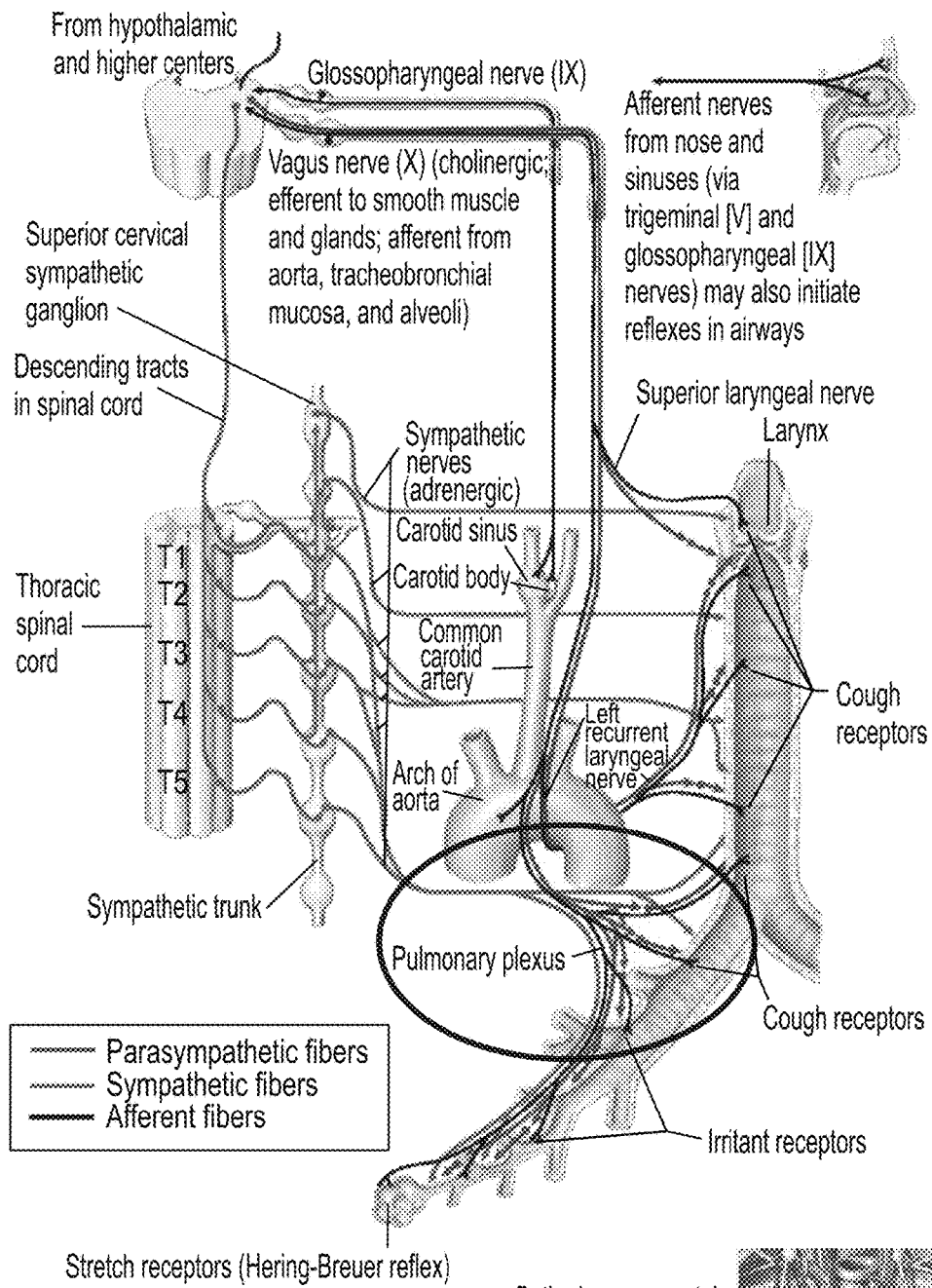

FIG. 16G shows a histopathology analysis of the harvested tissue. Thermal necrosis was observed in three separate locations around the trachea, located at a distance of about 90-100 degrees from each other. Nerves, arterioles and venules within the heated tissue were necrotic, while several large arteries remained viable. Minimal smooth muscle necrosis was observed.

FIGS. 17A-D are anatomical illustrations showing the target nerves peripheral to the bronchus and/or to the trachea, according to some embodiments.

In some embodiments, treatment is applied to reduce neural activity of nerves located at the surroundings of the trachea and/or the bronchus.

In some embodiments, the target nerves and/or nerve plexuses include the vagus nerve and/or branches of the vagus nerve (e.g. branches of the left and/or right vagus nerve).

The vagus nerve interfaces with parasympathetic control of the heart, lungs and digestive tract. Autonomic innervation of the lung is provided by the vagus nerve via the pulmonary plexus which originates at the level of the main carina and extends to nerve branches along each main stem bronchi. By interrupting vagal innervation to the lung, such as by thermally damage of the nerves, acetylcholine release from these nerves may be reduced or eliminated, potentially influencing smooth muscle tone, mucus secretion, and/or local inflammatory processes. Optionally, the applied treatment affects lung innervating branches of the vagus nerve, but substantially does not affect the main trunk of the vagus.

In some embodiments, treatment is applied to disrupt axons, optionally affecting (e.g. preventing) their regeneration.

FIGS. 18A-B demonstrate an effect of internally (FIG. 18A) and externally (FIG. 18B) applied vibrations on the tissue, according to some embodiments.

In some embodiments, the device inserted into the bronchus and/or the trachea is configured to vibrate. In some embodiments, vibration causes mucus in the airways to loosen and/or separate from the tissue walls on which it is attached.

In some embodiments, in a device comprising one or more ultrasound transducers, the transducers are configured to oscillate, for example at a frequency of the delivered US signal. The oscillation may further warm the working area along the inner tubes of the respiratory system, in an example the trachea, bronchi and/or lung.

In some embodiments, energy at a given frequency is transferred through a fluid medium, e.g. of a balloon surrounding the device, and is then absorbed in the tissue of the wall, causing the wall to oscillate and/or vibrate. Such vibration may raise the temperature of the tissue, potentially promoting separation and/or breaking of mucus stuck to the walls. The thinned and/or broken mucus then be easier to remove, such as via suction means.

Additionally or alternatively, the device is configured to stimulate (e.g. electrically stimulate) muscles, such as muscles which control bronchial constriction. In an example, stimulation is applied to induce coughing which may assist in increasing the mucus motility and accelerate mucus detachment. Coughing may further move the mucus to the upper airways, from which it can naturally exit and/or removed by suction.

FIG. 18B shows an example of a device, for example a wearable vest, configured to apply external vibrations, according to some embodiments.

In some embodiments, the wearable device is configured to produce vibrations which in turn vibrate the tissue, assisting in mucus detachment and/or removal.

In an example, the wearable device is shaped as a vest comprising air bags which are in fluid communication with an air compressor. The compressor delivers bursts of air flow and/or sucks the air to generate rapid inflation and deflation of the vest, for oscillating the wall of the chest.

In some embodiments, the vibration produces breaking of the mucus and/or makes the mucus thinner. In some embodiments, the vibration induces a coughing action which assists in moving the mucus up the airways. In some embodiments, the vibration accelerates the function of the cilia and accelerates carrying of the loosed mucus by the cilia to the upper airways.

In an example, the vibration frequencies of the externally worn device are between 10-15 Hz, 5-50 Hz, 20-100 Hz or intermediate, higher or lower frequency. In an example, vibration sessions are applied for a duration of between 5-60 minutes each.

In some embodiments, vibration (such as high frequency chest wall oscillation) is applied to patients suffering from conditions such as CF, COPD, Covid-19 patients whose condition has deteriorated and their blood oxygenation has decreased, SARS patients, bronchiectasis and/or other respiratory conditions. In such patients, clearing the airway from mucus may help prevent infection and/or reduce inflammation.

In the example of Covid-19 patients, increasing amounts of fluids accumulate in the lungs, and the applying of oscillations may help reduce or remove these fluids, potentially increasing a likelihood of the patients to breath on their own. Even in anesthetized patients, who may not breath and cough on their own, applying of oscillations may facilitate mucus suction.

FIGS. 19A-B are examples of a catheter positioned in the bronchi with the aid of an anchoring balloon, according to some embodiments.

In some embodiments, an inflatable balloon is positioned at a lumen location which is proximal to the location in which the energy transmitter is positioned. In some embodiments, the inflated balloon contacts the walls of the lumen.

Optionally, the balloon acts as an anchor which holds the energy transmitter is place, such as during the applying of energy. FIG. 19A shows the catheter inserted into the right primary bronchus, and the balloon inflated to contact the walls of the right bronchus. FIG. 19B shows the catheter inserted into the left secondary bronchus, and the balloon inflated at a location of the bifurcation, to provide anchoring for the energy transmitter.

FIGS. 20A-B schematically show locations of nerve denervation, control testing locations and result testing locations along the bronchus, according to some embodiments.

In some embodiments, as shown, nerves surrounding the trachea and/or the bronchus are targeted by the treatment.

In some embodiments, nerves or nerve sections located proximally to the denervation location (e.g. along the lumen of the bronchus) are used as control locations-optionally, nerve function in such proximal location is measured and/or sensed to determine natural functioning of the nerves, without the effect of denervation.

In some embodiments, nerves or nerve sections located distally to the denervation location (e.g. along the lumen of the bronchus) are used as locations for assessment of the effect of denervation. Optionally, nerve function in such distal location is measured and/or sensed to determine whether the denervation has affected (e.g. reduced) nerve conduction.

FIG. 21 is a schematic drawing of a catheter comprising a head including an energy transmitter positioned within an inflatable balloon, according to some embodiments.

In some embodiments, the catheter head comprises an energy transmitter (e.g. ultrasound transducer) positioned within an inflatable balloon. In some embodiments, the catheter comprises a moveable sheath which when pulled proximally, releases the balloon. In some embodiments, a handle portion which controls of operation of the catheter (externally to the body) comprises a slider for controlling movement of the sheath. In some embodiments, the handle portion comprises a syringe through which fluid (e.g. saline, water) can be injected to fill the balloon.

FIG. 22 is a schematic drawing of a catheter including a cryo-balloon, according to some embodiments. In some embodiments, the cryo-balloon is positioned in the bronchi. Optionally, the cryo-balloon is filled with a cool fluid at a temperature low enough to slow or stop functioning of nerves in the vicinity of the balloon. In some embodiments, the cryo-balloon cools to a temperature below 5° C., below 0° C., below −20° C., below −30° C., below −50° C. or intermediate, higher or lower temperatures.

FIG. 23 is a schematic drawing of an energy emitting catheter for insertion through a bronchoscope working channel, according to some embodiments.

In some embodiments, the catheter is introduced into the trachea and/or further into the bronchial system for treating nerves by energy emission.

In some embodiments, the catheter comprises an elongate shaft 2351 defining an internal lumen through which one or more electrical connections (e.g. wires 2353) are passed. Optionally, the shaft is flexible. In some embodiments, the shaft is formed of materials such as Pebax, nylon, PTFE, ETFE, PEEK, and/or other medical grade material.

In some embodiments, the shaft is sized to enable delivering of a balloon through.

In some embodiments, the shaft is small enough in diameter so as to fit and extend within a lumen of the bronchoscope's working channel.

In some embodiments, the shaft is rigid enough to transfer force (e.g. torque) along it, providing for steering the head of the catheter.

In some embodiments, a balloon 2355 is mounted at distal end of the shaft. In some embodiments, the balloon is inflatable by injection of fluid into the balloon, for example saline and/or other fluid suitable for acting as a transfer medium for the ultrasound energy emitted by the transducers. In some embodiments, the catheter shaft is hermetically sealed to the balloon and is leak-proof along its length.

In some embodiments, the balloon is formed of a soft, elastic and durable material, for example, chronoprene, latex, silicon, polyurethane (urethane) elastomers, polycarbonate based aromatic thermoplastic, TPU, carbothane, techothane, PolyBlend, nylon elastomers. Optionally, the balloon is formed of more than one layer of material, e.g. a double layer chronoprene material.

In some embodiments, the balloon material is characterized by ultimate elongation, allowing for expanding the balloon from a compact sized collapsed state to an inflated state without failure (e.g. breaking, deformation) of the material.

In some embodiments, the balloon material is selected so as to enable the transfer of ultrasound energy through. In some embodiments, the balloon material is configured to adhere to tissue of the anatomical lumen in which it is positioned, establishing a contact surface with the tissue which is large enough to sufficiently transfer the energy to the tissue.

In some embodiments, the balloon is inflated to a size in which no or only a small number of air cavities exists between the outer walls of the balloon and the inner walls of the anatomical lumen (e.g. the inner walls of the bronchus). In some embodiments, the inflation pressure is limited (optionally, the inflation pressure is monitored) to prevent or reduce trauma to the tissue of the lumen.

In some embodiments, a head 2357 of the catheter is configured inside the volume defined by the balloon 2355. In some embodiments, head 2357 comprises of a plurality of energy emitting elements, such as a plurality of ultrasound transducers. For example, head 2357 comprises 1, 2, 3, 4, 5, 6, 7, 8 or a higher number of ultrasonic transducers. In some embodiments, transducers are arranged to face different circumferential directions. In some embodiments, energy (e.g. electrical current) to the transducers is conducted through the one or more electrical wires 2353 extending within the shaft.

In some embodiments, the catheter head is held inside the volume of the balloon. Optionally, the catheter head is centralized inside the volume of the inflated balloon. In some embodiments, the external walls of the balloon contact the inner walls of the anatomical lumen, while the catheter transducer(s) remain at a distance from the balloon (and anatomical lumen) walls, for example a distance of at least 1 mm, 3 mm, 5 mm, 10 mm, 1 cm or intermediate, longer or shorter distance from the walls of the balloon.

In some embodiments, the catheter head is centralized in the balloon. In some embodiments, the catheter shaft is rigid enough to hold the catheter in place relative to the inflated walls of the balloon. In some embodiments, the balloon is disposed (such as in a collapsed state) about the catheter head so that when the balloon is inflated the balloon walls equally expand away from the catheter head.

In some embodiments, when changing a position and/or location of the catheter inside the body lumen, the balloon is collapsed and then re-inflated at the new location.

In some embodiments, a hypotube 2359 extends from a proximal end of the shaft 2351, ending with a connector 2358 through which fluid can be introduced for inflating the balloon. In some embodiments, fluid is injected at a volume sufficient to inflate the balloon to a size in which of the anatomical lumen in which treatment is performed are contacted by the external walls of the balloon.

In some embodiments, the connector comprises strain-relief mechanisms for reducing or preventing kinking of the electrical connections (e.g. wires, cables) extending inside the shaft.

FIGS. 24A-B are enlarged views of a distal catheter portion surrounded by a balloon, according to some embodiments.

In some embodiments, a distal head portion of the catheter comprises a plurality of energy emission elements such as transducers 2401 peripherally mounted on a chassis 2403. In some this example, 3 transducers are arranged in a triangular configuration on a chassis having a triangular cross section profile. Optionally, energy emitted by the 3 transducers is directed to 3 different directions, simultaneously or in an alternating manner.

In some embodiments, electrical connections to the plurality of transducers are provided through one or more wires or cables 2405 extending proximally through a shaft 2407 of the catheter. In some embodiments, electrical connections to the plurality of transducers are provided via chassis 2403, for example when the chassis is formed of an electrically conductive material. In an exemplary embodiment, electrical connections to the transducers are provided both via the chassis (such as conducted via the walls of the chassis itself) and through the wires or cables 2405 which pass inside the lumen of the chassis.

In some embodiments, a distal tip 2409 of the catheter is atraumatic, for example, shaped and/or sized so that it does not puncture or cut surfaces coming in contact with the tip, such as the inner walls of a balloon 2411 (for example, in a collapsed state of the balloon) and/or body tissue coming in contact with the distal tip. Optionally, distal tip 2409 has rounded or curved walls. Optionally, distal tip 2409 has a circular profile, for example, being ball shaped.

FIGS. 25A-B are isometric views of an adapter 2501 which couples a proximal portion of a catheter for example as described herein to a bronchoscope working channel, according to some embodiments.

In some embodiments, the adapter comprises a distal coupler 2503 which attaches to a proximal end of a bronchoscope working channel (not shown). In some embodiments, coupler 2503 defines an inner lumen 2505 shaped and sized according to a cross section profile of the bronchoscope working channel, for example so as not to interfere with access into the working channel. In some embodiments, coupler 2503 is shaped to connect to the working channel in a sealed manner, for example so that air does not leak out of the working channel and/or air does not enter at the attachment of the adapter to the working channel.

In some embodiments, the adaptor comprises a proximal coupler 2507 configured to receive and hold a proximal portion of a catheter device (not shown) which is inserted through the bronchoscope working channel. In some embodiments, the proximal coupler is shaped to engage a cylindrical shaft of the catheter, for example, the proximal coupler is C-shaped and configured to fit about at least a portion of a catheter shaft circumference.

In some embodiments, the distal coupler and the proximal coupler are connected to a handle portion 2509 (also referred to herein as an "adaptor body"). In some embodiments, one or both of the proximal coupler and the distal coupler are configured to axially slide along a long axis 2511 of the handle portion. In some embodiments, the handle portion comprises an axially extending slot 2513, and a knob 2515 which extends from the proximal coupler 2507 through the slot is configured to slide along the slot.

In some embodiments, in use, the catheter is inserted into a working channel of the bronchoscope. A proximal portion of the catheter is then attached to the proximal coupler 2507, and a proximal end opening of the working channel is attached (optionally, inserted) to the lumen of the distal coupler 2503. A user (e.g. physician, surgeon) holding the handle portion 2509, (optionally single handedly), can then maneuver the catheter using the handle portion and/or the knob 2515. For example, sliding the knob axially (advancing or retracting) along the slot moves the catheter axially. For example, rotating the handle as a whole transfers torque to produce rotation of the catheter (for example, up to 90 degree, 180 degree, 180 degree rotation). In some embodiments, the catheter rolls about its long axis.

Potential advantages of coupling the bronchoscope working channel to the catheter for example using an adapter as described herein may include that the catheter proximal portion (optionally, a handle of the catheter) extending proximally from the proximal end of the bronchoscope working channel remains stable and held by the adaptor, as opposed to freely "hanging" from the proximal end of the working channel; that the catheter and the working channel are held, at least in part, at a selected alignment with respect to each other; that manipulation of the catheter may be facilitated by performing it via the adaptor.

In some embodiments, the adaptor is provided as an integral part of the catheter, for example, integrally formed on a proximal portion (e.g. handle portion) of the catheter.

In some embodiments, the catheter and adaptor are provided together in a kit.

FIG. 26 schematically illustrates shielding which reduces or prevents thermal damage to non-targeted tissues or organs, according to some embodiments.

In some embodiments, for protecting tissue and/or organs such as the esophagus 2651 from thermal damage produced by the energy emitted from the device transducer(s) 2653, a physical shield 2655 is provided to at least partially block the transfer of energy (such as ultrasound energy) through. In some embodiments, shield 2655 is arc shaped, and optionally extends axially along the length of the transducer(s).

In some embodiments, the shield is arc shaped and extends along less than 40%, less than 50%, less than 30%, less than 20% or intermediate, longer or shorter portion of the catheter head perimeter.

In some embodiments, the shield is formed of a material suitable for blocking or reducing transfer of ultrasound energy therethrough, for example, formed of one or more of: plastic, metal, foam, captive air, and/or other materials. In some embodiments, the shield is thermally isolated (optionally, covered by thermally isolating material).

The shield may be rigid (for example, when affixed to the catheter head, such as to the catheter chassis) or flexible/elastic (for example, when attached to the inner walls of the balloon).

In some embodiments, in use, the catheter is inserted into the bronchus 2657; a balloon 2659 is inflated; and ultrasound energy is emitted by transducer(s) 2653, such as for thermally damaging nerve tissue surrounding the bronchus. In some embodiments, before emission of energy, the catheter is rotationally oriented so that shield 2655 is located between the esophagus and the transducers. This may be achieved, for example, using imaging, and/or by rotating the catheter so that the shield faces dorsally (towards the patient back).

Additionally or alternatively to using a shield, in some embodiments, parameters of the emitted ultrasound energy (e.g. frequency, intensity, duration) are selected so as not to reach non-targeted tissue such as the esophagus. In some embodiments, parameters of the emitted ultrasound energy are selected so that the energy will reach a depth sufficient to pass through collagen layers surrounding the bronchus.

Additionally or alternatively to using a shield, in some embodiments, the one or more transducers of the catheter device are spatially arranged so that at least one space is formed between them, the space being large enough to reduce or avoid energy from traveling in a direction which the space faces when the catheter is rotationally oriented accordingly.

In some embodiments, distance detecting methods and/or an organ identifying methods for example as described herein are performed for determining a location and/or relative distance of non-targeted tissue such as the esophagus. In some embodiments, based on the results, the catheter is rotationally orientated to prevent or avoid damage to the non-targeted tissue. In some embodiments, based on the results, the plurality of transducers of the catheter head are selectively activated, for example so as to avoid energy emission in a direction of the non-target tissue.

FIGS. 27A-B schematically illustrate catheter head structures comprising a shield for preventing or reducing thermal damage to non-targeted tissues, according to some embodiments.

In some embodiments, as shown for example in FIG. 27A, a catheter head comprises a transducer 2701 (optionally, ring shaped or disc shaped). In some embodiments, the transducer lies on a plane that is substantially perpendicular to a long axis 2703 of the catheter. In some embodiments, the catheter head includes a reflector 2705, optionally, a cone shaped reflector (also shown at a cross section view), shaped and positioned to reflect the ultrasound energy emitted by the transducer in a direction different than a direction in which the energy travels as it is emitted by the transducer. For example, the cone shaped reflector 2705 is configured for "mirroring" the energy emitted by transducer 2701 in a radially outwards direction. In some embodiments, a shield 2707 is provided to reduce or fully block the energy from traveling in a defined circumferential region, for example to reduce or prevent damage to non-targeted tissue such as the esophagus.

In some embodiments, the reflector is shaped and positioned to simultaneously reflect and divert and the ultrasound energy (e.g. non-focused ultrasound energy) emitted by the transducer.

In some embodiments, as shown for example in FIG. 27B, a catheter head comprises more than one reflector, for example, two cone shaped reflectors 2709. In such construction, a transducer 2711 may be positioned amid the two reflectors, and optionally emit energy from both of its opposing surfaces, which is then reflected by the cones. Optionally, a shield 2707 is provided.

In some embodiments, the energy is emitted from the transducer in a substantially cylindrical beam, and once the ultrasonic waves reach the reflector, the reflector deflects the waves radially outwardly.

FIGS. 28A-B schematically illustrate catheter head structures comprising a shield for preventing or reducing thermal damage to non-targeted tissues.

In the example of FIG. 28A, a catheter head (shown at a cross section view and at a side view) comprises a cylindrical transducer 2801, and a shield 2803 extending along a portion of the transducer perimeter.

In the example of FIG. 28B, a catheter head (shown at a cross section view and at a side view) comprises a C-shaped (or horseshoe shaped) transducer 2805. Optionally, a shield 2807 is positioned at the open end of the C-shape. Alternatively, a shield is not provided, and due to the C-shape of the transducer, energy is not emitted towards a circumferential direction of the open end of the C-shape.

FIGS. 29A-B schematically illustrate catheter heads configured for emission of energy only towards a limited circumferential region, according to some embodiments.

In the examples shown, a catheter head comprises, for example, two transducers 2901, spatially arranged on a chassis 2903 (FIG. 29A)/2904 (FIG. 29B) such that a portion 2905 of the chassis (e.g. a chassis wall, face or surface) remains uncovered by a transducer (optionally, exposed), so that energy is not emitted in a radially outwardly direction which the uncovered chassis portion faces.

FIG. 29A shows a sector-shaped chassis 2903 where the arc portion of the sector remains exposed; FIG. 29B shows a triangular shaped chassis 2907 where one of the faces of the triangle 2909 remains exposed.

Additionally or alternatively to spatially arranging the plurality of transducers with a spacing between them (such as an exposed chassis portion between them), in some embodiments, partial, limited coverage may be obtained by actuating only two of the plurality of transducers (e.g. two out of three transducers in a triangular arrangement).

FIGS. 30 and 31 are a schematic illustration and an image of a catheter comprising proximal handle mechanism for rotating a distal head of the catheter without rotating a balloon which surrounds the catheter head, according to some embodiments.

In some embodiments, as shown in the examples of FIG. 30 and FIG. 31, a catheter is uni-directional, for example, comprises a single planar transducer 3001. In some embodiments, for controlling a direction of energy emission by the transducer, an elongate shaft 3003 extends from the catheter head to a proximal handle 3005. In some embodiments, rotation of the handle (for example, about its long axis) rotates the catheter head so that an emitting surface of transducer 3001 faces a desired direction. In some embodiments, an inflated balloon 3007 which surrounds the catheter head remains unaffected by the rotation of the transducer, for example, the balloon remains at a same rotational orientation when the transducer inside it is rotated.

In some embodiments, a distal end of the catheter comprises an a-traumatic tip 3009, for example, a rounded (e.g. ball shaped) tip.

FIG. 32 is a flowchart of a method for identifying a medium and/or changes in medium according to ultrasound echoes, according to some embodiments.

In some embodiments, the method is performed before and/or during a denervation procedure, optionally carried out by the same catheter device used for carrying out the method. In some embodiments, the method is performed for determining a relative location of tissue or an organ, for example, determining where the esophagus is located relative to the catheter head, based on a detected change in medium (such as a change from a fluid medium (e.g. saline, blood) to an air filled cavity (e.g. inside the esophagus).

In some embodiments, at 3201, a head of the catheter is positioned in the bronchial system (e.g. in the right bronchus and/or left bronchus). Additionally or alternatively, the catheter head is positioned in the trachea.

In some embodiments, at 3203, ultrasound energy is emitted by the one or more transducers of the catheter head. In some embodiments, parameters of the emitted ultrasound energy are different than those applied for denervation: for example, the energy is applied in pulses having a shorter duration and/or a higher intensity than pulses used for thermally damaging nerves.

In some embodiments, voltage across the surface(s) of the one or more transducers is continuously recorded during and following the emission of pulses.

In some embodiments, at 3205, returning echoes are received at the one or more transducers, optionally recorded as a voltage change across the transducer's surface.

In some embodiments, at 3207, the returning echoes are analyzed and optionally processed (such as via signal processing and/or machine learning algorithms) to determine a change in medium. Examples of different mediums which may be identified by analysis of the returning echoes include: blood, saline or water, air, vacuum, fat tissue, soft tissue, collagen tissue, connective tissue, balloon material, plastic material (e.g. a tube inserted into the esophagus).

In some embodiments, in addition or alternatively to identifying a change in medium, a location and/or a distance of the detected medium relative to the emitting transducers(s) is identified.

A potential advantage of identifying a medium and/or a change in medium may include the ability to: plan the advancement path of the catheter head; orientate (e.g. rotate) the catheter head according to the detected medium or change thereof; and/or avoid emission of treatment energy towards non-targeted tissue or organs identified according to their type of medium (e.g. air in the esophagus).

In some embodiments, an air filled conduit is introduced into the esophagus to maintain it non-collapsed, and thereby to potentially facilitate identifying the esophagus by the catheter (such as by identifying the air medium inside the conduit).

FIGS. 33-39C include details and results of experiments performed by the inventors of this application in swine and sheep models for assessing targeted lung denervation using systems and/or methods for example as described herein.

Figure 33:
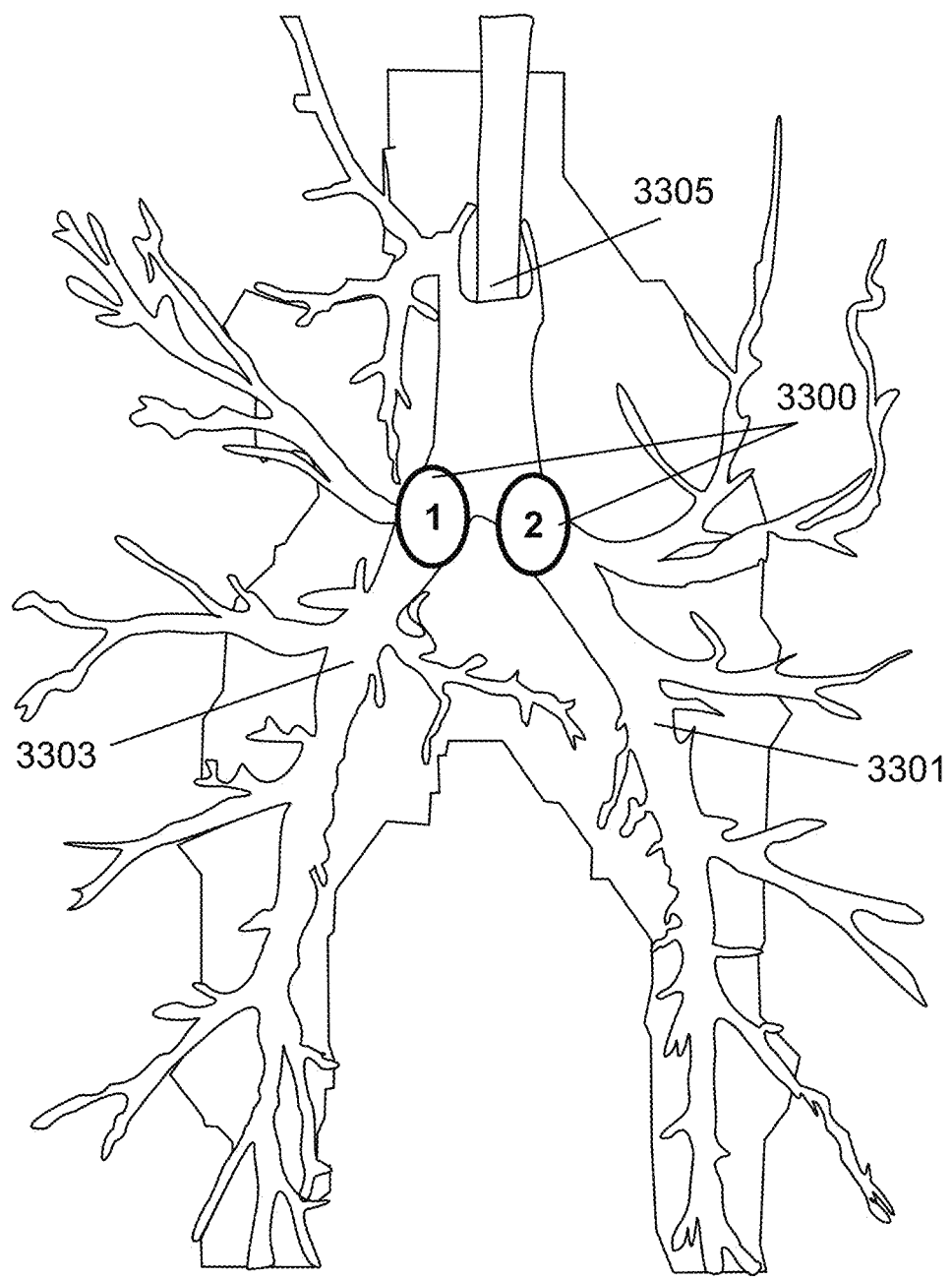
Figures 36B, 36C, 36D:
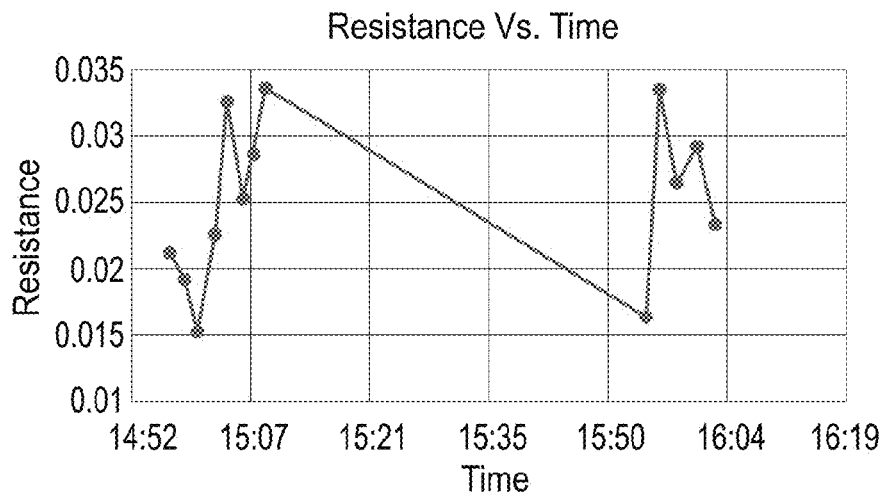

FIG. 33 shows examples of intended treatment locations 3300 for carrying out denervation, including the left bronchus 3301 and/or the right bronchus 3303, optionally at the bifurcation with the trachea 3305, as shown.

In some embodiments, treatment which targets the cholinergic neural system, for example from the described location, is effective to reduce a level of cholinergic activity and/or reduce hypersensitivity, thereby potentially reducing exacerbation events in patients suffering, for example, from COPD and/or asthma.

A potential advantage of the described location(s) is improved accessibility for delivering energy through the tissues and into the intracellular matrix and nerve bundles located outside of the bronchus, to ablate the nerves.

In the experiments performed, the efficacy of denervation treatment was assessed by measuring pulmonary resistance, by measuring a Herring Breuer Reflex (HBR), and by histopathological analysis.

In the experiments, a TIBUS catheter for example as described herein was introduced via a bronchoscope to the treatment locations shown for example at FIG. 33. The bronchoscope itself was inserted into the trachea via a laryngeal tube.

The catheter used in the experiments was controlled and powered by an operation console for example as described herein.

The catheter distal portion (including the catheter head) was surrounded by a balloon filled with saline, enabling the applying of treatment from within an airway, with the saline acting as a transfer medium for the transfer of non-focused ultrasound energy to the tissue surrounding the airways (e.g. surrounding the bronchus). The balloon was formed of ChornoPrene material.

A temperature of the saline inside the balloon was monitored and presented (via a user interface of the control console) to the physician.

The catheter head included a triangular arrangement of three ultrasound transducers directed towards three circumferential directions. In the described experiments, shielding for example as described herein was not performed.

The swine and sheep models tested in the experiment were sedated and anesthetized. Their vital signs (heart rate, oxygen saturation, systemic blood pressure, ECG, and body temperature) were monitored throughout the procedure.

During the procedure, the catheter was navigated via the bronchoscope to the treatment location(s). The balloon was filled with cold saline at a volume sufficient for obtaining contact between the external walls of the balloon and the inner walls of the bronchus lumen. A proximal end portion of the catheter was held and maneuvered using an adaptor for example as described in FIGS. 25A-B. A syringe for injection of the saline was attached via a proximal extension tube to the catheter (so as to reduce weighing down on the catheter proximal portion).

Excitation of the transducers was carried out according to a treatment protocol, and energy parameters were controlled using the control console. To ensure coverage of the bronchus perimeter (for example 85%, 90%, 95% or intermediate, larger or smaller percentage of circumferential coverage), the catheter head was rotated at 180 degrees, so that at each treatment location two excitations were performed, wherein in each the energy was targeted towards different portions of the bronchus perimeter.

Following excitation, the saline was extracted out of the balloon. In some of the cases, the saline was extracted during the procedure and replaced by a new syringe of cold saline.

At the end of the procedure, methods for detecting relative distance and/or a change in medium for example as described herein were tested and the results recorded.

HBR assessment (see results in FIG. 34) was performed before the procedure to ensure that the reflex is active and to evaluate the pressure and inflation volume required for activating the reflex. The assessment was performed during spontaneous respiration, and involved placing a 9F OTS balloon catheter in the bronchus in a location distal to the intended treatment site. The balloon was inflated to block the air passage through the bronchus, and then a distal lobe of the lung being tested was inflated (via the catheter internal lumen) to reach a selected positive pressure. During the rise in pressure, the respiratory flow was examined and monitored for determining HBR functionality. The tested models exhibited the reflex when tested.

HBR assessment was performed again following the procedure in a similar manner, using the pressure and inflation volume that were determined before the procedure. As can be observed in FIG. 34, for a first tested model, the reflex was not observed for both the right and left bronchus, indicating that the nerve responsible for activation of the reflex was damaged as planned. For a second tested model, the reflex was not observed for the right bronchus but was observed for the left bronchus,—this may be due to that in the right bronchus, some of the excitations were performed at non-intended locations, such as externally to the bronchus.

FIGS. 35A-36D show various results of assessment of airway resistance and changes in airway resistance associated with the denervation treatment.

Prior to the assessment of airway resistance, mechanical ventilation was initiated and maintained until the airway resistance assessment performed following the denervation procedure.

In order to be able to calculate accurately the change in the airway resistance, a dedicated system was established, comprised of: A pressure gauge: For measuring the required pressure values which will be detailed below, and for measuring the accurate time duration of the inspiratory rise phase.

An airflow gauge: For measuring the airflow during the inspiratory rise phase.

A scope: Required for communicating with the pressure gauge.

A laptop: programmed with dedicated algorithms for communicating and presenting the signals received from the two gauges.

For each of the tested models, the following parameters were monitored and recorded:

Peak airway pressure [cmH2O]: Measured by the pressure gauge.

Plateau airway pressure at inspiration pause [cmH2O]: Measured by the pressure gauge.

Tidal volume [L]: As indicated on the anesthesia machine display.

Airflow $$\left[\frac{L}{M}\right]$$

Measured by the airflow gauge.

The airway resistance was then calculated using the following equation:

$$R_{airway} = \frac{\Delta}{F_{airway}}$$

While:

$$\Delta P = P_{peak} - P_{plateau}$$

The airflow parameter ($F_{airway}$) was calculated using two different methods:

First Method:

$$F_{airway} = \frac{V_{tidal}}{T}$$

In this method the calculation is based on the pressure gauge, and the anesthesia machine data.

Second Method:

$F_{airway}$=is received from the airflow gauge

In this method the calculation is based on the pressure gauge, and the airflow gauge data.

The above parameters were monitored and recorded during the following phases:

1. Prior to the denervation procedure-in order to calculate the baseline airway resistance.
2. Following intravascular (IV) injection of Atropine s-in order to examine the effect of induced relaxation on the animal's airway resistance.

Atropine was administered to the first animal model (7 mg were administered, and then an additional 7 mg were administered, since no significant response was observed following the first administration). The above mentioned parameters were recorded following the Atropine injection, and then every 4-10 minutes in order to identify a maximal decrease in the airway resistance due to the relaxation induced by the Atropine, and in order to identify the return to baseline airway resistance (following Atropine dissipation).

In the second animal model, Atropine administration was not performed due to the fact that pneumonia findings were observed during the pre-procedure scanning, and it was decided to minimize unnecessary load on the treated animal.

3. Following the denervation procedure (referred to in the figures as "TLD"-targeted lung denervation) in order to examine the effect of denervation on airway resistance. The above mentioned parameters were recorded three-five times, every 2-5 minutes.

In each one of the phases listed above, the recorded parameters were calculated in real-time in order to evaluate the progress and the effectiveness of the procedure in real-time. This calculation was carried out based on a single (random) respiration cycle occurring during each of the above phases.

A more comprehensive analysis of the recorded parameters was carried out using a dedicated MATLAB script, which averaged results of multiple respiration cycles occurring during each of the above phases.

FIGS. 35A-D show the results of airway resistance analysis for the first animal model.

As can be observed, following the targeted lung denervation, airway resistance values decreased significantly (by 39%) as compared the baseline airway resistance value.

FIGS. 36A-D show the results of airway resistance analysis for the second animal model.

As can be observed, a small increase was observed in the average airway resistance value (when comparing the values before and after denervation). It is assumed that these findings may be associated with an erred location of treatment resulting in that some of the nerves were not sufficiently thermally damaged.

FIGS. 37A-B include details of the denervation treatment performed on the animal models, in accordance with some embodiments.

For the first model (upper table), a total of four excitations were performed in the right and left bronchi, using a fixed excitation power (50 W/cm^2).

For the second model (lower table), a total of six excitations were performed in the right and left bronchi, using a fixed excitation power (50 W/cm^2) and a fixed excitation duration (60 seconds). (The treatment location indicated as "1" included an adjusted location from an initial position indicated by "1").

It is noted that other energy parameters and ranges thereof are covered and may effectively obtain a desired thermal damage of the nerves innervating the airways and/or lungs, including, for example: excitation power of 40 W/cm^2 applied for a duration of 40 seconds; 40 W/cm^2 for a duration of 50 [Sec]; 35 W/cm^2 for a duration of 60 [Sec]; 45 W/cm^2 for a duration of 30 [Sec]; 30 for a duration of 60 [Sec]; +−5 W/cm^2+−10 Sec.

Figure 38A:
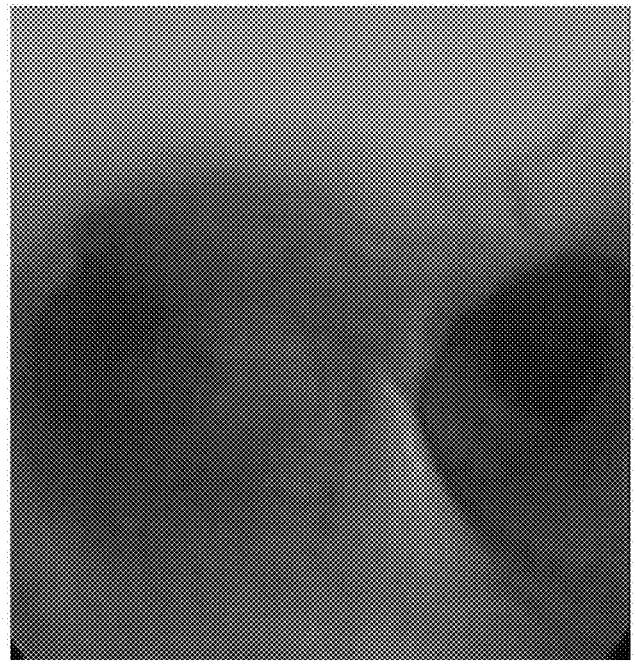
Figure 38B:
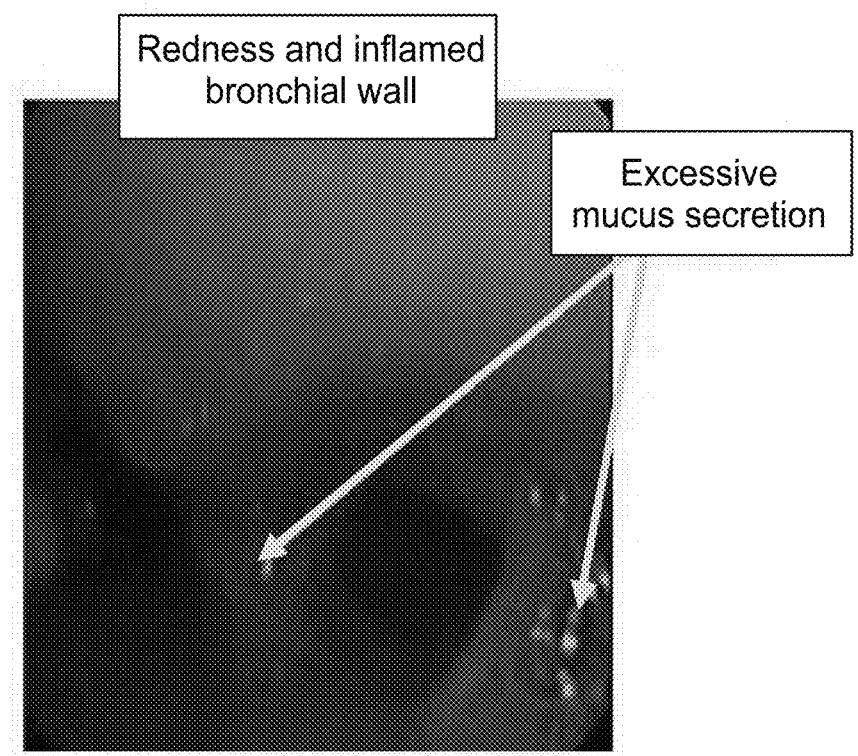

FIGS. 38A-B show images obtained during the procedure using the bronchoscope. The trachea and the bronchus were scanned and videoed continuously. FIG. 38A is an image of the bifurcation of the right and left bronchi from the trachea obtained from the first model. FIG. 38B is an image of the bifurcation of the right and left bronchi from the trachea obtained from the second model, showing indications of pneumonia such as redness, inflamed bronchial wall, excessive mucus secretion.

Figures 39A, 39B:
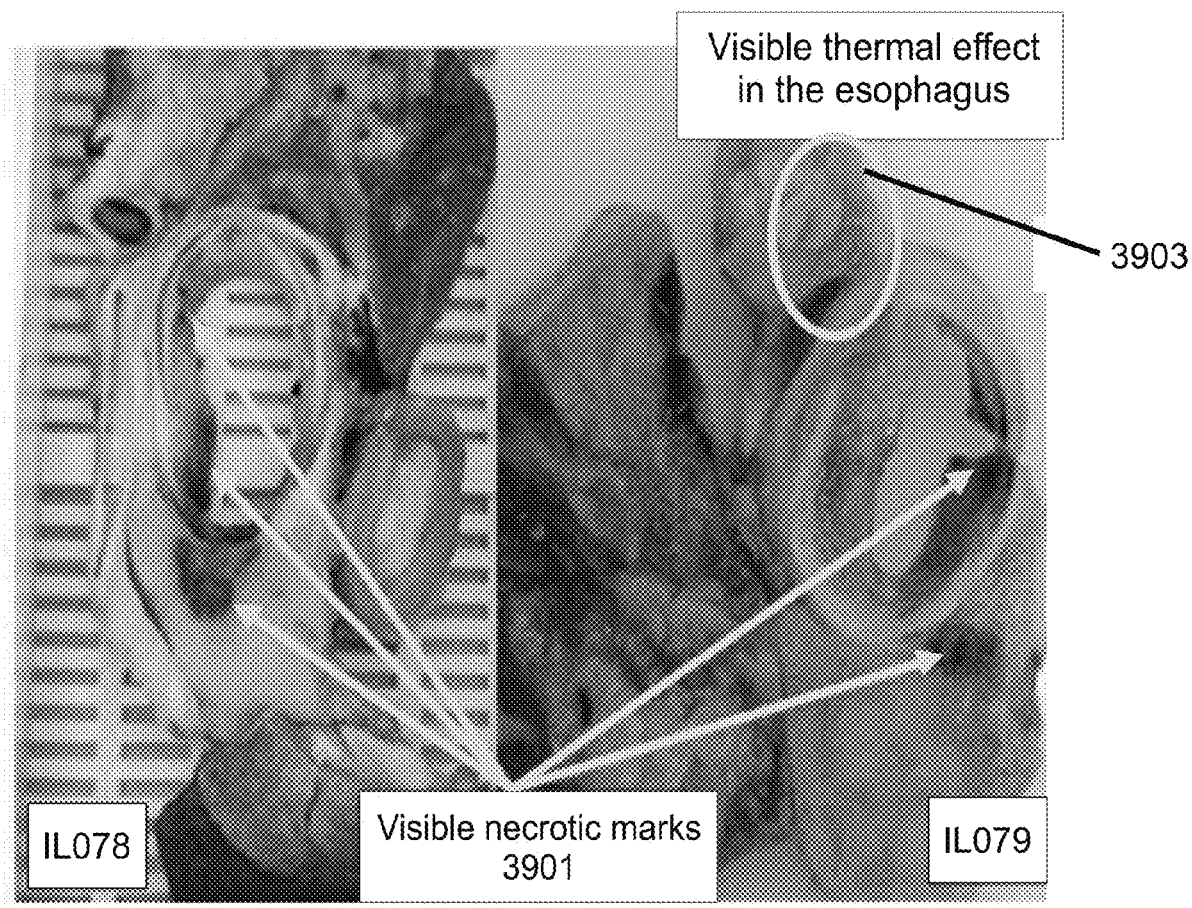
Figure 39C:
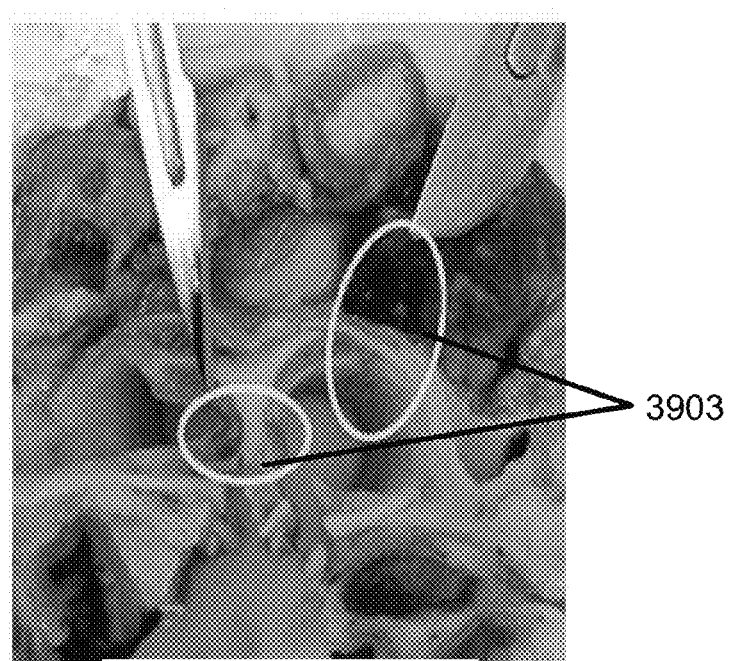

FIGS. 39A-C are images of a histopathology analysis performed on the animal models. The trachea, bronchi, esophagus, and lungs were harvested post mortem and analyzed.

Necrotic regions (thermally damaged regions) 3901 are indicated by the arrows, showing that the targeted denervation treatment effectively damaged nerve tissue surrounding the treated airways. Thermal necrosis was found mainly in collagen coagulation, pyknosis and vacuolization. No thermal necrosis was identified in the bronchial cartilage ring. Thermal necrosis was present in both the luminal layers of the bronchus and in the soft tissues surrounding the cartilage. The damage was especially visible at or close to bifurcations.

In FIG. 39B and FIG. 39C, a non-desired thermal effect (encircled) 3903 was observed in the esophagus. Thermal coagulation was observed adjacent the esophagus and in the wall of the esophagus, reaching the luminal side of the esophagus and affecting the esophageal muscle. It is noted that potentially use of a shield for example as described herein (e.g. in FIGS. 26, 28A-B) would reduce or prevent thermal damage to non-target tissue such as the esophagus.

In FIG. 39A, no damage to the esophagus was exhibited.

Additional observations included focal hemorrhages in the lungs, which were limited to a small region; epithelial loss, pyknosis. Such observations are common in bronchial procedures and were not considered of high risks.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of reducing of at least one of excess mucosa production or excess mucosa secretion in the respiratory tract, comprising:
   introducing into a respiratory tract lumen a device configured for damaging nerve tissue or blocking neural conduction in the surroundings of said lumen, said device comprising a plurality of ultrasound emitting transducers;

positioning said ultrasound emitting transducers of said device inside said respiratory tract lumen at a distance from walls of said lumen, wherein said positioning comprises positioning said ultrasound emitting transducers within the lumen of the bronchi at a distance of between 0.5 cm to 20 cm from the trachea bifurcation; and activating said ultrasound emitting transducers to emit non-focused ultrasound energy suitable to damage said nerve tissue enough to suppress parasympathetic nerve activity which causes said at least one of excess mucosa production or excess mucosa secretion.

2. The method according to claim 1, comprising, prior to said introducing, selecting patients suffering from a respiratory condition associated with excess mucosa production and/or secretion, said respiratory condition being from the group of: bronchitis, chronic bronchitis, COPD, pneumonia, lung inflammation; and performing said introducing, said positioning and said activating on said selected patients.

3. The method according to claim 1, comprising, prior to said introducing, selecting patients suffering from a viral infection associated with excess mucosa production and/or secretion, said viral infection being from the group of: SARS, SARS-2, MERS, SARS-COV-2, COVID-19; and performing said introducing, said positioning and said activating on said selected patients.

4. The method according to claim 1, wherein said respiratory tract lumen comprises a lumen of the trachea or the lumen of the bronchi.

5. The method according to claim 1, wherein said activating comprises delivering via said ultrasound emitting transducers non-focused ultrasound energy suitable to thermally damage said nerve tissue.

6. The method according to claim 1, comprising introducing a blocking element into said respiratory tract lumen, and then partially filling the lumen with fluid which acts as a transfer medium for said energy; said fluid allowed to accumulate in said lumen due to said blocking element.

7. The method according to claim 1, further comprising assessing the effectiveness of treatment by sensing a humidity level in the lungs.

8. The method according to claim 1, comprising anchoring at least a portion of said device to the wall of said respiratory tract lumen.

9. The method according to claim 1, wherein said emitted non-focused ultrasound energy is suitable to thermally damage nerve tissue located peripherally to said lumen to reduce at least one of mucosa secretion, bronchoconstriction; or lung inflammation.

10. The method according to claim 1, applied for the treatment of a respiratory condition from the group of: bronchitis, chronic bronchitis, COPD, pneumonia, lung inflammation.

11. The method according to claim 1, applied for the treatment of a respiratory condition associated with a viral infection from the group of: SARS, SARS-2, MER, COVID-19, SARS-COV-2.

12. The method according to claim 1, wherein an intensity of said non-focused ultrasound energy is between 10 W/cm$^2$-80 W/cm$^2$ and a frequency is between 8 MHz-20 MHz.

13. The method according to claim 1, wherein said plurality of ultrasound emitting transducers are positioned within a fluid filled balloon.

14. The method according to claim 1, wherein said ultrasound emitting transducers comprise planar ultrasound emitting transducers.

15. A system for treating a respiratory disorder by suppression of nerve activity, comprising:

a catheter shaped and sized for insertion into a lumen of a trachea or a bronchus, the catheter including a head comprising one or more ultrasound emitting transducers, each having an emitting surface, wherein said one or more ultrasound emitting transducers are configured to generate and emit non-focused ultrasound energy via said emitting surface;

a balloon inflatable with a fluid medium and configured to surround said head, wherein when inflated said balloon is configured to anchor said head within said lumen and positions said emitting surface of said one or more ultrasound emitting transducers at a desired direction towards a wall of said trachea or said bronchus; and a shield positioned and configured to block at least a portion of the energy emitted by said one or more ultrasound emitting transducers, wherein said shield comprises an arc shaped cross section which extends along less than 50% of a perimeter of said catheter head.

16. The system according to claim 15, comprising a control console configured for controlling emission of energy by the one or more ultrasound emitting transducers, the control console configured for setting energy parameters suitable to thermally damage nerve tissue surrounding the lumen into which the catheter is inserted.

17. The system according to claim 16, wherein said control console is configured for setting intensity of said non-focused ultrasound energy in between 10 W/cm$^2$-80 W/cm$^2$ and a frequency of said non-focused ultrasound energy in between 8 MHz-20 MHz.

18. The system according to claim 15, wherein said catheter is sized to be introduced into said lumen via a working channel of a bronchoscope.

19. The system according to claim 15, wherein said shield is formed of a material configured for absorbing ultrasound energy emitted by said one or more ultrasound emitting transducers.

20. The system according to claim 15, wherein said one or more ultrasound emitting transducers comprises at least one planar ultrasound emitting transducer.

* * * * *